US010865224B2

(12) United States Patent
Xenopoulos et al.

(10) Patent No.: US 10,865,224 B2
(45) Date of Patent: *Dec. 15, 2020

(54) PURIFICATION OF BIOLOGICAL MOLECULES

(71) Applicant: EMD Millipore Corporation, Burlington, MA (US)

(72) Inventors: Alex Xenopoulos, Cambridge, MA (US); Michael Phillips, Billerica, MA (US); Wilson Moya, Carlisle, MA (US); Jad Jaber, Sudbury, MA (US); Mikhail Kozlov, Lexington, MA (US); Ajish Potty, Missouri City, TX (US); Matthew T. Stone, Arlington, MA (US); William Cataldo, Bradford, MA (US); Christopher Gillespie, Shirley, MA (US)

(73) Assignee: EMD Millipore Corporation, Burlington, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 15/654,876

(22) Filed: Jul. 20, 2017

(65) Prior Publication Data

US 2017/0320909 A1 Nov. 9, 2017

Related U.S. Application Data

(62) Division of application No. 14/400,389, filed as application No. PCT/US2013/046995 on Jun. 21, 2013, now abandoned.

(60) Provisional application No. 61/666,521, filed on Jun. 29, 2012, provisional application No. 61/666,561, filed on Jun. 29, 2012, provisional application No. 61/666,329, filed on Jun. 29, 2012.

(30) Foreign Application Priority Data

Jul. 2, 2012 (EP) .................................... 12004909

(51) Int. Cl.
*C07K 1/36* (2006.01)
*C07K 1/16* (2006.01)
*C07K 1/30* (2006.01)
*B01D 15/12* (2006.01)
*B01D 15/36* (2006.01)
*B01D 15/38* (2006.01)
*C12M 1/00* (2006.01)
*B01D 15/18* (2006.01)
*C07K 16/00* (2006.01)
*C12N 7/00* (2006.01)

(52) U.S. Cl.
CPC .............. *C07K 1/36* (2013.01); *B01D 15/125* (2013.01); *B01D 15/1871* (2013.01); *B01D 15/362* (2013.01); *B01D 15/363* (2013.01); *C07K 16/00* (2013.01); *C12M 29/04* (2013.01); *C12M 43/00* (2013.01); *C12M 47/12* (2013.01); *C12N 7/00* (2013.01); *B01D 15/3809* (2013.01); *B01D 15/3847* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 1,007,849 | A | 11/1911 | Crandall |
| 1,419,177 | A | 6/1922 | Stahl |
| 4,434,157 | A | 2/1984 | Olsen |
| 4,480,034 | A | 10/1984 | Hsieh |
| 4,490,937 | A | 1/1985 | Yavnieli |
| 4,765,903 | A | 8/1988 | D Andrea et al. |
| 4,808,523 | A | 2/1989 | Revel et al. |
| 4,816,567 | A | 3/1989 | Cabilly et al. |
| 4,820,825 | A | 4/1989 | Ootani et al. |
| 4,855,494 | A | 8/1989 | Margureanu et al. |
| 4,921,792 | A | 5/1990 | Trawinski et al. |
| 5,091,178 | A | 2/1992 | Hellstrom et al. |
| 5,173,164 | A | 12/1992 | Egen et al. |
| 5,256,694 | A | 10/1993 | Wuest et al. |
| 5,571,720 | A | 11/1996 | Grandics et al. |
| 6,054,051 | A | 4/2000 | Van Reis |
| 6,171,638 | B1 | 1/2001 | Gugger et al. |
| 6,197,553 | B1 | 3/2001 | Lee et al. |
| 6,214,221 | B1 | 4/2001 | Kopf |
| 6,281,336 | B1 | 8/2001 | Laursen et al. |
| 6,383,380 | B1 | 5/2002 | Kopf |
| 6,461,858 | B1 | 10/2002 | Gabriel et al. |
| 6,525,233 | B1 | 2/2003 | Connor et al. |
| 6,551,512 | B1 | 4/2003 | Britsch et al. |
| 6,573,366 | B1 | 6/2003 | Zanette et al. |
| 6,596,172 | B1 | 7/2003 | Kopf |
| 6,610,863 | B2 | 8/2003 | Arumugam et al. |
| 6,663,780 | B2 | 12/2003 | Heikkila et al. |
| 6,709,527 | B1 | 3/2004 | Fechter et al. |
| 6,802,967 | B2 | 10/2004 | Masuda et al. |
| 6,806,355 | B2 | 10/2004 | Joergensen et al. |

(Continued)

FOREIGN PATENT DOCUMENTS

| | | |
|---|---|---|
| CN | 1817907 A | 8/2006 |
| CN | 101029077 A | 9/2007 |

(Continued)

OTHER PUBLICATIONS

Bioprocess International "Disposable Bioreactors in cell culture-based upstream processing" Feb. 1, 2009, pp. 18-23 (Year: 2009).*

(Continued)

*Primary Examiner* — Daniel E Kolker
*Assistant Examiner* — James L Rogers
(74) *Attorney, Agent, or Firm* — EMD Millipore Corporation

(57) ABSTRACT

The present invention relates to improved processes and systems for purification of biological molecules, where the processes can be performed in a continuous manner.

29 Claims, 25 Drawing Sheets

(56) References Cited

U.S. PATENT DOCUMENTS

| | | | |
|---|---|---|---|
| 6,864,376 B2 | 3/2005 | Perri et al. | |
| 6,870,034 B2 | 3/2005 | Breece et al. | |
| 6,875,459 B2 | 4/2005 | Kopf et al. | |
| 6,921,808 B2 | 7/2005 | Joergensen et al. | |
| 6,946,075 B2 | 9/2005 | Kopf | |
| 6,995,006 B2 | 2/2006 | Atkinson et al. | |
| 7,048,211 B2 | 5/2006 | Bratcher et al. | |
| 7,118,675 B2 | 10/2006 | Siwak et al. | |
| 7,125,455 B2 | 10/2006 | Costesso et al. | |
| 7,138,120 B2 | 11/2006 | Laursen et al. | |
| 7,141,171 B2 | 11/2006 | Lightfoot, Jr. | |
| 7,323,553 B2 | 1/2008 | Fahrner et al. | |
| 7,396,519 B2 | 7/2008 | Lin et al. | |
| 7,465,397 B2 | 12/2008 | Siwak et al. | |
| 7,468,151 B2 | 12/2008 | Van Buitenen et al. | |
| 7,622,308 B2 | 11/2009 | Hendler et al. | |
| 7,662,234 B2 | 2/2010 | Costesso et al. | |
| 7,700,762 B2 | 4/2010 | Antoniou | |
| 7,771,945 B2 | 8/2010 | Au-Yeung et al. | |
| 7,807,822 B2 | 10/2010 | Bridenbaugh et al. | |
| 7,931,751 B2 | 4/2011 | Costesso et al. | |
| 7,966,227 B2 | 6/2011 | Johansson et al. | |
| 8,003,352 B2 | 8/2011 | Foody et al. | |
| 8,137,361 B2 | 3/2012 | Duggineni et al. | |
| 8,168,185 B2 | 5/2012 | Eon-Duval et al. | |
| 9,089,529 B2* | 7/2015 | Garidel | C07K 16/18 |
| 9,096,648 B2* | 8/2015 | Bian | B01J 20/20 |
| 9,149,738 B2* | 10/2015 | Skudas | B01D 15/3804 |
| 10,287,314 B2* | 5/2019 | Bian | C07K 16/00 |
| 2002/0030015 A1 | 3/2002 | Stipanovic et al. | |
| 2002/0095028 A1 | 7/2002 | Grimes et al. | |
| 2004/0033562 A1 | 2/2004 | Miller | |
| 2004/0063183 A1 | 4/2004 | Weymarn et al. | |
| 2004/0259240 A1 | 12/2004 | Fadden | |
| 2005/0061744 A1 | 3/2005 | Kearney et al. | |
| 2005/0226794 A1 | 10/2005 | Hodge et al. | |
| 2006/0014239 A1 | 1/2006 | Luttmann et al. | |
| 2006/0030696 A1 | 2/2006 | Bonnerjea et al. | |
| 2006/0118492 A1 | 6/2006 | Shieh et al. | |
| 2006/0142549 A1 | 6/2006 | Takeda et al. | |
| 2006/0172376 A1 | 8/2006 | Chadjaa et al. | |
| 2006/0194953 A1 | 8/2006 | Bonnerjea et al. | |
| 2007/0077232 A1 | 4/2007 | Naughton et al. | |
| 2007/0111221 A1 | 5/2007 | Blanche et al. | |
| 2007/0167612 A1 | 7/2007 | Hua Zhou | |
| 2007/0213289 A1 | 9/2007 | Blanche et al. | |
| 2007/0213513 A1 | 9/2007 | Van Alstine et al. | |
| 2007/0281349 A1 | 12/2007 | Jaczynski | |
| 2008/0093302 A1 | 4/2008 | Kearney et al. | |
| 2008/0164195 A1 | 7/2008 | Siwak | |
| 2008/0167450 A1 | 7/2008 | Pan | |
| 2008/0182305 A1 | 7/2008 | Foody et al. | |
| 2008/0207487 A1 | 8/2008 | DeFrees et al. | |
| 2008/0237110 A1 | 10/2008 | Lightfoot et al. | |
| 2008/0260468 A1 | 10/2008 | Heskin et al. | |
| 2008/0269468 A1 | 10/2008 | Vogel et al. | |
| 2008/0312425 A1 | 12/2008 | Bonnerjea et al. | |
| 2009/0035856 A1 | 2/2009 | Galliher et al. | |
| 2009/0036651 A1 | 2/2009 | Moya | |
| 2009/0050566 A1 | 2/2009 | Kozlov et al. | |
| 2009/0123503 A1 | 5/2009 | Naughton et al. | |
| 2009/0149638 A1 | 6/2009 | Ley et al. | |
| 2009/0173339 A1 | 7/2009 | Heikkila et al. | |
| 2009/0198088 A1 | 8/2009 | Tirio et al. | |
| 2009/0270609 A1 | 10/2009 | Heikkila et al. | |
| 2009/0275107 A1 | 11/2009 | Lock et al. | |
| 2009/0280565 A1 | 11/2009 | Jolicoeur et al. | |
| 2010/0024527 A1 | 2/2010 | LaMarr et al. | |
| 2010/0084344 A1 | 4/2010 | Lihme et al. | |
| 2010/0112639 A1 | 5/2010 | Carlson et al. | |
| 2010/0184149 A1 | 7/2010 | Laustsen | |
| 2010/0191361 A1 | 7/2010 | McCready et al. | |
| 2010/0221844 A1 | 9/2010 | Bian et al. | |
| 2010/0267933 A1 | 10/2010 | Wilson | |
| 2011/0008873 A1 | 1/2011 | Lipinski et al. | |
| 2011/0065901 A1 | 3/2011 | Soice et al. | |
| 2011/0070638 A1 | 3/2011 | Au-Yeung et al. | |
| 2011/0100818 A1 | 5/2011 | Jackson et al. | |
| 2011/0313066 A1 | 12/2011 | Jaber et al. | |
| 2012/0010390 A1 | 1/2012 | Van Alstine et al. | |
| 2012/0010429 A1 | 1/2012 | Sarmala et al. | |
| 2012/0016168 A1 | 1/2012 | Schabron et al. | |
| 2012/0076934 A1 | 3/2012 | Tkacik et al. | |
| 2013/0012689 A1 | 1/2013 | Singh et al. | |
| 2013/0046056 A1 | 2/2013 | Spector et al. | |
| 2013/0090284 A1 | 4/2013 | Schmidt et al. | |
| 2013/0197200 A1* | 8/2013 | Bian | B01J 20/20 530/388.1 |
| 2013/0245139 A1 | 9/2013 | Kozlov et al. | |
| 2018/0215786 A1* | 8/2018 | Kozlov | B01D 15/362 |
| 2018/0345173 A1* | 12/2018 | Singh | B01D 15/3809 |

FOREIGN PATENT DOCUMENTS

| | | | |
|---|---|---|---|
| CN | 102027010 A | 4/2011 | |
| EP | 230307 B1 | 4/1992 | |
| EP | 775335 B1 | 8/1998 | |
| EP | 832097 B1 | 10/2001 | |
| EP | 938501 B1 | 7/2004 | |
| EP | 1084147 B1 | 9/2004 | |
| EP | 1577319 A1 | 9/2005 | |
| EP | 974838 B1 | 2/2006 | |
| EP | 1419177 B1 | 4/2008 | |
| EP | 1729867 B1 | 10/2010 | |
| EP | 2040811 B1 | 8/2011 | |
| EP | 2578286 A1 | 4/2013 | |
| EP | 2639239 A2 | 9/2013 | |
| EP | 2656892 A1 | 10/2013 | |
| EP | 2942353 A1 | 11/2015 | |
| JP | 2007-525412 A | 9/2007 | |
| JP | 2010-528076 A | 8/2010 | |
| WO | 1994/025552 A1 | 11/1994 | |
| WO | 2005/000226 A2 | 1/2005 | |
| WO | 2006/024497 A1 | 3/2006 | |
| WO | 2008/025747 A1 | 3/2008 | |
| WO | 2008/025748 A1 | 3/2008 | |
| WO | 2008/091740 A2 | 7/2008 | |
| WO | 2008/145351 A1 | 12/2008 | |
| WO | WO-2008153472 A1 * | 12/2008 | B01D 15/1828 |
| WO | 2009/017491 A1 | 2/2009 | |
| WO | 2009/093997 A1 | 7/2009 | |
| WO | 2009/138484 A2 | 11/2009 | |
| WO | 2010/048192 A2 | 4/2010 | |
| WO | 2010/098867 A1 | 9/2010 | |
| WO | 2010/124159 A1 | 10/2010 | |
| WO | 2011/017514 A1 | 2/2011 | |
| WO | 2011/035282 A1 | 3/2011 | |
| WO | 2011/090720 A2 | 7/2011 | |
| WO | 2011/098526 A1 | 8/2011 | |
| WO | 2011/130809 A2 | 10/2011 | |
| WO | 2011/146394 A1 | 11/2011 | |
| WO | 2011/156073 A1 | 12/2011 | |
| WO | 2011/161088 A2 | 12/2011 | |
| WO | 2012/014183 A1 | 2/2012 | |
| WO | 2012/051147 A1 | 4/2012 | |
| WO | 2012/078677 A2 | 6/2012 | |
| WO | 2013/002831 A1 | 1/2013 | |
| WO | 2013/028334 A2 | 2/2013 | |
| WO | 2013/148389 A1 | 10/2013 | |
| WO | 2014/004103 A1 | 1/2014 | |

OTHER PUBLICATIONS

George Clifford Rut "Purification of Recombinant Proteins" Thesis Project at MIT, Dec. 1996 (Year: 1996).*

Mahajan et al. "improving affinity chromatography resin efficiency using semi-continuous chromatography" J. of Chromatography A 1227 (2012) pp. 154-162 (Year: 2012).*

Extended European Search Report and Search Opinion received for European Patent Application No. 10807153.1, dated Nov. 26, 2012, 5 pages.

(56) References Cited

OTHER PUBLICATIONS

Extended European Search Report and Search Opinion received for EP Patent Application No. 12004909.3, dated Nov. 13, 2012, 8 pages.
European Search Report received for European Patent Application No. 13808723.4, dated Sep. 9, 2016, 14 pages.
Extended European Search Report received for European Patent Application No. 16181909.9, dated Jan. 18, 2017, 8 pages.
Berg et al., "Bispecific Antibodies that Mediate Killing of Cells Infected with Human Immunodeficiency Virus of any Strain", Proceedings of the National Academy of Sciences, vol. 88, Jun. 1991, pp. 4723-4727.
Bisschops et al., "Single-Use, Continuous Countercurrent, Multicolumn Chromatography", BioProcess International, vol. 7, Jun. 2009, pp. 18-23.
Chamow et al., "A Humanized, Bispecific Immunoadhesin-Antibody that Retargets Cd3+ Effectors to Kill HIV-1-Infected Cells", The Journal of Immunology, vol. 153, No. 9, Nov. 1, 1994, pp. 4268-4280.
Chothia et al., "Canonical Structures for the Hypervariable Regions of Immunoglobulins", Journal of Molecular Biology, vol. 196, No. 4, Aug. 20, 1987, pp. 901-917.
Clackson et al., "Making Antibody Fragments Using Phage Display Libraries", Nature, vol. 352, Aug. 15, 1991, pp. 624-628.
Disclosed Anonymously, "Low pH Virus Inactivation Performed on a Chromatography Column", The Ip.com Journal, IP.com Disclosure No. IPCOM000183319D, Available online at <http://ip.com/IPCOM/000183319>, May 18, 2009, 2 pages.
Eibl et al., "Disposable Bioreactors in Cell Culture-Based Upstream Processing", Bio Process International, vol. 7, No. Supplement 5, Jun. 2009, pp. 18-23.
Gagnon, Pete, "Polishing Methods for Monoclonal IgG Purification", Chapter 17 from "Process Scale Bioseparations for the Biopharmaceutical Industry", CRC Press, 2006, pp. 491-506.
Giovannoni et al., "Antibody Purification Using Membrane Adsorbers", BioPharm International, Dec. 1, 2008, 6 pages.
Gueffroy, Donald E., "Buffers—A Guide for the Preparation and Use of Buffers in Biological Systems", Calbiochem Corporation, 1975, pp. 1-24.
Hamzik et al., "Chromatographic Three Step Antibody Purification Process with No Intermediate Tanks", Millipore Corporation, May 2010, 1 page.
Hazel, Aranha, "Ensuring Safety of Biopharmaceuticals: Virus and Prion Safety Considerations", Chapter 20, Edited by Meltzer et al., Filtration and Purification in the Biopharmaceutical Industry, 2nd edition, Informa Healthcare USA, Inc., 2008, pp. 543-577.
Jones et al., "Replacing the Complementarity-Determining Regions in a Human Antibody with Those from a Mouse", Nature, vol. 321, May 29, 1986, pp. 522-525.
Kellogg et al., "Purification of a Multiprotein Complex Containing Centrosomal Proteins from the *Drosophila* Embryo by Chromatography With Low-Affinity Polyclonal Antibodies", Molecular Biology of the Cell, vol. 3, Jan. 1992, pp. 1-11.
Kohler et al., "Continuous Cultures of Fused Cells Secreting Antibody of Predefined Specificity", Nature, vol. 256 (Attached version of document is reprinted with permission in the Journal of Immunology, 2005, vol. 174, pp. 2453-2455), Aug. 7, 1975, pp. 495-497.
Koros et al., "Terminology for Membranes and Membrane Processes", International Union of Pure and Applied Chemistry (IUPAC), 1996, pp. 1479-1489.
Lindmark et al., "Binding of Immunoglobulins to Protein A and Immunoglobulin Levels in Mammalian Sera", Journal of Immunological Methods, vol. 62, No. 1, 1983, pp. 1-13.
Liu et al., "Recovery and Purification Process Development for Monoclonal Antibody Production", mAbs, Landes Bioscience, vol. 2, No. 5, Oct. 2010, pp. 480-499.
Lutz et al., "Single-Pass TFF Processing", American Chemical Society Division of Biochemical Technology 241st ACS National Meeting, Mar. 27-31, 2011, 2 pages.
Marks et al., "By-Passing Immunization : Human Antibodies from V-Gene Libraries Displayed on Phage", Journal of Molecular Biology, vol. 222, No. 3, Dec. 5, 1991, pp. 581-597.
Millipore, "ProSep® Ultra Plus Chromatography Media—The Highest Dynamic Binding Capacity Protein A Affinity Chromatography Media, Designed for Cost Effective, Large-scale Purification of Today's Higher Titer Therapeutic Antibodies", Fisher Scientific, 2009, 6 pages.
Morrison et al., "Chimeric Human Antibody Molecules: Mouse Antigen-Binding Domains with Human Constant Region Domains", Proc. Nati. Acad. Sci. USA, vol. 81, Nov. 1984, pp. 6851-6855.
International Preliminary Report on Patentability received for PCT Patent Application No. PCT/US2010/044539, dated Feb. 7, 2012, 6 pages.
International Search Report received for PCT Patent Application No. PCT/US2010/044539, dated Oct. 14, 2010, 2 pages.
Written Opinion received for PCT Patent Application No. PCT/US2010/044539, dated Oct. 14, 2010, 5 pages.
International Preliminary Report on Patentability received for PCT Patent Application No. PCT/US2013/046995, dated Jan. 8, 2015, 17 pages.
International Search Report and Written Opinion received for PCT Patent Application No. PCT/US2013/046995, dated Oct. 11, 2013, 20 pages.
Pearson et al., "Characterization of Limulus Amoebocyte Lysate-Reactive Material from Hollow-Fiber Dialyzers", Applied and Environmental Microbiology, vol. 48, No. 6, Dec. 1984, pp. 1189-1196.
Presta, Leonard G., "Antibody Engineering", Current Opinion in Structural Biology, vol. 2, No. 4, Aug. 1992, pp. 593-596.
Riechmann et al., "Reshaping Human Antibodies for Therapy", Nature, vol. 332, Mar. 24, 1988, pp. 323-327.
Shukla et al., "Downstream Processing of Monoclonal Antibodies-Application of Platform Approaches", Journal of Chromatography B, vol. 848, 2007, pp. 28-39.
Van Reis et al., "Protein Ultrafiltration: Encyclopedia of Bioprocess Technology", John Wiley & Sons, 2003, 27 pages.
Zeman et al., "Microfiltration and Ultrafiltration: Principles and Applications", Marcel Dekker, Inc., 1996, pp. 299-301.

\* cited by examiner

PURIFICATION OF BIOLOGICAL MOLECULES

RELATED APPLICATIONS

The present application is a divisional of U.S. application Ser. No. 14/400,389, filing date Nov. 11, 2014, which is a US National Stage Application of International Application No. PCT/US2013/046995, filing date Jun. 21, 2013, which claims the benefit of priority of U.S. Provisional Patent Application No. 61/666,521, filing date Jun. 29, 2012, U.S. Provisional Patent Application No. 61/666,561, filing date Jun. 29, 2012, U.S. Provisional Patent Application No. 61/666,329, filing date Jun. 29, 2012, and European Patent Application EP12004909.3, filing date Jul. 2, 2012, each of which is incorporated by reference herein in its entirety.

FIELD OF THE INVENTION

The present invention provides inventive and efficient processes and systems for the purification of biological molecules including therapeutic antibodies and Fc-containing proteins.

BACKGROUND OF THE INVENTION

Efficient and economic large scale production of biomolecules, e.g., therapeutic proteins including antibodies, peptides or hormones, is an increasingly important consideration for the biotechnology and pharmaceutical industries. Generally, the purification processes are quite elaborate and expensive and include many different steps.

Typically, proteins are produced using cell culture methods, e.g., using either mammalian or bacterial cell lines recombinantly engineered to produce the protein of interest. In general, following the expression of the target protein, its separation from one or more impurities such as, e.g., host cell proteins, media components and nucleic acids, poses a formidable challenge. Such separation and purification is especially important if the therapeutic proteins are meant for use in humans and have to be approved by regulatory agencies, such as the Food and Drug Administration (FDA).

Conventional processes used today for the purification of proteins often include at least the following steps: (a) a clarification step for the removal of cells and cellular debris, e.g., using differential centrifugation and/or filtration; and (b) one or more downstream chromatography steps to separate the protein of interest from various impurities in the clarified cell culture feed.

While the fermentation and cell culture processes can be run either in a batch or fed-batch mode or continuously (e.g. in form of a continuous perfusion process), the downstream purification processes are typically run as batch processes that are often even physically and logistically separated. Between each process step, the sample is typically stored in a holding or pool tank or reservoir in order to change solution conditions in order to render it suitable for the next process step. Consequently, large vessels are required to store the intermediate product. This leads to high costs and very limited manufacturing flexibility and mobility.

In addition, performing a number of separate batch process steps is labor and cost intensive as well as time consuming.

In case of monoclonal antibodies, the industry standard for purification processes typically involves a "templated" process, which includes several unit operations. One of the unit operations is a purification step which employs an affinity ligand called Protein A, isolated from *Staphylococcus aureus*, and which binds the Fc-region of antibodies. Additional unit operations are usually used in conjunction with the Protein A unit operation and most biopharmaceutical companies employ process templates that are quite similar in their use of the unit operations, whereas there may be some variations in the order of the unit operations.

An exemplary templated process used in the industry today is shown in FIG. 1. Key aspects of this template is a cell harvest step, which typically involves use of centrifugation to remove cell and cell debris from a cell culture broth, followed by depth filtration. The cell harvest step is usually followed by a Protein A affinity purification step, which is followed by virus inactivation. Virus inactivation is typically followed by one or more chromatographic steps, also referred to as polishing steps, which usually include one or more of cation exchange chromatography and/or anion exchange chromatography and/or hydrophobic interaction chromatography and/or mixed mode chromatography and/or hydroxyapatite chromatography. The polishing steps are followed by virus filtration and ultrafiltration/diafiltration, which completes the templated process. See, e.g., Shukla et al., J. Chromatography B., 848 (2007) 28-39; Liu et al., MAbs, 2010: Sep.-Oct. 2(5): 480-499.

Generally, the effluent of the filtration operations and the eluate of the chromatographic operations are collected in intermediate pool tanks and stored, often overnight, until the next unit operation. The time needed to complete this process may be as long as 4-7 days.

The present invention provides improved templated processes which overcome several of the shortcomings of the templated processes currently being used by the industry.

SUMMARY OF THE INVENTION

The present invention provides processes and systems which provide several advantages over the typical templated processes used in the industry today. The templated processes and systems described herein include unit operations that are connected in a continuous or semi-continuous manner and obviate the need for pool tanks (also called holding tanks) between certain unit operations, where holding tanks are typically used. Alternatively, only surge tanks are employed.

Due to a specific combination of certain process steps, the processes and systems described herein require fewer steps than typical processes used in the industry and also significantly reduce the time for the overall purification process, without having an adverse impact on the product yield.

In one aspect according to the present invention, processes for purifying a target molecule from a sample are provided. In some embodiments, such a process comprises the steps of: (a) providing a sample comprising the target molecule and one or more impurities; (b) adding at least one precipitant to the sample and removing one or more impurities, thereby to recover a clarified sample; (c) subjecting the clarified sample from step (b) to a bind and elute chromatography step comprising at least two separation units, with each separation unit comprising the same media, thereby to obtain an eluate comprising the target molecule; and (d) subjecting the eluate to flow-through purification comprising use of two or more media; where at least two steps are performed concurrently for at least a duration of their portion, and wherein the process comprises a single bind and elute chromatography step.

In some embodiments, the flow of liquid through the process is continuous, i.e., the process is a continuous process.

In some embodiments, the process comprises a virus inactivation step between steps (c) and (d) above. As described herein, the virus inactivation step comprises use of a virus inactivation agent selected from an acid, a detergent, a solvent and temperature change.

In some embodiments, the virus inactivation step employs the use of one or more in-line static mixers. In other embodiments, the virus inactivation step comprises the use of one or more surge tanks.

In some embodiments, the target molecule is an antibody, e.g., a monoclonal antibody or a polyclonal antibody.

In some embodiments, the precipitant employed in the processes described herein is a stimulus responsive polymer. A preferred stimulus responsive polymer is a modified polyallylamine polymer, which is responsive to a phosphate stimulus.

Other exemplary precipitants include, but are not limited to, e.g., an acid, caprylic acid, a flocculant and a salt.

In some embodiments, the removal of impurities following addition of a precipitant employs the use of one or more depth filter. In other embodiments, the removal of one or more impurities employs the use of centrifugation.

Following precipitation and removal of one or more impurities, the clarified sample is subjected to a single bind and elute chromatography step, e.g., step (c) mentioned above, which typically employs at least two separation units. In some embodiments, the bind and elute chromatography step employs continuous multi-column chromatography (CMC).

In a preferred embodiment, the bind and elute chromatography step is an affinity chromatography step (e.g., Protein A affinity chromatography). In other embodiments, the bind and elute chromatography step comprises the use of a cation exchange (CEX) bind and elute chromatography step or a mixed mode chromatography step.

In some embodiments, the bind and elute chromatography step (e.g., Protein A affinity chromatography) employs the use of an additive in the loading step, thereby resulting in reducing or eliminating the number of intermediate wash steps that are used.

Exemplary additives include salts, detergents, surfactants and polymers. In some embodiments, an additive is a salt (e.g., 0.5M NaCl)

In some embodiments, the starting sample is a cell culture. Such a sample may be provided in a bioreactor.

In some embodiments, the sample is provided in a vessel other than a bioreactor, e.g., it may be transferred to another vessel from a bioreactor before subjecting it to the purification process, as described herein.

In some embodiments, a precipitant used in step (b) above is added directly to a bioreactor containing a cell culture. In other embodiments, the precipitant is added to a vessel other than a bioreactor, where the vessel contains a sample comprising a target molecule. In some embodiments, the precipitant is added using a static mixer.

In some preferred embodiments, the processes described herein include a flow-through purification process operation, which employs two or more media selected from activated carbon, anion exchange chromatography media and cation exchange chromatography media. In some embodiments, such a flow-through purification operation additionally includes a virus filtration step, which employs the use of a virus filtration membrane.

The processes described herein obviate the need to use a pool tank between various process steps. In some embodiments, a process according to the present invention comprises the use of one or more surge tanks.

The processes described herein may additionally include a formulation step. In some embodiments, such a formulation step comprises diafiltration, concentration and sterile.

As stated above, the processes described herein include a flow-through purification operation, which typically employs two or more media. In some embodiments, a flow-through purification process operation used in the processes described herein comprises the following steps, where all steps are performed in a flow-through mode: (a) contacting the eluate from a Protein A chromatography column with activated carbon; (b) contacting the flow-through sample from step (a) with an anion exchange chromatography media; (c) contacting the flow-through sample from step (b) with a cation exchange chromatography media; and (d) obtaining the flow-through sample from step (c) comprising the target molecule, where the level of one or more impurities in the flow-through sample after step (d) is lower than the level in the eluate in step (a). The steps (a)-(c) described above may be performed in any order.

In some embodiments, the flow-through purification step further comprises a virus-filtration step, where the flow-through sample from step (c) directly flows into a virus filtration step.

In some embodiments, a solution change is required between steps (b) and steps (c), where the solution change employs the use of an in-line static mixer and/or a surge tank, to change the pH.

In some embodiments, the entire flow-through purification operation employs a single skid.

In some embodiments, the eluate from a Protein A chromatography step is subjected to a virus inactivation step prior to contacting the eluate with activated carbon.

In a particular embodiment described herein, a process for purifying a target molecule from a sample is provided, where the process comprises the steps of: (a) providing a bioreactor comprising a cell culture; (b) adding a precipitant to the bioreactor and removing one or more impurities, thereby resulting in a clarified sample; (c) subjecting the clarified sample to a Protein A affinity chromatography step, which employs at least two separation units, thereby to obtain an eluate; (d) subjecting the eluate from step (c) to a virus inactivating agent using an in-line static mixer or a surge tank; (e) contacting the eluate after virus inactivation to a flow-through purification operation comprising contacting the eluate in flow-through mode with activated carbon followed by an anion exchange chromatography media followed by an in-line static mixer and/or a surge tank to change pH followed by a cation exchange chromatography media followed by a virus filtration media; and (f) formulating the flow-through sample from step (d) at a desired concentration in a desired buffer, where the process steps are connected to be in fluid communication with each other, such that a sample can flow continuously from one process step to the next, and where at least two process steps (b)-(f) are performed concurrently during at least a portion of their duration.

In some embodiments described herein, a process for purifying a target molecule from a sample is provided, where the process comprises the steps of: (a) providing a bioreactor comprising a cell culture; (b) adding a precipitant to the bioreactor and removing one or more impurities, thereby resulting in a clarified sample; (c) adding one or more additives selected from the group consisting of a salt, a detergent, a surfactant and a polymer to the clarified sample; (d) subjecting the clarified sample to a Protein A affinity chromatography step, which employs at least two separation units, thereby to obtain an eluate; (e) subjecting the eluate from step (d) to a virus inactivating agent using an in-line static mixer or a surge tank; (f) contacting the eluate after virus inactivation to a flow-through purification operation comprising contacting the eluate in flow-through mode with activated carbon followed by an anion exchange chromatography media followed by an in-line static mixer and/or a surge tank to change pH followed by a cation exchange chromatography media followed by a virus filtration media; and (g) formulating the flow-through sample from step (f) at a desired concentration in a desired buffer, where the process steps are connected to be in fluid communication with each other, such that a sample can flow continuously from one process step to the next, and where at least two process steps (b)-(g) are performed concurrently during at least a portion of their duration.

In some embodiments, the additive in step (c) is 0.5M NaCl.

Also provided herein are systems for use in a purification process, as described herein. In some embodiments, a system includes: (a) a bioreactor; (b) a filtration device comprising one or more depth filters; (c) one bind and elute chromatography apparatus; and (d) a flow-through purification system comprising at least a flow-through anion exchange device, where a liquid flows continuously through the devices in (a)-(d) during a process run, where the devices are connected to be in fluid communication with each other.

In some embodiments, there is a connecting line between the various devices in the system. The devices are connected in line such that each device in the system is in fluid communication with devices that precede and follow the device in the system.

In some embodiments, the bioreactor used in a system according to the present invention is a disposable or a single use bioreactor.

In some embodiments, the system is enclosed in a sterile environment.

In some embodiments, the bind and elute chromatography apparatus includes at least two separation units, with each unit comprising the same chromatography media, e.g., Protein A affinity media. In a particular embodiment, the Protein A media comprises a Protein A ligand coupled to a rigid hydrophilic polyvinylether polymer matrix. In other embodiments, the Protein A ligand is coupled to agarose or controlled pore glass. The Protein A ligand may be based on a naturally occurring domain of Protein A from *Staphylococcus aureus* or be a variant or a fragment of a naturally occurring domain. In a particular embodiment, the Protein A ligand is derived from the C domain of *Staphylococcus aureus* Protein A.

In other embodiments, the bind and elute chromatography apparatus includes at least three separation units. The separation units are connected to be in fluid communication with each other, such that a liquid can flow from one separation unit to the next.

In yet other embodiments, the bind and elute chromatography step employs an additive in the clarified cell culture during the loading step where the inclusion of an additive reduces or eliminates the need for one or more wash steps before the elution step.

In some embodiments, a flow-through purification system additionally comprises an activated carbon device and a cation exchange (CEX) flow-through chromatography device. In some embodiments, the flow-through purification system further comprises a virus filtration device.

In some embodiments, the entire flow-through purification system employs a single skid.

DETAILED DESCRIPTION OF THE INVENTION

Figure 1:
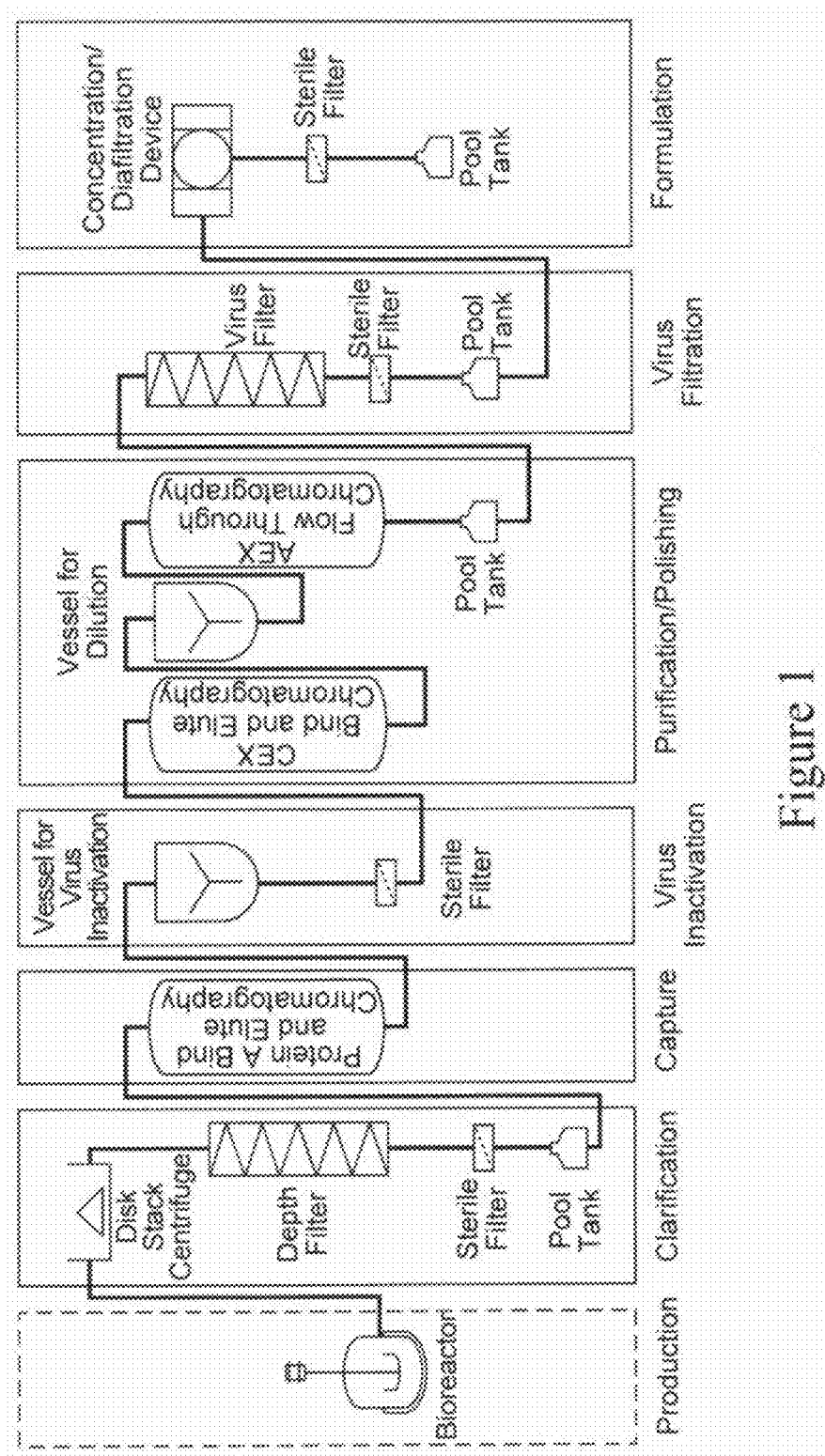
FIG. 1 is a schematic representation of a conventional purification process used in the industry.

The present invention provides processes and systems which overcome several shortcomings associated with the typical templated processes used in the industry for purification or biological molecules such as antibodies.

As discussed above, typical templated processes for purification of biological molecules include many different steps, including one or more chromatographic steps, require use of holding or pool tanks between steps as well as take several hours to days to complete.

There have been a few efforts to move away from a typical templated process. For example, PCT Patent Publication No. WO 2012/014183 discusses methods for protein purification in which two or more chromatographic separation modes are combined in tandem. Additionally, U.S. Patent Publication No. 2008/0269468 discusses combining a continuous perfusion fermentation system with a continuous particle removal system and a continuous purification system, where the flow rate of the mixture through the whole process is kept substantially constant.

Further, PCT Publication No. WO2012/051147 discusses processes for protein purification but does not appear to describe a continuous or a semi-continuous process.

Lastly, PCT Publication No. WO2012/078677 describes a continuous process for manufacture of biological molecules; however, appears to rely on the utilization of multi-valve arrays. Further, the aforementioned PCT publication also does not teach or suggest use of all the process steps described herein. For example, there appears to be no teaching or suggestion of a flow-through purification operation which includes multiple flow-through steps including, e.g., use of a flow-through activated carbon device, a flow-through AEX media, a flow-through CEX media and a flow-through virus filter. In fact, PCT Publication No. WO2012/078677 does not teach or suggest a cation exchange chromatography step performed in a flow-through mode. Lastly, the aforementioned PCT also fails to describe a continuous process that uses a single bind and elute chromatography step and can be performed successfully with minimum interventions, as per the processes described herein.

Therefore, although it appears desirable to have a purification process which is performed in a continuous mode, it has been difficult to achieve an efficient continuous process due to the complexity associated with connecting several individual unit operations to run in a continuous or even a semi-continuous mode with minimum interventions, e.g., fewer solution adjustments (e.g., changes in pH and/or conductivity). The present invention, however, has been able to achieve exactly that.

The present invention also provides other advantages over conventional processes used in the industry today, e.g., reducing the number of process steps as well as obviating the need to use large pool tanks between process steps for solution adjustments. In case of the processes and systems described herein, it is not required to perform large volume dilutions in order to change conductivity, thereby obviating the need to use large pool tanks between process steps. Additionally, in some embodiments, the processes and systems described herein employ fewer control/monitoring equipments (also called "skids"), which are typically associated with every single process step, compared to conventional processes used in the art.

In some embodiments, the present invention also provides processes which employ the inclusion of an additive during the loading step of Protein A chromatography, resulting in the reduction in or elimination of one or more intermediate wash steps by going straight from the loading step to the elution step or by reducing the number of wash steps between the loading step and the elution step, without sacrificing product purity. While U.S. Patent Publication No. 20130096284 discusses inclusion of an amino acid or salt in the sample being loaded onto a Protein A chromatography column, the foregoing publication does not appear to teach or suggest the use of such a Protein A chromatography step in a multi-column continuous or a semi-continuous mode, as described herein. Instead, it discusses the Protein A step to be performed in a batch, single column mode.

The present invention demonstrates that even upon the elimination of or reduction in the number of wash steps performed during the Protein A chromatography step, a reduction in the level of impurities, e.g., HCPs, is observed, without sacrificing product purity.

In order that the present invention may be more readily understood, certain terms are first defined. Additional definitions are set forth throughout the detailed description.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related.

The following terms are defined for purposes of the invention as described herein.

As used herein the term "target molecule" or "target compound" refers to any molecule, substance or compound or mixtures thereof that is isolated, separated or purified from one or more impurities in a sample using processes and systems described herein. In various embodiments, the target molecule is a biological molecule such as, e.g., a protein or a mixture of two or more proteins. In a particular embodiment, the target molecule is an Fc-region containing protein such as an antibody.

The term "antibody" refers to a protein which has the ability to specifically bind to an antigen. Typically, antibodies have a basic four-polypeptide chain structure consisting of two heavy and two light chains, said chains being stabilized, for example, by interchain disulfide bonds. Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments.

In some embodiments, an Fc-region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD1 Ia, CD1 Ib, CD1 Ic, CD 18, an ICAM, VLA-4 and VCAM; a tumor associated antigen such as HER2, HER3 or HER4 receptor; and fragments and/or variants of any of the above-listed polypeptides. In addition, an antibody that may be purified using the processes described herein may bind specifically to any of the above-listed polypeptides.

As used herein, and unless stated otherwise, the term "sample" refers to any composition or mixture that contains a target molecule. Samples may be derived from biological or other sources. Biological sources include eukaryotic and prokaryotic sources, such as plant and animal cells, tissues and organs. The sample may also include diluents, buffers, detergents, and contaminating species, debris and the like that are found mixed with the target molecule. The sample may be "partially purified" (i.e., having been subjected to one or more purification steps, such as filtration steps) or may be obtained directly from a host cell or organism producing the target molecule (e.g., the sample may comprise harvested cell culture fluid). In some embodiments, a sample is a cell culture feed.

The term "impurity" or "contaminant" as used herein, refers to any foreign or objectionable molecule, including a biological macromolecule such as DNA, RNA, one or more host cell proteins, endotoxins, lipids and one or more additives which may be present in a sample containing the target molecule that is being separated from one or more of the foreign or objectionable molecules using a process of the present invention. Additionally, such impurity may include any reagent which is used in a step which may occur prior to the method of the invention. An impurity may be soluble or insoluble in nature.

The term "insoluble impurity," as used herein, refers to any undesirable or objectionable entity present in a sample containing a target molecule, where the entity is a suspended particle or a solid. Exemplary insoluble impurities include whole cells, cell fragments and cell debris.

The term "soluble impurity," as used herein, refers to any undesirable or objectionable entity present in a sample containing a target molecule, where the entity is not an insoluble impurity. Exemplary soluble impurities include host cell proteins (HCPs), DNA, RNA, viruses, endotoxins, cell culture media components, lipids etc.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a target molecule such as an antibody or immunoadhesin expressed in a CHO cell). The amount of CHOP present in a mixture comprising a target molecule provides a measure of the degree of purity for the target molecule. HCP or CHOP includes, but is not limited to, a protein of interest expressed by the host cell, such as a CHO host cell. Typically, the amount of CHOP in a protein mixture is expressed in parts per million relative to the amount of the target molecule in the mixture. It is understood that where the host cell is another cell type, e.g., a mammalian cell besides CHO, E. coli, yeast, an insect cell, or a plant cell, HCP refers to the proteins, other than target protein, found in a lysate of that host cell.

The term "parts per million" or "ppm" are used interchangeably herein to refer to a measure of purity of a target molecule purified using a process described herein. The units ppm refer to the amount of HCP or CHOP in nanograms/milligram per target molecule in milligrams/milliliter (i.e., (CHOP ng/mL)/(target molecule mg/mL), where the target molecule and the HCPs are in solution).

The terms "purifying," "purification," "separate," "separating," "separation," "isolate," "isolating," or "isolation," as used herein, refer to increasing the degree of purity of a target molecule from a sample comprising the target molecule and one or more impurities. Typically, the degree of purity of the target molecule is increased by removing (completely or partially) at least one impurity from the sample.

The terms "bind and elute mode" and "bind and elute process," as used herein, refer to a separation technique in which at least one target molecule contained in a sample (e.g., an Fc region containing protein) binds to a suitable resin or media (e.g., an affinity chromatography media or a cation exchange chromatography media) and is subsequently eluted.

The terms "flow-through process," "flow-through mode," and "flow-through operation," as used interchangeably herein, refer to a separation technique in which at least one target molecule (e.g., an Fc-region containing protein or an antibody) contained in a biopharmaceutical preparation along with one or more impurities is intended to flow through a material, which usually binds the one or more impurities, where the target molecule usually does not bind (i.e., flows through).

The term "process step" or "unit operation," as used interchangeably herein, refers to the use of one or more methods or devices to achieve a certain result in a purification process. Examples of process steps or unit operations which may be employed in the processes and systems described herein include, but are not limited to, clarification, bind and elute chromatography, virus inactivation, flow-through purification (including use of two or more media selected from activated carbon, anion exchange and cation exchange in a flow-through mode) and formulation. It is understood that each of the process steps or unit operations may employ more than one step or method or device to achieve the intended result of that process step or unit operation. For example, in some embodiments, the clarification step and/or the flow-through purification operation, as described herein, may employ more than one step or method or device to achieve that process step or unit operation. In some embodiments, one or more devices which are used to perform a process step or unit operation are single-use devices and can be removed and/or replaced without having to replace any other devices in the process or even having to stop a process run.

As used herein, the term "system" generally refers to the physical form of the whole purification process, which includes two or more devices to perform the process steps or unit operations, as described herein. In some embodiments, the system is enclosed in a sterile environment.

As used herein, the term "separation unit" refers to an equipment or apparatus, which can be used in a bind and elute chromatographic separation or a flow-through step or a filtration step. For example, a separation unit can be a chromatography column or a chromatography cartridge which is filled with a sorbent matrix or a chromatographic device that contains a media that has appropriate functionality. In some embodiments according to the processes and systems described herein, a single bind and elute chromatography step is used in the purification process which employs two or more separation units. In a preferred embodiment, the two or more separation units include the same media.

In various embodiments, the processes and systems described herein obviate the need to necessarily use pool tanks, thereby significantly reducing the overall time to run a purification process as well as the overall physical footprint occupied by the system. Accordingly, in various embodiments according to the present invention, the output from one process step (or unit operation) is the input for the next step (or unit operation) in the process and flows directly and continuously into the next process step (or unit operation), without the need for collecting the entire output from a process step.

As used herein, the term "pool tank" refers to any container, vessel, reservoir, tank or bag, which is generally used between process steps and has a size/volume to enable collection of the entire volume of output from a process step. Pool tanks may be used for holding or storing or manipulating solution conditions of the entire volume of output from a process step. In various embodiments according to the present invention, the processes and systems described herein obviate the need to use one or more pool tanks.

In some embodiments, the processes and systems described herein may use one or more surge tanks throughout a purification process.

The term "surge tank" as used herein refers to any container or vessel or bag, which is used between process steps or within a process step (e.g., when a single process operation comprises more than one step); where the output from one step flows through the surge tank onto the next step. Accordingly, a surge tank is different from a pool tank, in that it is not intended to hold or collect the entire volume of output from a step; but instead enables continuous flow of output from one step to the next. In some embodiments, the volume of a surge tank used between two process steps or within a process operation (e.g., flow-through purification operation) described herein, is no more than 25% of the entire volume of the output from the process step. In another embodiment, the volume of a surge tank is no more than 10% of the entire volume of the output from a process step. In some other embodiments, the volume of a surge tank is less than 35%, or less than 30%, or less than 25%, or less than 20%, or less than 15%, or less than 10% of the entire volume of a cell culture in a bioreactor, which constitutes the starting material from which a target molecule is purified.

The term "continuous process," as used herein, refers to a process for purifying a target molecule, which includes two or more process steps (or unit operations), such that the output from one process step flows directly into the next process step in the process, without interruption and/or without the need to collect the entire volume of the output from a process step before performing the next process step. In a preferred embodiment, two or more process steps can be performed concurrently for at least a portion of their duration. In other words, in case of a continuous process, as described herein, it is not necessary to complete a process step before the next process step is started, but a portion of the sample is always moving through the process steps. The term "continuous process" also applies to steps within a process operation, in which case, during the performance of a process operation including multiple steps, the sample flows continuously through the multiple steps that are necessary to perform the process operation. One example of such a process operation described herein is the flow through purification operation which includes multiple steps that are performed in a continuous manner and employs two or more of flow-through activated carbon, flow-through AEX'media, flow-through CEX media, and flow-through virus filtration. In one embodiment, the flow through purification operation is carried out in the order: activated carbon followed by AEX media followed by CEX media followed by virus filtration. However, it is understood that activated carbon, AEX media and CEX media may be used in any order.

Accordingly, in some embodiments, AEX is followed by activated carbon followed by CEX media; or alternatively, CEX is followed by activated carbon followed by AEX media. In yet other embodiments, activated carbon is followed by CEX media followed by AEX media. In still other embodiments, AEX media is followed by CEX media followed by activated carbon; or alternatively, CEX media is followed by AEX media followed by activated carbon.

Continuous processes, as described herein, also include processes where the input of the fluid material in any single process step or the output is discontinuous or intermittent. Such processes may also be referred to as "semi-continuous" processes. For example, in some embodiments according to the present invention, the input in a process step (e.g., a bind and elute chromatography step) may be loaded continuously; however, the output may be collected intermittently, where the other process steps in the purification process are continuous. Accordingly, in some embodiments, the processes and systems described herein include at least one unit operation which is operated in an intermittent matter, whereas the other unit operations in the process or system may be operated in a continuous manner.

The term "connected process" refers to a process for purifying a target molecule, where the process comprises two or more process steps (or unit operations), which are connected to be in direct fluid communication with each other, such that fluid material continuously flows through the process steps in the process and is in simultaneous contact with two or more process steps during the normal operation of the process. It is understood that at times, at least one process step in the process may be temporarily isolated from the other process steps by a barrier such as a valve in the closed position. This temporary isolation of individual process steps may be necessary, for example, during start up or shut down of the process or during removal/replacement of individual unit operations. The term "connected process" also applies to steps within a process operation which are connected to be in fluid communication with each other, e.g., when a process operation requires several steps to be performed in order to achieve the intended result of the operation (e.g., the flow-through purification operation used in the methods described herein).

The term "fluid communication," as used herein, refers to the flow of fluid material between two process steps or flow of fluid material between process steps of a process operation, where the process steps are connected by any suitable means (e.g., a connecting line or surge tank), thereby to enable the flow of fluid from one process step to another process step. In some embodiments, a connecting line between two unit operations may be interrupted by one or more valves to control the flow of fluid through the connecting line. A connecting line may be in the form of a tube, a hose, a pipe, a channel or some other means that enables flow of liquid between two process steps.

The terms "clarify," "clarification," and "clarification step," as used herein, refers to a process step for removing suspended particles and or colloids, thereby to reduce turbidity, of a target molecule containing solution, as measured in NTU (nephelometric turbidity units). Clarification can be achieved by a variety of means, including centrifugation or filtration. Centrifugation could be done in a batch or continuous mode, while filtration could be done in a normal flow (e.g. depth filtration) or tangential flow mode. In processes used in the industry today, centrifugation is typically followed by depth filtration intended to remove insoluble impurities, which may not have been removed by centrifugation. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation. In some embodiments, the processes and systems described herein obviate the need for centrifugation.

The term "precipitate," precipitating" or "precipitation" as used herein, refers to process used in clarification, in which the properties of the undesirable impurities are modified such that they can be more easily separated from the soluble target molecule. This is typically accomplished by forming large aggregate particles and/or insoluble complexes containing the undesirable impurities. These particles have properties (e.g. density or size) such that they can be more easily separated from the liquid phase that contains the soluble target molecule, such as by filtration or centrifugation. In some cases, a phase change is caused, such that the undesirable impurities can be more easily separated from the soluble target molecule. Precipitation by phase change can be achieved by the addition of a precipitating agent, such as a polymer or a small molecule. In a particular embodiment, the precipitant is a stimulus responsive polymer, also referred to as a smart polymer. In some embodiments described herein, the precipitant or precipitating agent is a flocculant. Flocculation, as used herein, is one way of performing precipitation where the performance typically depends on the flocculant concentration used ("dose dependent"). Typical flocculating agents are polyelectrolytes, such as polycations, that complex with oppositely charged impurities.

In some embodiments described herein, clarification employs the addition of a precipitant to a sample containing a target molecule and one or more impurities. In some cases, a change in solution conditions (such as temperature, pH, salinity) may be used to initiate the precipitation, such as in the case of stimulus responsive polymers. The precipitated material which contains the one or more impurities as well as the precipitating agent is subsequently removed thereby recovering the target molecule in the liquid phase, where the liquid is then typically subjected to further process steps in order to further purify the target molecule.

Precipitation may be performed directly in a bioreactor containing a cell culture expressing a target molecule to be purified, where a precipitant is added directly to the bioreactor. Alternatively, the precipitant may be added to the cell culture, which typically contains the target molecule, in a separate vessel.

In some embodiments, the precipitant is added using a static mixer. In case the precipitant is a stimulus responsive polymer, both the polymer and the stimulus to which it is responsive, may be added using a static mixer.

There are many ways known to those skilled in the art of removing the precipitated material, such as centrifugation, filtration or settling or any combinations thereof.

The term "settling," as used herein, refers to a sedimentation process in which the precipitated material migrates to the bottom of a vessel under the influence of gravitational forces. Settling can be followed by decanting or filtering of the liquid phase or supernatant.

The term "stimulus" or "stimuli," as used interchangeably herein, is meant to refer to a physical or chemical change in the environment which results in a response by a stimulus responsive polymer. Accordingly, such polymers are responsive to a stimulus and the stimulus results in a change in the solubility of the polymer. Examples of stimuli to which one or more polymers used herein are responsive, include, but are not limited to, e.g., changes in temperature, changes in conductivity and/or changes in pH. In some embodiments, a stimulus comprises addition of a complexing agent or a complex forming salt to a sample. In various embodiments, a stimulus is generally added after the addition of a polymer to a sample. Although, the stimulus may also be added during or before addition of a polymer to a sample.

The term "stimulus responsive polymer," as used herein, refers to a polymer or copolymer which exhibits a change in a physical and/or chemical property after the addition of a stimulus. A typical stimulus response is a change in the polymer's solubility. For example, the polymer poly(N-isopropylacrylamide) is water soluble at temperatures below about 35° C., but become insoluble in water at temperatures of about 35° C. In a particular embodiment, a stimulus responsive polymer is a modified polyallylamine (PAA) polymer which is responsive to a multivalent ion stimulus (e.g, phosphate stimulus). Further details regarding this polymer can be found, e.g., in U.S. Publication No. 20110313066, incorporated by reference herein in its entirety.

In some embodiments, a cell culture is subjected to a depth filter to remove one or more impurities.

The terms "depth filter" or "depth filtration" as used herein refer to a filter that is capable of retaining particulate matter throughout the filter medium, rather than just on the filter surface. In some embodiments described herein, one or more depth filters are used in the clarification process step.

In some embodiments, clarification results in the removal of soluble and/or insoluble impurities in a sample which may later on result in the fouling of a filter or device used in a process step in a purification process, thereby making the overall purification process more economical.

In various embodiments described herein, one or more chromatography steps are included in a protein purification process.

The term "chromatography" refers to any kind of technique which separates an analyte of interest (e.g. a target molecule) from other molecules present in a mixture through differential adsorption onto a media. Usually, the target molecule is separated from other molecules as a result of differences in rates at which the individual molecules of the mixture migrate through a stationary medium under the influence of a moving phase, or in bind and elute processes.

The term "matrix," as used herein, refers to any kind of particulate sorbent, bead, resin or other solid phase (e.g., a membrane, non-woven, monolith, etc.) which usually has a functional group or ligand attached to it. A matrix having a ligand or functional group attached to it is referred to as "media," which in a separation process, acts as the adsorbent to separate a target molecule (e.g., an Fc region containing protein such as an immunoglobulin) from other molecules present in a mixture (e.g., one or more impurities), or alternatively, acts as a sieve to separate molecules based on size (e.g., in case of a virus filtration membrane).

Examples of materials for forming the matrix include polysaccharides (such as agarose and cellulose); and other mechanically stable substances such as silica (e.g. controlled pore glass), poly(styrenedivinyl)benzene, polyacrylamide, ceramic particles and derivatives of any of the above. In a particular embodiment, a rigid hydrophilic polyvinylether polymer is used as a matrix.

Certain media may not contain ligands. Examples of media that may be used in the processes described herein that do not contain a ligand include, but are not limited to, activated carbon, hydroxyapatite, silica, etc.

The term "ligand," as used herein, refers to a functional group that is attached to a matrix and that determines the binding properties of the media. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Other exemplary ligands which may be used include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as $N_5N$ diethylamino or DEAE; hydrophobic interaction groups, such as phenyl, butyl, propyl, hexyl; and affinity groups, such as Protein A, Protein G, and Protein L. In a particular embodiment, the ligand that is used in the processes and systems described herein includes one or more Protein A domains or a functional variant or fragment thereof, as described in U.S. Patent Publication Nos. 201002218442 and 20130046056, both incorporated by reference herein, which relate to ligands based either on wild-type multimeric forms of B, Z or C domains or on multimeric variants of Protein A domains (e.g., B, Z or C domain pentamers). The ligands described therein also exhibit reduced Fab binding.

The term "affinity chromatography" refers to a protein separation technique in which a target molecule (e.g., an Fc region containing protein of interest or antibody) specifically binds to a ligand which is specific for the target molecule. Such a ligand is generally covalently attached to a suitable chromatography matrix material and is accessible to the target molecule in solution as the solution contacts the chromatography media. In a particular embodiment, the ligand is Protein A or a functional variant thereof, immobilized onto a rigid hydrophilic polyvinylether polymer matrix. The target molecule generally retains its specific binding affinity for the ligand during the chromatographic steps, while other solutes and/or proteins in the mixture do not bind appreciably or specifically to the ligand. Binding of the target molecule to the immobilized ligand allows contaminating proteins and impurities to be passed through the chromatography matrix while the target molecule remains specifically bound to the immobilized ligand on the solid phase material. The specifically bound target molecule is then removed in its active form from the immobilized ligand under suitable conditions (e.g., low pH, high pH, high salt, competing ligand etc.), and passed through the chromatographic column with the elution buffer, substantially free of the contaminating proteins and impurities that were earlier allowed to pass through the column. It is understood that any suitable ligand may be used for purifying its respective specific binding protein, e.g. an antibody.

In some embodiments according to the present invention, Protein A is used as a ligand for purifying an Fc region containing target protein. The conditions for elution from the ligand (e.g., based on Protein A) of the target molecule (e.g., an Fc-region containing protein) can be readily determined by one of ordinary skill in the art. In some embodiments, Protein G or Protein L or a functional variant thereof may be used as a ligand. In some embodiments, a process which employs a ligand such as Protein A, uses a pH range of 5-9 for binding to an Fc-region containing protein, followed by washing or re-equilibrating the ligand/target molecule conjugate, which is then followed by elution with a buffer having pH about or below 4 which contains at least one salt.

The terms "Protein A" and "Prot A" are used interchangeably herein and encompasses Protein A recovered from a native source thereof, Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen, GE or Fermatech. Protein A is generally immobilized on a chromatography matrix. A functional derivative, fragment or variant of Protein A used in the methods and systems according to the present invention may be characterized by a binding constant of at least $K=10^8$ M, and preferably $K=10^9$ M, for the Fc region of mouse IgG2a or human IgG1. An interaction compliant with such value for the binding constant is termed "high affinity binding" in the present context. In some embodiments, such functional derivatives or variants of Protein A comprise at least part of a functional IgG binding domain of wild-type Protein A, selected from the natural domains E, D, A, B, C or engineered mutants thereof, which have retained IgG binding functionality.

Also, Protein A derivatives or variants engineered to allow a single-point attachment to a solid support may also be used in the affinity chromatography step in the claimed methods.

Single point attachment generally means that the protein moiety is attached via a single covalent bond to a chromatographic support material of the Protein A affinity chromatography. Such single-point attachment may also occur by use of suitably reactive residues which are placed at an exposed amino acid position, namely in a loop, close to the N- or C-terminus or elsewhere on the outer circumference of the protein fold. Suitable reactive groups are e.g. sulthydryl or amino functions.

In some embodiments, Protein A derivatives of variants are attached via multi-point attachment to suitable a chromatography matrix.

The term "affinity chromatography matrix," as used herein, refers to a chromatography matrix which carries ligands suitable for affinity chromatography. Typically the ligand (e.g., Protein A or a functional variant or fragment thereof) is covalently attached to a chromatography matrix material and is accessible to the target molecule in solution as the solution contacts the chromatography media. One example of an affinity chromatography media is a Protein A media. An affinity chromatography media typically binds the target molecules with high specificity based on a lock/key mechanism such as antigen/antibody or enzyme/receptor binding. Examples of affinity media carrying Protein A ligands include Protein A SEPHAROSE™ and PROSEP®-A. In the processes and systems described herein, an affinity chromatography step may be used as the single bind and elute chromatography step in the entire purification process. In a particular embodiment, a Protein A based ligand is attached to a rigid hydrophilic polyvinylether polymer matrix. In other embodiments, such a ligand is attached to agarose or to controlled pore glass.

The terms "ion-exchange" and "ion-exchange chromatography," as used herein, refer to the chromatographic process in which a solute or analyte of interest (e.g., a target molecule being purified) in a mixture, interacts with a charged compound linked (such as by covalent attachment) to a solid phase ion exchange material, such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest.

"Ion-exchange chromatography" specifically includes cation exchange, anion exchange, and mixed mode ion exchange chromatography. For example, cation exchange chromatography can bind the target molecule (e.g., an Fc region containing target protein) followed by elution (e.g., using cation exchange bind and elute chromatography or "CEX") or can predominately bind the impurities while the target molecule "flows through" the column (cation exchange flow through chromatography FT-CEX).

Anion exchange chromatography can bind the target molecule (e.g., an Fc region containing target protein) followed by elution or can predominately bind the impurities while the target molecule "flows through" the column, also referred to as negative chromatography. In some embodiments and as demonstrated in the Examples set forth herein, the anion exchange chromatography step is performed in a flow through mode.

The term "ion exchange media" refers to a media that is negatively charged (i.e., a cation exchange media) or positively charged (i.e., an anion exchange media). The charge may be provided by attaching one or more charged ligands to a matrix, e.g., by covalent linkage. Alternatively, or in addition, the charge may be an inherent property of the matrix (e.g., as is the case of silica, which has an overall negative charge).

The term "anion exchange media" is used herein to refer to a media which is positively charged, e.g. having one or more positively charged ligands, such as quaternary amino groups, attached to a matrix. Commercially available anion exchange media include DEAE cellulose, QAE SEPHADEX™ and FAST Q SEPHAROSE™ (GE Healthcare). Other exemplary materials that may be used in the processes and systems described herein are Fractogel® EMD TMAE, Fractogel® EMD TMAE highcap, Eshmuno® Q and Fractogel® EMD DEAE (EMD Millipore).

The term "cation exchange media" refers to a media which is negatively charged, and which has free cations for exchange with cations in an aqueous solution contacted with the solid phase of the media. A negatively charged ligand attached to the solid phase to form the cation exchange media may, for example, be a carboxylate or sulfonate. Commercially available cation exchange media include carboxy-methyl-cellulose, sulphopropyl (SP) immobilized on agarose (e.g., SP-SEPHAROSE FAST FLOW™ or SP-SEPHAROSE HIGH PERFORMANCE™, from GE Healthcare) and sulphonyl immobilized on agarose (e.g. S-SEPHAROSE FAST FLOW™ from GE Healthcare). Preferred is Fractogel® EMD SO$_3$, Fractogel® EMD SE Highcap, Eshmuno® S and Fractogel® EMD COO (EMD Millipore).

The term "mixed-mode chromatography" or "multimodal chromatography," as used herein, refers to a process employing a chromatography stationary phase that carries at least two distinct types of functional groups, each capable of interacting with a molecule of interest. Mixed-mode chromatography generally employs a ligand with more than one mode of interaction with a target protein and/or impurities. The ligand typically includes at least two different but co-operative sites which interact with the substance to be bound. For example, one of these sites may have a charge-type interaction with the substance of interest, whereas the other site may have an electron acceptor-donor type interaction and/or hydrophobic and/or hydrophilic interactions with the substance of interest. Electron donor-acceptor interaction types include hydrogen-bonding, π-π, cation-π, charge transfer, dipole-dipole and induced dipole interactions. Generally, based on the differences of the sum of interactions, a target protein and one or more impurities may be separated under a range of conditions.

The term "mixed mode ion exchange media" or "mixed mode media" refers to a media which is covalently modified with cationic and/or anionic and hydrophobic moieties. A commercially available mixed mode ion exchange media is BAKERBOND ABX™ (J. T. Baker, Phillipsburg, N.J.) containing weak cation exchange groups, a low concentration of anion exchange groups, and hydrophobic ligands attached to a silica gel solid phase support matrix. Mixed mode cation exchange materials typically have cation exchange and hydrophobic moieties. Suitable mixed mode cation exchange materials are Capto® MMC (GE Healthcare) and Eshmuno® HCX (EMD Millipore).

Mixed mode anion exchange materials typically have anion exchange and hydrophobic moieties. Suitable mixed mode anion exchange materials are Capto® Adhere (GE Healthcare).

The term "hydrophobic interaction chromatography" or "HIC," as used herein, refers to a process for separating molecules based on their hydrophobicity, i.e., their ability to adsorb to hydrophobic surfaces from aqueous solutions. HIC is usually differentiated from the Reverse Phase (RP) chromatography by specially designed HIC resins that typically have a lower hydrophobicity, or density of hydrophobic ligands compared to RP resins.

HIC chromatography typically relies on the differences in hydrophobic groups on the surface of solute molecules. These hydrophobic groups tend to bind to hydrophobic groups on the surface of an insoluble matrix. Because HIC employs a more polar, less denaturing environment than reversed phase liquid chromatography, it is becoming increasing popular for protein purification, often in combination with ion exchange or gel filtration chromatography.

The term "break-through," as used herein, refers to the point of time during the loading of a sample containing a target molecule onto a packed chromatography column or separation unit, when the target molecule first appears in the output from the column or separation unit. In other words, the term "break-through" is the point of time when loss of target molecule begins.

A "buffer" is a solution that resists changes in pH by the action of its acid-base conjugate components. Various buffers which can be employed depending, for example, on the desired pH of the buffer, are described in: Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

When "loading" a sample onto a device or a column or a separation unit containing a suitable media, a buffer is used to load the sample comprising the target molecule and one or more impurities onto the device or column or separation unit. In the bind and elute mode, the buffer has a conductivity and/or pH such that the target molecule is bound to media, while ideally all the impurities are not bound and flow through the column. Whereas, in a flow-through mode, a buffer is used to load the sample comprising the target molecule and one or more impurities onto a column or device or separation unit, wherein the buffer has a conductivity and/or pH such that the target molecule is not bound to the media and flows through while ideally all or most of the impurities bind to the media.

The term "additive" as used herein, refers to any agent which is added to a sample containing a target protein prior to loading of the sample onto a chromatography matrix or during the loading step, where the addition of the agent eliminates one or more wash steps or reduces the number of wash step which are otherwise designed for impurity removal, to be used subsequent to the loading step and before the elution of the target protein. A single agent may be added to a sample prior to or during the loading or the number of agents may be more than one. Exemplary additives include, but are not limited to, salts, polymers, surfactants or detergents, solvents, chaotropic agents and any combinations thereof. In a particular embodiment, such an additive is sodium chloride salt.

In a particular embodiment, a static mixer is used for contacting the output from the clarification step with an additive, where the use of a static mixer significantly reduces the time, thus allowing for a simplified connection of the clarification step to the protein A chromatography step.

The term "re-equilibrating" refers to the use of a buffer to re-condition the media prior to loading the target molecule. The same buffer used for loading may be used for re-equilibrating.

The term "wash" or "washing" a chromatography media refers to passing an appropriate liquid, e.g., a buffer, through or over the media. Typically washing is used to remove weakly bound contaminants from the media prior to eluting the target molecule and/or to remove non-bound or weakly bound target molecule after loading. In some embodiments, the wash buffer is different from the loading buffer. In other embodiments, the wash buffer and the loading buffer are the same. In a particular embodiment, a wash step is eliminated or the number of wash steps is reduced in a purification process by altering the conditions of the sample load.

In some embodiments, the wash steps that are used in the processes described herein employ a buffer having a conductivity of 20 mS/cm or less, and accordingly, are different from the buffers that are typically used for impurity removal, as those typically have a conductivity greater than 20 mS/cm.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSeimens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. In some embodiments, the salt concentration of the various buffers is modified to achieve the desired conductivity. In some embodiments, in processes where one or more additives are added to a sample load, if one or more wash steps are subsequently used, such wash steps employ a buffer with a conductivity of about 20 mS/cm or less.

The term "elute" or "eluting" or "elution" refers to removal of a molecule (e.g., a polypeptide of interest or an impurity) from a chromatography media by using or altering certain solution conditions, whereby the buffer (referred to as an "elution buffer") competes with the molecule of interest for the ligand sites on the chromatography resin. A non-limiting example is to elute a molecule from an ion exchange resin by altering the ionic strength of the buffer surrounding the ion exchange material such that the buffer competes with the molecule for the charged sites on the ion exchange material.

In some embodiments, the elution buffer has a low pH (e.g., having a pH in the range of about 2 to about 5, or from about 3 to about 4) and which disrupts the interactions between ligand (e.g., Protein A) and the target protein. Exemplary elution buffers include phosphate, acetate, citrate and ammonium buffers, as well as combinations of these. In some embodiments, an elution buffer may be used which has a high pH (e.g., pH of about 9 or higher). Elution buffers may also contain additional compounds, e.g., $MgCl_2$ (2 mM) for facilitating elution.

In case virus inactivation (VI) is desired, a virus inactivation buffer may be used to inactivate certain viruses prior to eluting the target molecule. In such instances, typically, the virus inactivation buffer differs from loading buffer since it may contain detergent/detergents or have different properties (pH/conductivity/salts and their amounts). In some embodiments, virus inactivation is performed before the bind and elute chromatography step. In some embodiments, virus inactivation is performed after during or after elution from a bind and elute chromatography step. In some embodiments, virus inactivation is performed in-line using a static mixer. In other embodiments, virus inactivation employs use of one or more surge tanks.

The term "bioreactor," as used herein, refers to any manufactured or engineered device or system that supports a biologically active environment. In some instances, a bioreactor is a vessel in which a cell culture process is carried out. Such a process may either be aerobic or anaerobic. Commonly used bioreactors are typically cylindrical, ranging in size from liters to cubic meters, and are often made of stainless steel. In some embodiments described herein, a bioreactor is made of a material other than steel and is disposable or single-use. It is contemplated that the total volume of a bioreactor may be any volume ranging from 100 mL to up to 10,000 Liters or more, depending on a particular process. In some embodiments according to the processes and systems described herein, the bioreactor is connected to a unit operation such as a depth filter. In some embodiments described herein, a bioreactor is used for both cell culturing as well as for precipitation, where a precipitant may be added directly to a bioreactor, thereby to precipitate one or more impurities.

The term "active carbon" or "activated carbon," as used interchangeably herein, refers to a carbonaceous material which has been subjected to a process to enhance its pore structure. Activated carbons are porous solids with very high surface areas. They can be derived from a variety of sources including coal, wood, coconut husk, nutshells, and peat. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface. In some embodiments described herein, activated carbon is used in a flow through purification step, which typically follows a bind and elute chromatography step or a virus inactivation step which in turn follows the bind and elute chromatography step. In some embodiments, activated carbon is incorporated within a cellulose media, e.g., in a column or some other suitable device.

The term "static mixer" refers to a device for mixing two fluid materials, typically liquids. The device generally consists of mixer elements contained in a cylindrical (tube) housing. The overall system design incorporates a method for delivering two streams of fluids into the static mixer. As the streams move through the mixer, the non-moving elements continuously blend the materials. Complete mixing depends on many variables including the properties of the fluids, inner diameter of the tube, number of mixer elements and their design etc. In some embodiments described herein, one or more static mixers are used throughout the purification process or system. In a particular embodiment, a static mixer is used for contacting the output from the bind and elute chromatography step with a virus inactivating agent (e.g., an acid or any other suitable virus inactivating agent), where the use of a static mixer significantly reduces the time, which would otherwise be needed to accomplish effective virus inactivation.

Processes According to the Present Invention

As discussed above, the present invention provides novel and improved processes for purification of target molecules from a sample (e.g., a cell culture feed) containing a target molecule and one or more impurities. The processes described herein are a vast improvement over existing methods used in the art, in that they reduce the overall time frame required for a process run (12-24 hours relative to several days); include fewer steps relative to most conventional processes; reduce the overall physical footprint of a process by virtue of having fewer unit operations and are easier to execute than a conventional process. Additionally, in some embodiments, processes according to the present invention employ devices that may be disposable.

The processes according to the present invention include several process steps or unit operations which are intended to achieve a desired result and where the process steps (or unit operations) are connected such that to be in fluid communication with each other and further that two or more process steps can be performed concurrently for at least a part of the duration of each process step. In other words, a user does not have to wait for a process step to be completed before executing the next process step in the process, but a user can start a process run such that the liquid sample containing the target molecule flows through the process steps continuously or semi-continuously, resulting in a purified target molecule. Accordingly, the sample containing the target molecule is typically in contact with more than one process step or unit operation in the process at any given time.

Each process step (or unit operation) may involve the use of one or more devices or methods to accomplish the process step.

The processes described herein are different from conventional processes used in the industry, in that they obviate the need to use pool tanks for holding, diluting, manipulating and sometimes storing the output from a process step before the output is subjected to the next process step. In contrast, the processes described herein enable any manipulation of the sample in-line (e.g., using a static mixer) or employ the use of surge tanks (which are usually not more than 10% or 20% or 25% of total volume of the output from a process step) between process steps or sometimes within a process operation (e.g., when a process operation employs more than one method or device), thereby significantly reducing the overall time to perform the process as well as the physical footprint of the overall system for performing the process. In a preferred embodiment, processes described herein use no pool tanks but only surge tanks having a volume of less than 25%, preferably less than 10% of the volume of the output from the preceding step.

The processes described herein include at least three process steps-clarification, bind and elute chromatography and flow-through purification. Typically, clarification is the first step followed by bind and elute chromatography followed by flow-through purification operation. The processes may include additional process steps including, but not limited to, virus inactivation and formulation. An important aspect of the processes described herein is that regardless of the number of steps, the process includes only one bind and elute chromatography step.

The various process steps are performed in a continuous or a semi-continuous manner, as described herein. Following are examples of process steps which may be used in a continuous or semi-continuous process, as described herein. It is understood that any combinations of the process steps shown, below can be used. In other words, any process step under Step 1 in the Table I below may be combined with any process step under Step 2 and/or any process step under Step 3 and so forth. It is also understood that additional process steps, which are described elsewhere in the specification may be combined with or used instead of one or more of the process steps described in Table I below.

TABLE I

| Step 1 | Step 2 | Step 3 | Step 4 | Step 5 |
| --- | --- | --- | --- | --- |
| Clarification | Bind and Elute Chromatography | Virus Inactivation | Flow-through purification | Formulation |
| Precipitation in a vessel followed by depth filtration | Continuous/semi-continuous bind and elute Protein A chromatography | Virus inactivation in a surge tank | Flow through AEX media with or without virus filtration | Diafiltration and concentration followed by sterile filtration |
| Precipitation in a vessel followed by centrifugation | Simulated moving bed bind and elute Protein A chromatography | Virus inactivation using a static mixer | Flow through AEX media and CEX media with or without virus filtration | Concentration followed by sterile filtration |
| Precipitation in a vessel followed by settling and microfiltration of the supernatant | Continuous/semi-continuous Cation exchange bind and elute chromatography | | Flow through activated carbon media and AEX media with or without virus filtration | Diafiltration followed by sterile filtration |
| Precipitation in a bioreactor followed by | Continuous/semi-continuous Mixed mode | | Flow through activated | |

TABLE I-continued

| Step 1 | Step 2 | Step 3 | Step 4 | Step 5 |
|---|---|---|---|---|
| depth filtration | bind and elute chromatography | | carbon media and AEX media and CEX media with or without virus filtration | |
| Precipitation in a bioreactor followed by centrifugation | | | | |
| Precipitation in a bioreactor followed by settling and microfiltration of the supernatant | | | | |

The various process steps (or unit operations) are described in more detail infra.

The starting material for the purification process is usually a sample containing a target molecule being purified. Typically, a cell culture producing the target molecule is used. However, samples other than cell cultures may also be used. Exemplary samples include, but are not limited to, transgenic mammalian cell cultures, non-transgenic mammalian cell cultures, bacterial cell cultures, tissue cultures, microbial fermentation batches, plant extracts, biofuels, seawater cultures, freshwater cultures, wastewater cultures, treated sewage, untreated sewage, milk, blood, and combinations thereof. Generally, the samples contain various impurities in addition to the target molecule. Such impurities include media components, cells, cell debris, nucleic acids, host cell proteins, viruses, endotoxins, etc.

Clarification

One of the first process steps (or unit operations) in the processes and systems described herein is typically clarification. Clarification is intended to separate one or more soluble and/or insoluble impurities from the target molecule. In some embodiments, insoluble impurities like cells and cellular debris are removed from the sample resulting in a clarified fluid containing the target molecule in solution as well as other soluble impurities. Clarification is typically performed prior to a step involving capture of the desired target molecule. Another key aspect of clarification is the removal of soluble and/or insoluble impurities in a sample which may later on result in the fouling of a sterile filter in a purification process, thereby making the overall purification process more economical.

As used in the industry today, clarification generally comprises removal of cells and/or cellular debris and typically involves centrifugation as the first step, followed by depth filtration. See, e.g., Shukla et al., J. Chromatography B, 848 (2007): 28-39; Liu et al., MAbs, 2(5): 480-499 (2010).

In some preferred embodiments described herein, clarification obviates the need to use centrifugation.

For example, in some embodiments, where the starting volume of the cell culture sample in a bioreactor is less than 2000 liters, or less than 1000 liters or less than 500 liters, the cell culture sample may be subjected to depth filtration alone or to settling and depth filtration, without the need for centrifugation.

In some preferred embodiments, use of precipitation before depth filtration increases throughput and therefore, the amount of sample volume which may be processed without the need for centrifugation is also increased. In other words, in some instances, if 1000 liters of a sample can be processed by depth filtration alone, by combining that with precipitation, a user may be able to process almost twice that amount, i.e., 2000 liters.

Depth filters are typically used to remove one or more insoluble impurities. Depth filters are filters that use a porous filtration medium to retain particles throughout the medium, rather than just on the surface of the medium.

In some preferred embodiments, a depth filter is used for clarification, which is capable of filtering cellular debris and particulate matter having a particle size distribution of about 0.5 µm to about 200 µm at a flow rate of about 10 liters/m$^2$/hr to about 100 liters/m$^2$/hr.

It has been found that especially good results in the primary removal of particulate impurities can be achieved if the porous depth filter is anisotropic (i.e. with a gradual reduction in pore size). In some preferred embodiments, the pores have a nominal pore size rating>about 25 µm. In some preferred embodiments, the depth filter comprises at least 2 graded layers of non-woven fibers, wherein the graded layers have a total thickness of about 0.3 cm to about 3 cm.

In some embodiments, the depth filters are configured in a device which is able to filter high solid feeds containing particles having a particle size distribution of approximately 0.5 µm to 200 µm at a flow rate of about 10 liters/m$^2$/hr to about 100 liters/m$^2$/hr until the transmembrane pressure (TMP) reaches 20 psi.

In some embodiments, depth filters comprise a composite of graded layers of non-woven fibers, cellulose, and diatomaceous earth. The non-woven fibers comprise polypropylene, polyethylene, polyester, nylon or mixtures thereof.

Exemplary depth filters and methods of use thereof may be found in U.S. Patent Publication No. 20130012689, incorporated by reference herein, which are particularly useful for filtering samples containing particles have a size distribution of about 0.5 µm to 200 µm. Accordingly, in some embodiments, depth filters used in the clarification step include open graded layers, allowing the larger particles in the feed stream to penetrate into the depth of the filter, and become captured within the pores of the filter rather than collect on the surface. The open top layers of the graded depth filters enable capturing of larger particles, while the bottom layers enable capturing the smaller residual aggregated particles. Various advantages of the graded depth filters include a higher throughput, retention of larger solids and eliminating the problem of cake formation.

As discussed above, in some embodiments, clarification includes the use of depth filtration following precipitation. Precipitation may employ acid precipitation, use of a stimulus responsive polymer, flocculation or settling and any other suitable means/agent for achieving precipitation. Accordingly, in some embodiments, a precipitant, e.g., a stimulus responsive polymer, is added to a sample to precipitate one or more soluble and/or insoluble impurities prior to depth filtration.

Other means of precipitation include, but are not limited to, use of short-chain fatty acids such as caprylic acid, use of flocculants, changing solution conditions (e.g., temperature, pH, salinity) and acid precipitation. For example, it has been reported that in mildly acidic conditions, the addition of short-chain fatty acids such as caprylic acid typically precipitates non IgG proteins while IgG is not precipitated.

Flocculation, as used herein, is one way of performing precipitation where the precipitation typically depends on the flocculant concentration used (i.e., is "dose dependent"). Typical flocculating agents are polyelectrolytes, such as polycations, that complex with oppositely charged impurities.

Flocculants generally precipitate cells, cell debris and proteins because of the interaction between the charges on the cells/proteins and charges on the polymer (e.g. polyelectrolytes), thereby creating insoluble complexes.

The use of polyelectrolyte polymers in flocculation to purify proteins is well established in the art (see, e.g., International PCT Patent Application No. WO2008/091740, incorporated by reference herein). Precipitation by flocculants can be accomplished with a wide range of polymers, with the only required general characteristic being the polymer must have some level of interaction with a species of interest (e.g., a target molecule or an impurity). Exemplary flocculants include polymers such as chitosan and polysaccharides.

Flocculation may also be achieved by chemical treatment resulting in changes in pH or by addition of a surfactant.

There are many ways known to those skilled in the art of removing the precipitated material, such as centrifugation, depth filtration, filtration or settling or any combinations thereof. Settling can be followed by decanting or filtering of the liquid phase or supernatant.

In some preferred embodiments, stimulus responsive polymers are used for precipitating one or more impurities. Examples of such stimulus responsive polymers can be found, e.g., in U.S. Publication Nos., 20090036651, 20100267933 and 20110313066; each of which is incorporated by reference herein in its entirety. Stimulus responsive polymers are generally soluble in an aqueous based solvent under a certain set of process conditions such as pH, temperature and/or salt concentration and are rendered insoluble upon a change in one or more of such conditions and subsequently precipitate out. Exemplary stimulus responsive polymers include, but are not limited to, polyallylamine, polyallylamine modified with a benzyl group or polyvinylamine and polyvinylamine modified with a benzyl group, where the stimulus is phosphate or citrate.

In some embodiments, a stimulus responsive polymer is continuously added using a static mixer. In other embodiments, both the polymer as well as the stimulus to which it is responsive are added using a static mixer.

In some embodiments, small molecules are used for precipitating one or more impurities, especially insoluble impurities.

In some embodiments, small molecules used in the processes described herein are non-polar and cationic, e.g., as described in PCT Publication No. WO2013028334, incorporated by reference herein. Exemplary small molecules that may be used for clarification include, but are not limited to, monoalkyltrimethyl ammonium salt (non-limiting examples include cetyltrimethylammonium bromide or chloride, tetradecyltrimethylammonium bromide or chloride, alkyltrimethyl ammonium chloride, alkylaryltrimethyl ammonium chloride, dodecyltrimethylammonium bromide or chloride, dodecyldimethyl-2-phenoxyethylammonium bromide, hexadecylamine chloride or bromide, dodecyl amine or chloride, and cetyldimethylethyl ammonium bromide or chloride), a monoalkyldimethylbenzyl ammonium salt (non-limiting examples include alkyldimethylbenzyl ammonium chloride and benzethonium chloride), a dialkyldimethyl ammonium salt (non-limiting examples include domiphen bromide, didecyldimethyl ammonium halides (bromide and chloride salts) and octyldodecyldimethyl ammonium chloride or bromide), a heteroaromatic ammonium salt (non-limiting examples include cetylpyridium halides (chloride or bromide salts) and hexadecylpyridinium bromide or chloride, cis-isomer 1-[3-chloroallyl]-3,5,7-triaza-1-azoniaadamantane, alkyl-isoquinolinium bromide, and alkyldimethylnaphthylmethyl ammonium chloride), a polysubstituted quatemary ammonium salt, (non-limiting examples include alkyldimethylbenzyl ammonium saccharinate and alkyldimethylethylbenzyl ammonium cyclohexylsulfamate), and a bis-quaternary ammonium salt (non-limiting examples include 1,10-bis(2-methyl-4-aminoquinolinium chloride)-decane, 1,6-Bis {1-methyl-3-(2,2,6-trimethyl cyclohexyl)-propyldimethyl ammonium chloride hexane or triclobisonium chloride, and the bis-quat referred to as CDQ by Buckman Brochures).

In a particular preferred embodiment, the small molecule is benzethonium chloride (BZC).

In some embodiments, clarification is performed directly in a bioreactor. In other words, a precipitant, e.g., a stimulus responsive polymer, may be added directly to a bioreactor containing a culture of cells expressing a target molecule, thereby precipitating the cells and cell debris, and where the target molecule remains in the liquid phase obtained as a result of the precipitation. In some preferred embodiments, the liquid phase is further subjected to depth filtration. The liquid phase may also be subjected to centrifugation, filtration, settling, or combinations thereof.

In other embodiments, a stimulus responsive polymer is added to a vessel which contains the cell culture and is separate from a bioreactor. Therefore, as used herein, the term "vessel," refers to a container separate from a bioreactor which is used for culturing cells.

In some embodiments, a stimulus responsive polymer is added to a sample before centrifugation, and centrifugation is followed by depth filtration. In such a process, the size/volume of the depth filter which may be required following centrifugation is smaller than what is required in the absence of stimulus responsive polymer.

In some embodiments, a clarified cell culture feed is further subjected to a charged fluorocarbon composition (CFC), to further remove host cell proteins (HCPs), as described in PCT Application No. PCT/US2013/32768 (internal ref no. MCA-1303PCT), filed Mar. 18, 2013, which describes a CFC-modified membrane for removal of HCPs. CFC-modified membranes can also be used after other process steps in the purification process, e.g., following Protein A bind and elute chromatography step or following flow-through purification process step or following the anion-exchange chromatography step, which is part of the flow-through purification process step.

The clarified sample is typically subjected to a bind and elute chromatography step.

Bind and Elute Chromatography

In various embodiments described herein, the processes and systems include only a single bind and elute chromatography process step for capture, which typically follows clarification. Bind and elute chromatography is intended to bind the target molecule, whereas the one or more impurities flow through (also referred to as the "capture step"). The bound target molecule is subsequently eluted and the eluate or output from the bind and elute chromatography step may be subjected to further purification steps.

Bind and elute chromatography may employ a single separation unit or two or three or more separation units.

In various embodiments described herein, bind and elute chromatography that is used is affinity bind and elute chromatography or cation exchange bind and elute chromatography or mixed mode bind and elute chromatography. Typically, bind and elute chromatography employs the use of a media which is intended to bind the target molecule.

In some preferred embodiments, the bind and elute chromatography is an affinity chromatography. Suitable chromatography media that may be used for affinity chromatography include, but are not limited to, media having Protein A, Protein G or Protein L functional groups (e.g., ProSep® High Capacity (EMD Millipore), ProSep® Ultra Plus (EMD Millipore), Poros® MabCapture™ A (Life Technologies), AbSolute® (NovaSep), Protein A Ceramic HyperD® (Pall Corporation), Toyopearl AF-rProtein A-650F (Tosoh), Mab-Select® Sure (GE Healthcare)). Suitable media are usually packed in a chromatography column or device.

In a particular embodiment, the affinity chromatography media includes a Protein A based ligand coupled to a hydrophilic rigid polyvinylether polymer matrix.

In some embodiments according to the present invention, the bind and elute chromatography process employs continuous multi-column chromatography, also referred to as CMC.

In continuous chromatography, several identical columns are typically connected in an arrangement that allows columns to be operated in series and/or in parallel, depending on the method requirements. Thus, all columns can be run simultaneously or may overlap intermittently in their operation. Each column is typically loaded, eluted, and regenerated several times during a process run. Compared to conventional chromatography, where a single chromatography cycle is based on several consecutive steps, such as loading, washing, elution and regeneration, in case of continuous chromatography based on multiple identical columns, all these steps may occur on different columns. Accordingly, continuous chromatography operation may result in a better utilization of chromatography resin and reduced buffer requirements, which benefits process economy.

Continuous bind and elute chromatography also includes simulated moving bed (SMB) chromatography.

In some preferred embodiments, bind and elute chromatography employs CMC which uses two separation units. In some other preferred embodiments, bind and elute chromatography employs CMC which uses two or three or more units. In case of CMC, the loading of a sample is usually continuous; however, the elution is intermittent or discontinuous (i.e., CMC is semi-continuous in nature).

In some preferred embodiments, CMC employs three separation units, each containing the same chromatography media, and where the separation units are connected such that liquid can flow from one separation unit to the next separation unit and from the last to the first separation unit, where the sample is loaded onto the first separation unit at a pH and conductivity which enables binding of the target molecule to the separation unit and where at least part of duration of loading time overlaps with the loading of the consecutive separation unit, where the two separation units are in fluid communication, such that to enable any target molecules that do not bind to the first separation unit being loaded to bind to the next separation unit.

Different separation units can be at different stages of the process at any given time; i.e., while one separation unit is being loaded, the next separation unit could be subjected to washing, eluting, re-equilibration etc. Also, while the first separation unit is being subjected to the washing, eluting, re-equilibrating steps, the consecutive separation unit is subjected to the loading step and so forth, such that the sample flows continuously through the separation units and has a velocity above 800 cm/h and that the chromatography media of the separation units comprises particles with a diameter between 40 and 200 μm and with pore diameters in the range between 50 nm and 200 nm.

In some embodiments, each separation unit includes an affinity chromatography media such as, e.g., Protein A based media. In other embodiments, each separation unit includes an ion exchange media (e.g., a cation exchange chromatography media) or a mixed-mode chromatography media.

Exemplary continuous chromatography processes which may be used in the bind and elute chromatography process step, as described herein, can be found, e.g., in European Patent Application Nos. EP11008021.5 and EP12002828.7, both incorporated by reference herein.

In some embodiments, the separation units are connected in a circular manner, also referred to as a simulated moving bed. For example, in certain instances, at least three separation units are connected in a circle and the loading of the sample is shifted sequentially from one separation unit to the next, e.g., as described in European Patent No. 2040811, incorporated by reference herein.

It has been found that running bind and elute chromatography in a semi-continuous or continuous mode enables using a reduced volume of an affinity media, by up to 90% of the volume used in a conventional process. Further, separation units with a reduced diameter, between one third and one fifth compared to a batch process, can be used. The separation units can be re-used multiple times within the processing of a particular batch of a target molecule, e.g., during the batch production of a target molecule which is a therapeutic candidate.

In some embodiments, a separation unit that is being loaded with a sample is in fluid communication with another separation unit over the entire duration of the loading time.

In other embodiments, the separation unit that is being loaded is in fluid communication with another separation unit for only part of the duration of the loading time. In some embodiments, two separation units are in fluid communication only for a second half of the duration of the loading time.

In a batch chromatography mode, typically loading of a separation unit (e.g., a chromatography column) is stopped prior to an excess of target molecule saturating the separation unit. In contrast, in case of a CMC bind and elute chromatography process step, as used in the processes and systems described herein, the loading of a separation unit does not have to be stopped as target molecules that do not bind to one separation unit move on to the next separation unit because of fluid communication between the two separation units, where the outlet of one separation unit is connected with the inlet of a second separation unit and so forth. It is understood that a person skilled in the art can readily determine when during the loading step, the amount of a target molecule that is not bound to the separation unit that is being loaded is sufficiently high, such that the outlet of the separation unit being loaded needs to be connected to the inlet of another separation unit. It has been found that this embodiment is especially effective if the separation units comprise media having a particle diameter between 40 and 200 μm and pore diameter ranging from 50 to 200 nm. With such media, the loading feed can be run continuously at a velocity above 800 cm/h. Further details can be found in EP12002828.7, filed on Apr. 23, 2012. In some embodiments, the outlet of the separation unit or the separation units that are being washed is in a fluid communication with the previous separation unit so that target molecules removed by said washing are not lost but loaded onto the previous separation unit.

It has been found that the level of impurities (e.g., HCPs) that end up in the elution pool containing the target molecule can be significantly reduced with use of certain additives to the sample load during bind and elute chromatography. In fact, addition of certain additives to the sample prior to loading or during the loading of the sample may obviate the need to use specific wash steps typically designed to enhance impurity clearance. In other words, the number of wash steps that are typically used is reduced by inclusion of certain additives prior to loading or during the loading of the sample.

In the context of continuous chromatography, a Protein A column that has completed the loading step and is moved to subsequent zones is required to complete all necessary steps within a time frame expected such that the column will be ready to accept fresh loading solution, e.g., as described herein, can be found, e.g., in European Patent Application Nos. EP11008021.5 and EP12002828.7, both incorporated by reference herein. The time that is required to complete all necessary steps depends on the number of steps or zones that the column must go through to be ready for loading again. By reducing or eliminating steps, such as intermediate washing, the application of continuous chromatography for higher titers (target protein concentrations) is enabled where the loading phase is expected to be shorter as well as simplifies the timing required for all titer conditions during continuous chromatography.

Exemplary additives which may be employed to reduce or eliminate one or more intermediate wash steps include, but are not limited to, salts, polymers, surfactants or detergents, solvents, chaotropic agents and any combinations thereof. A "salt" is a compound formed by the interaction of an acid and a base. Examples of salts include any and all chloride salts, sulfate salts, phosphate salts, acetate and/or citrate salts, e.g., sodium chloride, ammonium sulfate, ammonium chloride, potassium chloride, sodium acetate. In a particular embodiment, the salt is NaCl (e.g., added to a final concentration of 0.5 M NaCl). The term "hydrophobic salt" refers to a specific salt type with a hydrophobic component such as, alkylamines; tetramethylammonium chloride (TMAC), tetraethylammonium chloride (TEAC), tetrapropylammonium chloride and tetrabutylammonium chloride. As used herein, a "polymer" is a molecule formed by covalent linkage of two or more monomers, where the monomers are not amino acid residues. Examples of polymers include polyethylene glycol (PEG), propylene glycol, and copolymers of ethylene and propylene glycol (e.g., Pluronics, PF68, etc.). In a particular embodiment, the polymer is PEG.

The term "detergent" refers to surfactants, both ionic and nonionic, such as polysorbates (e.g., polysorbates 20 or 80); poloxamers, (e.g., poloxamer 188); Triton; sodium dodecyl sulfate (SDS); sodium lauryl sulfate; sodium octyl glycoside; lauryl-, myristyl-, linoleyl-, or stearyl-sulfobetaine; (see U.S. Pat. No. 6,870,034B2 for more detergents). In a particular embodiment, the detergent is a polysorbate, such as polysorbate 20 (Tween 20).

The term "solvent" refers to a liquid substance capable of dissolving or dispersing one or more other substances to provide a solution. In some embodiments, the solvent is an organic, non-polar solvent such as ethanol, methanol, isopropanol, acetonitrile, hexylene glycol, propylene glycol and 2,2-thiodiglycol. The term "chaotropic salt" refers to a salts that is known to disrupt the intermolecular water structure. An example of such a salt is urea and guanidinium HCl.

In some embodiments, the one or more additives are mixed continuously with a clarified cell culture using one or more static mixers. Accordingly, in some embodiments, a clarified cell culture sample continuously flows to the Protein A chromatography step in a protein purification process, where one or more additives, as described herein, are continuously mixed with the clarified cell culture prior to loading onto a Protein A chromatography matrix.

Virus Inactivation

In some embodiments according to the processes and systems described herein, bind and elute chromatography is followed by virus inactivation (VI). It is understood that virus inactivation may not necessarily be performed but is considered optional.

Preferably, the output or eluate from bind and elute chromatography is subjected to virus inactivation. Viral inactivation renders viruses inactive, or unable to infect, which is important, especially in case the target molecule is intended for therapeutic use.

Many viruses contain lipid or protein coats that can be inactivated by chemical alteration. Rather than simply rendering the virus inactive, some viral inactivation processes are able to denature the virus completely. Methods to inactivate viruses are well known to a person skilled in the art. Some of the more widely used virus inactivation processes include, e.g., use of one or more of the following: solvent/detergent inactivation (e.g. with Triton X 100); pasteurization (heating); acidic pH inactivation; and ultraviolet (UV) inactivation. It is possible to combine two or more of these processes; e.g., perform acidic pH inactivation at elevated temperature.

In order to ensure complete and effective virus inactivation, virus inactivation is often performed over an extended period of time with constant agitation to ensure proper mixing of a virus inactivation agent with the sample. For example, in many large scale processes used in the industry today, an output or eluate from a capture step is collected in a pool tank and subjected to virus inactivation over an extended period of time (e.g., >1 to 2 hours, often followed by overnight storage).

In various embodiments described herein, the time required for virus inactivation is significantly reduced by performing virus inactivation in-line or by employing a surge tank instead of a pool tank for this step.

Examples of virus inactivation techniques that can be used in the processes described herein can be found, e.g., in PCT Patent Application No PCT/US2013/45677 (internal ref. no. P12/098PCT).

In some preferred embodiments, virus inactivation employs use of acidic pH, where the output from the bind and elute chromatography step is subjected to in-line exposure to acidic pH for virus inactivation. The pH used for virus inactivation is typically less than 5.0, or preferably between 3.0 and 4.0. In some embodiments, the pH is about 3.6 or lower. The duration of time used for virus inactivation using an in-line method can range from 10 minutes or less, 5 minutes or less, 3 minutes or less, 2 minutes or less, to about 1 minute or less. In case of a surge tank, the time required for inactivation is typically less than 1 hour, or preferably less than 30 minutes.

In some embodiments described herein, a suitable virus inactivation agent is introduced in-line into a tube or connecting line between bind and elute chromatography and the next unit operation in the process (e.g., flow through purification), where preferably, the tube or connecting line contains a static mixer which ensures proper mixing of the output from the bind and elute chromatography process step with the virus inactivation agent, before the output goes on to the next unit operation. Typically, the output from the bind and elute chromatography flows through the static mixer at a certain flow rate, which ensures a minimum contact time with the virus inactivation agent. The contact time can be adjusted by using static mixers of a certain length and/or diameter.

In some embodiments, a base or a suitable buffer is additionally introduced into the tube or connecting line after exposure to an acid for a duration of time, thereby to bring the pH of the sample to a suitable pH for the next step, where the pH is not detrimental to the target molecule. Accordingly, in some preferred embodiments, both exposure to a low pH as well as that to a basic buffer is achieved in-line with mixing via a static mixer.

In some embodiments, instead of an in-line static mixer, or in addition to an in-line static mixer, a surge tank is used for treating the output from bind and elute chromatography with a virus inactivation agent, where the volume of the surge tank is not more than 25% of the total volume of the output from bind and elute chromatography or not more than 15% or not more than 10% of volume of the output from bind and elute chromatography. Because the volume of the surge tank is significantly less than the volume of a typical pool tank, more efficient mixing of the sample with the virus inactivation agent can be achieved.

In some embodiments, virus inactivation can be achieved by changing the pH of the elution buffer during bind and elute chromatography, rather than having to change pH of the output from bind and elute chromatography.

In some embodiments described herein, the sample is subjected to a flow-through purification process, following virus inactivation. In some embodiments, a filtration step may be included after virus inactivation and before flow-through purification. Such a step may be desirable, especially in cases where turbidity of the sample is observed following virus inactivation. Such a filtration step may employ a microporous filter or a depth filter.

Although, in processes where virus inactivation step is optional, the output from bind and elute chromatography may be directly subjected to flow-through purification.

Flow-Through Purification

In various embodiments described herein, the output from bind and elute chromatography is subjected to a flow-through purification operation either directly, or following virus inactivation. In some embodiments, flow-through purification operation used in the processes and systems described herein employs two or more process steps or devices or methods for achieving flow-through purification, which is intended to remove one or more impurities present in the output from bind and elute chromatography, with or without virus inactivation.

In some preferred embodiments, flow through purification operation, as described herein, includes one or more of the following steps performed in a flow-through mode: activated carbon; anion exchange chromatography; cation exchange chromatography, mixed mode chromatography, hydrophobic interaction chromatography and virus filtration, or combinations thereof. In some embodiments, one or more valves, in-line static mixers and/or surge tanks may be used between two or more of these steps, in order to change solution conditions.

The various steps, one or more of which may be used to achieve flow-through purification, are described in more detail infra.

As described herein, in some embodiments, in some preferred embodiments, flow-through purification employs at least one flow-through anion exchange chromatography (AEX) step, where one or more impurities still remaining in the sample containing the target molecule bind the anion exchange chromatography media, whereas the target molecule flows through.

In some embodiments, flow-through mixed-mode chromatography or flow-through hydrophobic interaction chromatography may be used instead, or in addition to flow-through anion-exchange chromatography.

Exemplary anion exchange media which may be employed for AEX chromatography, include, but are not limited to, such as those based on quaternary ammonium ions, as well as weak anion exchangers, such as those based on primary, secondary, and tertiary amine. Additional examples of suitable anion exchange media are Q Sepharose® available from GE Healthcare Bio-Sciences AB, Fractogel TMAE and Eshmuno Q available from EMD Chemicals, Mustang® Q available from Pall Corp., Sartobind® Q available from Sartorius Stedim, and ChromaSorb™ devices available from EMD Millipore.

The media can be in the form of particles, membranes, porous materials or monolithic materials. In preferred embodiments, media are membrane based matrices, also called membrane adsorbers. The membrane adsorber is preferably a porous membrane sheet made by phase separation methods well known in the art. See, for example, Zeman L J, Zydney A L, Microfiltration and Ultrafiltration: Principles and Applications, New York: Marcel Dekker, 1996. Hollow fiber and tubular membranes are also acceptable matrices. The membrane adsorbers typically have a bed height of 0.5 to 5 mm.

Membranes can be manufactured from a broad range of polymeric materials known in the art, including polyolefins, such as polyethylene and polypropylene, polyvinylidene fluoride, polyamide, polytetrafluoroethylene, cellulosics, polysulfone, poly acrylonitrile, etc.

In order to impart anion exchange properties, the surface of the membranes is usually modified by coating, grafting, adsorption, and plasma-initiated modification with suitable monomers and/or polymers.

In some embodiments, the anion exchange media that is used for flow-through anion exchange is a membrane based media having a surface coated with a crosslinked polymer having attached primary amine groups such as a polyallylamine or a protonated polyallylamine.

Additional suitable media can be found in, e.g., U.S. Pat. No. 8,137,561, incorporated by reference herein, which describes porous chromatographic or adsorptive media having a porous, polymeric coating formed on a porous, self-supporting substrate and anionic exchangers including such media as well as use methods of purifying a target molecule using such media Such media are particularly suited for the robust removal of low-level impurities from manufactured target molecules, such as monoclonal antibodies, in a manner that integrates well into existing downstream purification processes. Typical impurities include DNA, endotoxin, HCP and viruses. Such media function well at high salt concentration and high conductivity (high affinity), effectively removing viruses even under such conditions. High binding capacity without sacrificing device permeability is achieved. Indeed, depending on the coating properties, nucleic acid binding capacities of greater than about 5 mg/mL, or greater than about 25 mg/mL, or greater than about 35-40 mg/mL, may be achieved. The amount of the anion exchange adsorber is much less than that used for a comparable bead-based process.

In some embodiments, the membranes having an anion exchange functionality are encapsulated in a suitable multilayer device providing uniform flow through the entire stack of the membrane. The devices can be disposable or reusable, and can either be preassembled by the membrane manufacturer or assembled by the end user. Device housing materials include thermoplastic resins, such as polypropylene, polyethylene, polysulfone, polyvinylidene fluoride, and the like; thermoset resins such as acrylics, silicones and epoxy resins; and metals such as stainless steel. The membrane can either be permanently bonded to the device housing, such as by using an adhesive or thermal bonding, or held in place by compression and carefully placed gaskets.

In some preferred embodiments, the anion-exchange adsorber device is used at the solution pH value that is at least 0.5-1.0 units below the isoelectric point of the target protein. The preferred pH range of anion-exchange adsorber device is from about 6 to about 8. Suitable range of salt concentration is between 0 and 500 mM, more preferably between 10 and 200 mM.

In some embodiments, flow-through purification may employ additional steps. For example, in a preferred embodiment, one or more additional flow-through steps are used in addition to anion-exchange chromatography (AEX). The additional flow-through steps include, e.g., mixed-mode chromatography, cation exchange chromatography, hydrophobic interaction chromatography, activated carbon, size exclusion or combinations thereof.

Additional steps which may be included in flow-through purification include, e.g., use of activated carbon prior to anion-exchange chromatography or after anion-exchange chromatography (and/or one or more of mixed mode and HIC). It some embodiments, activated carbon is incorporated into a cellulose media, e.g., in a column or a device. Alternatively, activated carbon can be combined with an anion-exchange media (e.g., in a column or a cartridge), thereby to further remove one or more impurities from a sample containing a target molecule. The column or cartridge may also be disposable, e.g., Millistak® Pod. The media can be in the form of particles, membranes, fibrous porous materials or monolithic materials. In case of activated carbon, it can be impregnated into a porous material, e.g., a porous fibrous material.

It has been found that a flow through activated carbon step prior to the flow-through anion exchange chromatography is especially suitable for the removal of host cell proteins and leached Protein A. It is also capable of removing a significant amount of potential impurities from cell culture media, such as hormones, surfactants, antibiotics, and anti foam compounds. In addition, it has been found that an activated carbon containing device reduces the level of turbidity in the sample, for example generated during pH increase of Protein A elution fractions.

Further details about carbonaceous materials, activated carbon and their use in flow-through purification processes can be found in PCT Publication No. WO2013/028330, which is hereby incorporated by reference.

As discussed above, the flow-through purification operation used in the processes and systems described herein may include more than one flow-through step.

In preferred embodiments, flow-through purification further includes one or more additional flow-through steps, e.g., for aggregate removal and virus filtration. In some embodiments, the sample is passed through an adsorptive depth filter, or a charged or modified microporous layer or layers in a normal flow filtration mode of operation, for aggregate removal. Examples of flow-through steps which may be used for aggregate removal can be found in, e.g., U.S. Pat. Nos. 7,118,675 and 7,465,397, incorporated by reference herein. Accordingly, in some embodiments, a two-step filtration process for removing protein aggregates and viral particles may be used, wherein a sample is first filtered through one or more layers of adsorptive depth filters, charged or surface modified porous membranes, or a small bed of chromatography media to produce a protein aggregate-free sample. This may be followed by the use of an ultrafiltration membrane for virus filtration, as described in more detail below. Ultrafiltration membranes used for virus filtration are typically referred to as nanofiltration membranes.

In some embodiments, an additional flow-through step employs a cation exchange chromatography (CEX) media. Further details about cation exchange flow through devices and their use in flow-through purification processes can be found in U.S. patent application Ser. No. 13/783,941 (internal ref no. MCA-1423), incorporated by reference herein. Accordingly, in some embodiments, a cation exchange chromatography media that is used after the anion exchange chromatography step employs a solid support containing one or more cation exchange binding groups at a density of 1 to 30 mM. Such solid supports are able to bind protein aggregates relative to monomers at a selectively greater than about 10.

In some embodiments; a negatively charged filtration medium may be used for removal of protein aggregates, e.g., comprising a porous substrate coated with a negatively charged polymerized cross-linked acrylamidoalkyl coating, polymerized in situ on the surface of the substrate upon exposure to an electron beam and in the absence of a chemical polymerization free-radical initiator, where the coating is formed from a polymerizable acrylamidoalkyl monomer having one or more negatively charged pendant groups and an acrylamido cross-linking agent. Additional details concerning such filtration media can be found, e.g., in PCT Publication No. WO2010/098867, incorporated by reference herein.

The use of a flow-through cation-exchange step (CEX) may necessitate a reduction of solution pH to increase affinity and capacity for impurities, such as antibody aggregates. Such pH reduction can be performed by a simple in-line addition of suitable solution containing acid, via a three-way valve, a T-style connector, a static mixer, or other suitable devices well known in the art. In addition, a small surge vessel can be employed to provide additional mixing and access for sampling. The volume of the surge vessel, which can be in the form of a bag, a container, or a tank, is usually considerably smaller that the volume of the fluid processed with flow-through setup, for example not more than 10% of the volume of the fluid.

In some embodiments, the cation exchange media removes protein aggregates and/or acts as a pre-filter for a virus-filtration membrane, typically used after cation exchange chromatography.

In another embodiment, protein aggregates can be removed using a composite filter material that comprises a calcium phosphate salt. Suitable calcium phosphate salts are dicalcium phosphate anhydrous, dicalcium phosphate dehydrate, tricalcium phosphate and tetracalcium phosphate. In another embodiment, the calcium phosphate salt is hydroxyapatite. The solution conditions are typically adjusted prior to loading the sample on such device, in particular concentrations of phosphate ion and the ionic strength. Further details about the removal of protein aggregates using a composite filter material that comprises a calcium phosphate salt in flow-through mode can be found in WO2011156073 A1, which is incorporated by reference herein.

The entire flow-through purification operation (including the anion exchange chromatography step and one or more additional steps, as described herein), are performed continuously without the use of a pool tank between flow-through process steps.

In some embodiments, the flow-through purification process additionally includes virus filtration. However, virus filtration is optional and may not necessarily always be used In some embodiments, virus filtration involves filtration based on size exclusion, also referred to as sieving.

For virus removal, the sample is typically passed through an ultrafiltration filter that retains the viruses while the target molecule passes through. According to IUPAC, ultrafiltration is a "pressure-driven membrane-based separation process in which particles and dissolved macromolecules smaller than 0.1 μm and larger than about 2 nm are rejected." (IUPAC, "Terminology for membranes and membrane processes" published in Pure Appl. Chem., 1996, 68, 1479). The ultrafiltration membranes used in this step are usually specifically designed to remove viruses. In contrast to ultrafiltration membranes used for protein concentration and buffer exchange, these membranes are usually not characterized by the molecular weight cut-offs, but rather by typical retention of viral particles. Viral retention is expressed in log reduction value (LRV), which is simply a $\text{Log}_{10}$ of the ratio of viral particles in feed and filtrate in a standardized test. Use of viral filtration in purification processes can be found in, e.g., Meltzer, T., and Jomitz, M., eds., "Filtration and Purification in the Biopharmaceutical Industry", 2nd ed., Informa Healthcare, 2008, Chapter 20.

Virus-retentive membranes can be manufactured in the form of a flat sheet, such as Viresolve® Pro from EMD Millipore Corporation, Ultipor® VF Grade DV20 from Pall Corporation, Virosart® CPV from Sartorius Stedim Biotech, or in the form of hollow fiber, such as Planova™ 20N from Asahi Kasei Medical Co. They can be single-layer or multi-layer products, and can be manufactured by one of many membrane production processes known in the art. A particularly beneficial combination of throughput retention can be achieved for an asymmetric, composite virus-retentive membrane, as described in U.S. Publication No. 20120076934 A1, incorporated by reference herein.

In a particular embodiment, the flow-through purification operation involves at least an activated carbon step, an anion exchange chromatography step, a cation exchange chromatography step and a virus filtration step.

Following virus filtration, the sample containing the target molecule may be subjected to one or more additional formulation/concentration steps.

Additional Process Steps

As discussed above, in some embodiments, the sample is subjected to one or more additional process steps following virus filtration.

In some embodiments, the one or more additional steps include formulation, which may employ diafiltration/concentration followed by sterile filtration.

In some embodiments, following virus filtration, the sample containing target molecule is subjected to diafiltration, which typically employs the use of an ultrafiltration membrane in a Tangential Flow Filtration (TFF) mode. In case of Tangential Flow Filtration (TFF), the fluid is pumped tangentially along the surface of the filter medium. An applied pressure serves to force a portion of the fluid through the filter medium to the filtrate side.

Diafiltration results in the replacement of the fluid which contains the target molecule with the desired buffer for formulation of the target molecule. Diafiltration is typically followed by a step to concentrate the target molecule, performed using the same membrane.

In another embodiment, single-pass tangential flow filtration (SPTFF) can be used for concentration/diafiltration. A SPTFF module includes multiple ultrafiltration devices connected in series. The target protein is sufficiently concentrated/diafiltered after a single pass through the SPTFF module without the need for a retentate loop and pump, enabling continuous operation. More information can be found in the presentation entitled "Single pass TFF" by Herb Lutz et al., presented at the American Chemical Society conference in the spring of 2011.

Following diafiltration/concentration, the sample is subjected to a sterile filtration step for storage or any other use.

Sterile filtration is typically carried out using Normal Flow Filtration (NFF), where the direction of the fluid stream is perpendicular to the filter medium (e.g. a membrane) under an applied pressure.

Systems According to the Present Invention

The present invention also provides systems for purifying a target molecule, wherein the systems include two or more unit operations connected to be in fluid communication with each other, such that to perform a process for purifying a target molecule in a continuous or semi-continuous manner. Each unit operation may employ one or more devices to achieve the intended purpose of that unit operation. Accordingly, in some embodiments, the systems described herein, include several devices which are connected to enable the purification process to be run in a continuous or semi-continuous manner.

Without wishing to be bound by theory, it is contemplated that a system can be enclosed in a closed sterile environment, thereby to perform the whole purification process in a sterile manner.

In various embodiments, the very first device in a system is a bioreactor containing the starting material, e.g., culturing cells expressing a protein to be purified. The bioreactor can be any type of bioreactor like a batch or a fed batch bioreactor or a continuous bioreactor like a continuous perfusion fermentation bioreactor. The bioreactor can be made of any suitable material and can be of any size. Typical materials are stainless steel or plastic. In a preferred embodiment, the bioreactor is a disposable bioreactor, e.g. in form of a flexible, collapsible bag, designed for single-use.

Clarification may be performed directly in the bioreactor, or alternatively, the bioreactor can simply be used for culturing the cells, and clarification is performed in a different vessel. In yet another embodiment, the cell culture is simply flowed through a depth filtration device in order to remove one or more impurities. Accordingly, in some preferred embodiments, the bioreactor is in fluid communication with a device for performing depth filtration.

The device for performing clarification (e.g., a depth filtration device) is generally connected to be in fluid communication with a device for performing capture using a bind and elute chromatography (e.g., a continuous multi-column chromatography device comprising two or more separation units). In some embodiments, the device for bind and elute chromatography is connected to be in fluid communication with a unit operation for performing flow-through purification, which may include more than one device/step. In some embodiments, an in-line static mixer or a surge tank is included between the device for bind and elute chromatography and the first device used for flow-through purification.

In some embodiments, the flow-through purification operation includes more than one device, e.g., an activated carbon device followed by a AEX chromatography device followed by an in-line static mixer and/or a surge tank for changing pH, followed by a CEX chromatography device followed by a virus filtration device. The devices could generally be in any suitable format, e.g., a column or a cartridge.

The last unit operations in the system may include one or more devices for achieving formulation, which includes diafiltration/concentration and sterile filtration.

Typically, each device includes at least one inlet and at least one outlet, thereby to enable the output from one device to be in fluid communication with the inlet of a consecutive device in the system.

In most processes and systems used in the industry today, each device used in a purification process employs a process equipment unit, also referred to as a "skid," which typically includes the necessary pumps, valves, sensors and device holders. Typically, at least one skid is associated with each device. In some of the embodiments described herein, the number of skids used throughout the purification process is reduced. For example, in some embodiments, only one skid is used to perform the entire flow-through purification operation, which may include multiple devices, e.g., activated carbon device, anion exchange chromatography device, cation exchange chromatography device and virus filtration device, along with any equipment needed for solution condition changes. Accordingly, in some embodiments, a single skid may be used for all of the foregoing steps in flow-through purification.

In some embodiments, fluid communication between the various devices is continuous; in that the fluid flows directly through all the devices without interruptions. In other embodiments, one or more valves, sensors, detectors, surge tanks and equipment for any in-line solution changes may be included between the various devices, thereby to temporarily interrupt the flow of fluid through the system, if necessary, for example, to replace/remove a particular device.

In some embodiments, one or more surge tanks are included between the various devices. In some embodiments, not more than 3 and not more than 2 surge tanks are present in the entire system. The surge tanks located between different devices have no more than 25%, and preferably no more than 10% of the entire volume of the output from the first of the two devices.

In some preferred embodiments, the systems described herein include one or more static mixers for buffer exchange and/or in-line dilution.

In some embodiments, a system further includes one or more sensors and/or probes for controlling and/or monitoring one or more process parameters inside the system, for example, temperature, pressure, pH, conductivity, dissolved oxygen (DO), dissolved carbon dioxide ($DCO_2$), mixing rate, flow rate, product parameters. The sensor may also be an optical sensor in some cases.

In some embodiments, process control may be achieved in ways which do not compromise the sterility of the system.

In some embodiments, sensors and/or probes may be connected to a sensor electronics module, the output of which can be sent to a terminal board and/or a relay box. The results of the sensing operations may be input into a computer-implemented control system (e.g., a computer) for calculation and control of various parameters (e.g., temperature and weight/volume measurements, purity) and for display and user interface. Such a control system may also include a combination of electronic, mechanical, and/or pneumatic systems to control process parameters. It should be appreciated that the control system may perform other functions and the invention is not limited to having any particular function or set of functions.

This invention is further illustrated by the following examples which should not be construed as limiting. The contents of all references, patents and published patent applications cited throughout this application, as well as the Figures, are incorporated herein by reference.

EXAMPLES

Example 1: Process for Purifying a Monoclonal Antibody

Figure 2:
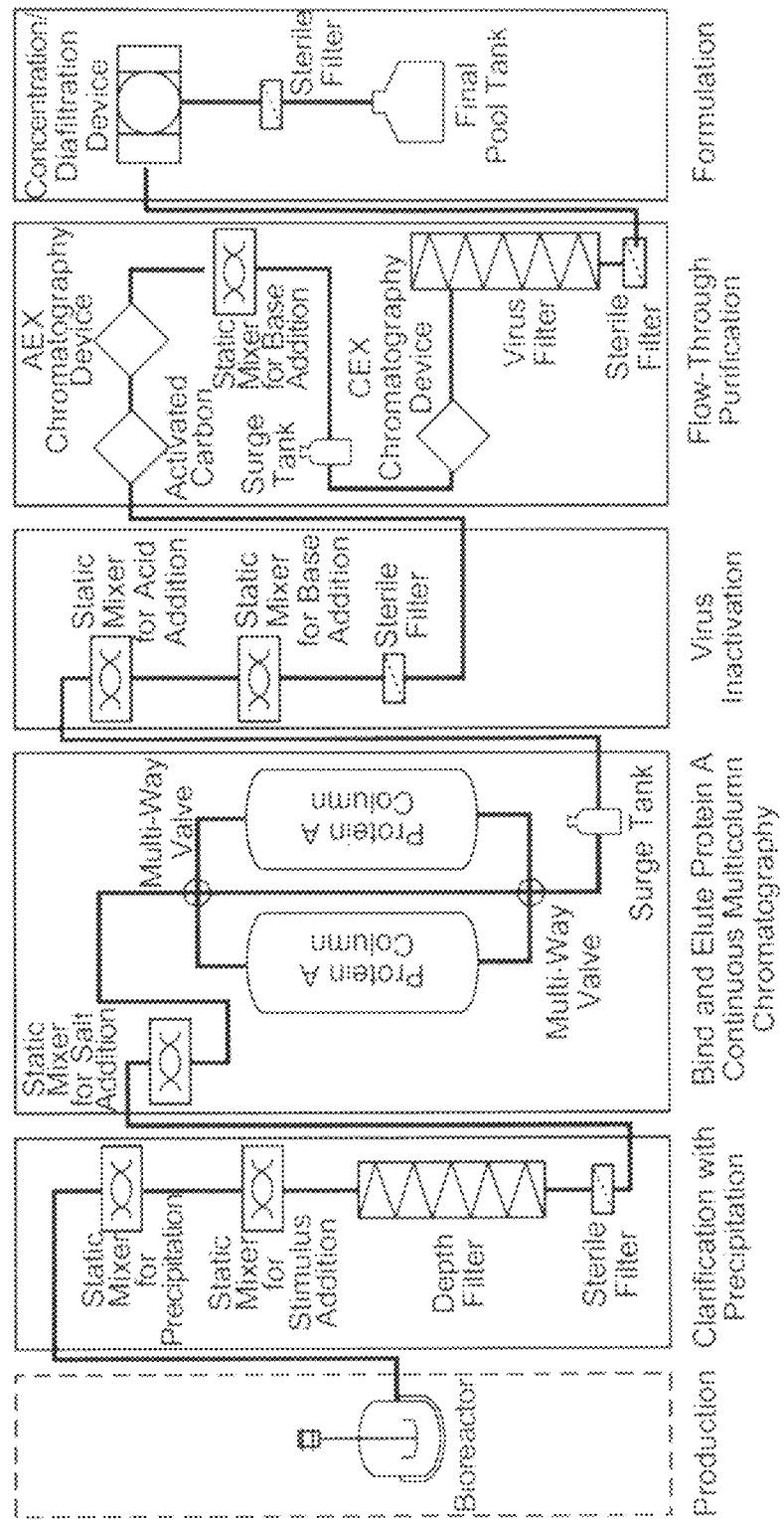
FIG. 2 is a schematic representation of an exemplary purification process, as described herein. The purification process shown uses a bioreactor for cell culture followed by the following process steps: clarification; Protein A bind and elute chromatography (capture); virus inactivation; flow-through purification; and formulation. As shown, each of the process steps employs one or more devices used to achieve the intended result of the process step. As shown, clarification employs precipitation and depth filtration; Protein A bind and elute chromatography is performed using continuous multicolumn chromatography (CMC); virus inactivation employs two in-line static mixers; flow-through purification employs activated carbon (AC) followed by anion exchange (AEX) chromatography followed by a pH change using an in-line static mixer and a surge tank followed by flow-through cation exchange (CEX) chromatography and virus filtration; and formulation employs a diafiltration/concentration tangential flow filtration device followed by sterile filtration. One or more sterile filters are also employed throughout the process.

In this representative example, the purification of a monoclocal antibody is achieved using a purification process in a continuous manner, where various unit operations are connected in a manner to operate continuously. An exemplary process is depicted in FIG. 2.

The representative example described below includes the following steps performed in the sequence listed: clarification using depth filtration; use of one or more in-line static mixers to change solution conditions; Protein A bind and elute chromatography using continuous multicolumn chromatography which employs two separation units; pH adjustment of the output using one or more static mixers; and flow-through purification which employs depth filtration followed by activated carbon followed by anion exchange chromatography followed by pH adjustment using a static mixer followed by cation exchange chromatography followed by virus filtration.

In this example a CHO-based monoclonal antibody (MAb05) is produced in a fed batch bioreactor. Approximately 5.5 L of cell culture processed with a 0.054 $m^2$ D0HC (EMD Millipore) primary depth filter then further clarified with a 0.054 $m^2$ X0HC (EMD Millipore) secondary depth filter where both are processed at a 10 LMH flux making the loading approximately 100 L/$m^2$.

Figure 3:
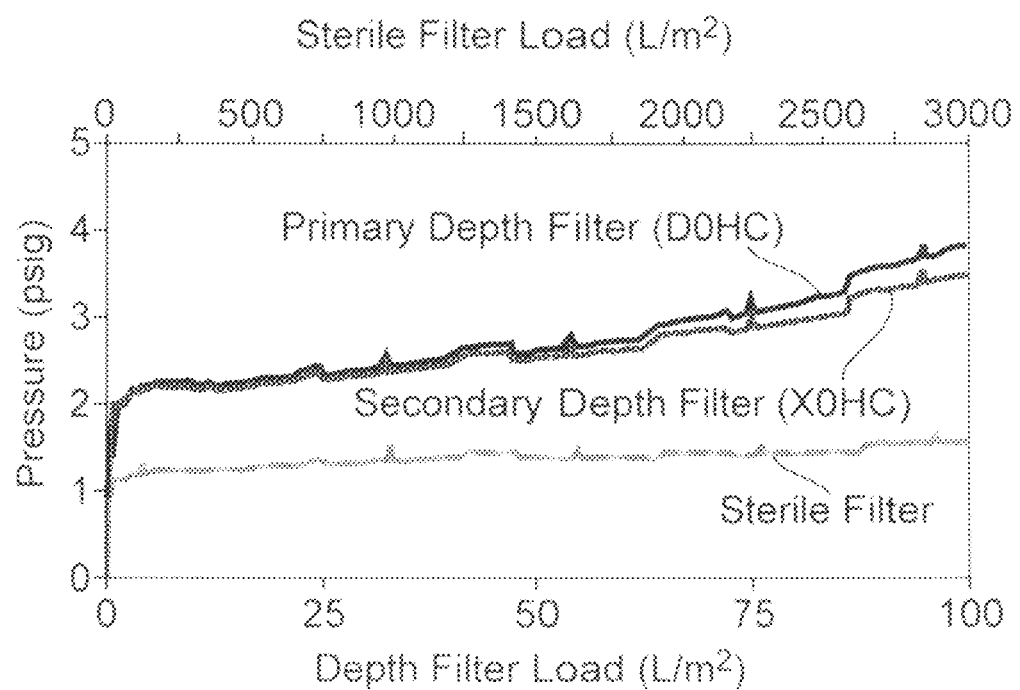
FIG. 3 is a graph depicting the results of an experiment to measure pressure of each depth filter (primary and secondary) and sterile filter used during the clarification step of the process in FIG. 2. The X-axes denote filter load ($L/m^2$), with the top X-axis referring to the load of the sterile filter and the bottom X-axis referring to the load of the two depth filters; and the Y-axis denotes the pressure in psi.
Figure 4:
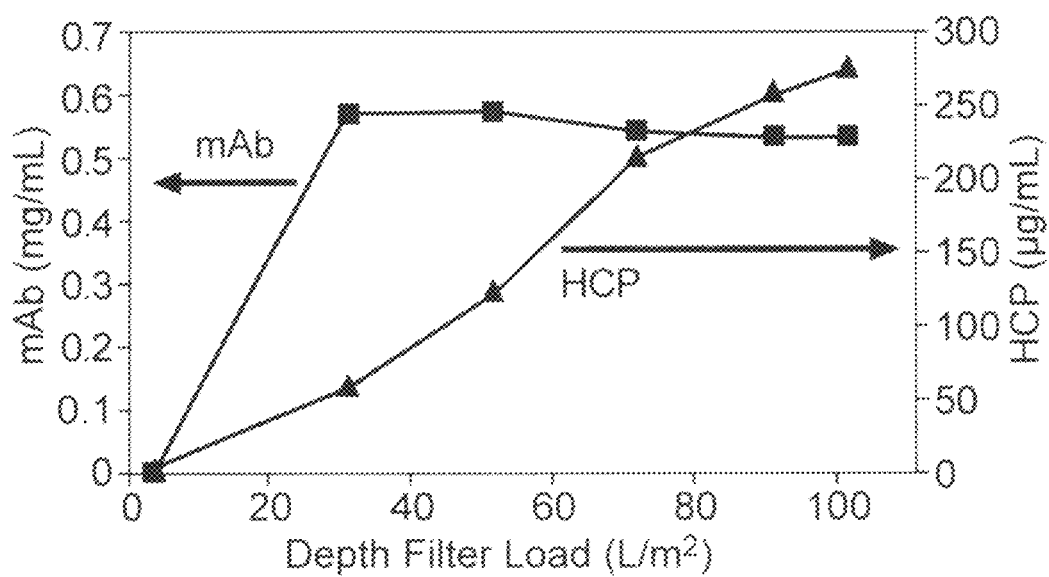
FIG. 4 is a graph depicting the results of an experiment to measure breakthrough of HCP and MAb following depth filtration prior to loading on the Protein A continuous multicolumn chromatography (CMC) set up. The X-axis denotes the depth filter load ($L/m^2$), the left Y-axis denotes MAb concentration (mg/mL) and the right Y-axis denotes the HCP concentration (μg/mL).

The effluent from the depth filtration is contacted with a 5 M NaCl solution at a 1:10 ratio that is then mixed through a static mixer followed by a sterile filter. The pressure is monitored prior to each depth filter and after the sterile filter (FIG. 3). Following the static mixer, the solution is passed through a SHC sterile filter (EMD Millipore) to a final loading of 3200 L/m2. The effluent from the sterile filter is directed to a surge tank that is monitored with a load cell to determine the amount filtered. One mL samples are collected just prior to each load cycle on Protein A continuous multi-column chromatography (CMC) (FIG. 4). After approximately 70 mL of cell culture is processed and collected in a surge tank, the clarified solution is simultaneously loaded into the next step for Protein A capture.

Protein A capture consists of two Protein A columns running on a modified Akta Explorer 100. The Protein A columns have 10 mL of ProSep Ultra Plus Protein A media packed into 1.6 cm ID Vantage-L (EMD Millipore) chromatography columns to bed heights of 10.25 and 10.85 cm. The columns are equilibrated with 1×PBS, 0.5 M NaCl for 5 column volumes (all column volumes are based on the smallest column). Throughout the run, the loading flow rate is set so as to have a loading residence time of ~1 minute. During the initial loading both columns are placed in series, where the effluent of the primary column is loaded directly onto the secondary column until a specific load volume is reached. After a specific loading volume is passed over the columns, the feed is stopped and 2 column volumes (CVs) of the equilibration buffer is passed through the primary column to the secondary column. The primary column is then positioned to undergo washing, elution, cleaning and reequilibration, while the secondary column is loaded as the primary column. Following the reequilibration of the first column, the column is then moved to the secondary position to reside in series with the now primary column. This series of events is repeated with each column taking the primary position after the original primary position column is loaded to a set volume. The first column is loaded a total of three times and the second column is loaded twice. The elutions from each column are collected into a beaker with mixing, using a UV trigger to control the start and end time of the elution.

After the first two elutions are collected and pooled, the solution is pumped out into a surge tank and mixed with a 2 M solution of tris and processed through two static mixers to increase the pH to pH 8.0, where the pH of the resulting solution is measured immediately after the static mixers. The pH adjusted solution is then processed through an A1HC depth filter (EMD Millipore) followed by a 1 cm ID Omnifit column packed with activated carbon. The effluent from the activated carbon column is then continuously flowed through an anion exchange chromatography device (e.g., ChromaSorb™) (EMD Millipore) to a loading of 4 kg of MAb/L of ChromaSorb™. The effluent from the ChromaSorb™ anion exchanger is then mixed with 1 M acetic acid, then processed through a static mixer to lower the pH to pH 5.5. The pH-adjusted solution from the static mixer is then flowed through a cation exchange chromatography device used as a prefilter, followed by virus filtration using the Viresolve® Pro membrane (EMD Millipore). The effluent from the virus filter is directed to a pool tank and sampled.

This purification process provides final solution that meets all purification targets, specifically HCP<1 ppm, aggregates<1% with a mAb05 recovery>60% for the overall process.

Example 2: Process for Purifying a Monoclonal Antibody

In this representative example, the purification of a monoclocal antibody is achieved using a purification process, where various unit operations are connected in the sequence described below.

The representative example described below includes the following steps performed in the sequence listed: clarification using stimulus responsive polymer following centrifugation; contacting the supernatent with salt; Protein A bind and elute chromatography using continuous multicolumn chromatography which employs two separation units; pH adjustment of the output using one or more static mixers; and flow-through purification which employs depth filtration followed by activated carbon followed by anion exchange chromatography followed by pH adjustment using a static mixer followed by cation exchange chromatography followed by virus filtration.

In this example, a CHO-based monoclonal antibody (MAb05) is produced in a fed-batch bioreactor. A total of 7 liters of cell culture is contacted with a solution of a stimulus responsive polymer (modified polyallylamine; responsive to salt addition) to a final polymer concentration of 0.2% v/v. The cell culture is mixed with the stimulus responsive polymer solution for approximately 10 minutes. About 175 mL of of 2 M $K_2HPO_4$ solution is added and the cell culture is mixed for an additional 10 minutes. The pH is then raised to 7.0 by adding 2 M tris base and mixing for 15 minutes. The solution is then centrifuged in 2 L aliquots at 4,500×g for 10 minutes and the supernatant is decanted and retained. The solids are disposed off. The cell culture supernatant is pooled and then mixed with 5 M NaCl at a 1:10 ratio in a batch mode with continuous stirring. The final conductivity of the solution is measured at this point and is at 55±5 mS/cm. The resulting solution is sterile filtered through a 0.22 µm Express SHC filter (EMD Millipore). The sterile filtered solution is the loading material for the Protein A chromatography.

The Protein A capture step consists of two Protein A columns running on a modified Akta Explorer 100. The Protein A columns have 10 mL of ProSep Ultra Plus Protein A media packed into 1.6 cm ID Vantage-L (EMD Millipore) chromatography column to bed heights of 10.25 and 10.85 cm. The columns are equilibrated with 1×TBS, 0.5 M NaCl for 5 column volumes, CVs (all column volumes are based on the smallest column). Throughout the run, the loading flow rate is set so as to have a loading residence time of about one minute.

During the initial loading, both columns are placed in series, where the effluent of the primary column is loaded directly onto the secondary column until a specific load volume is reached. After a specific loading volume is passed over the columns, the feed is stopped and two CVs of the equilibration buffer is passed through the primary column to the secondary column. The primary column is then positioned to undergo washing, elution, cleaning and reequilibration, while the secondary column is loaded as the primary column. Following the reequilibration of the first column, that column is then moved to the secondary position to reside in series with the now primary column. This series of events is repeated with each column taking the primary position after the original primary position column is loaded to a set volume. Each column is loaded a total of seven times. The elutions from each column are collected with a fraction collector, using a UV trigger to control the start time of the elution and collected to a constant volume of approximately 3.5 CVs.

Flow-through purification comprises of six main steps: depth filter; activated carbon; anion exchange chromatography; in-line pH adjustment; cation exchange chromatography; and virus filtration.

Figure 5:
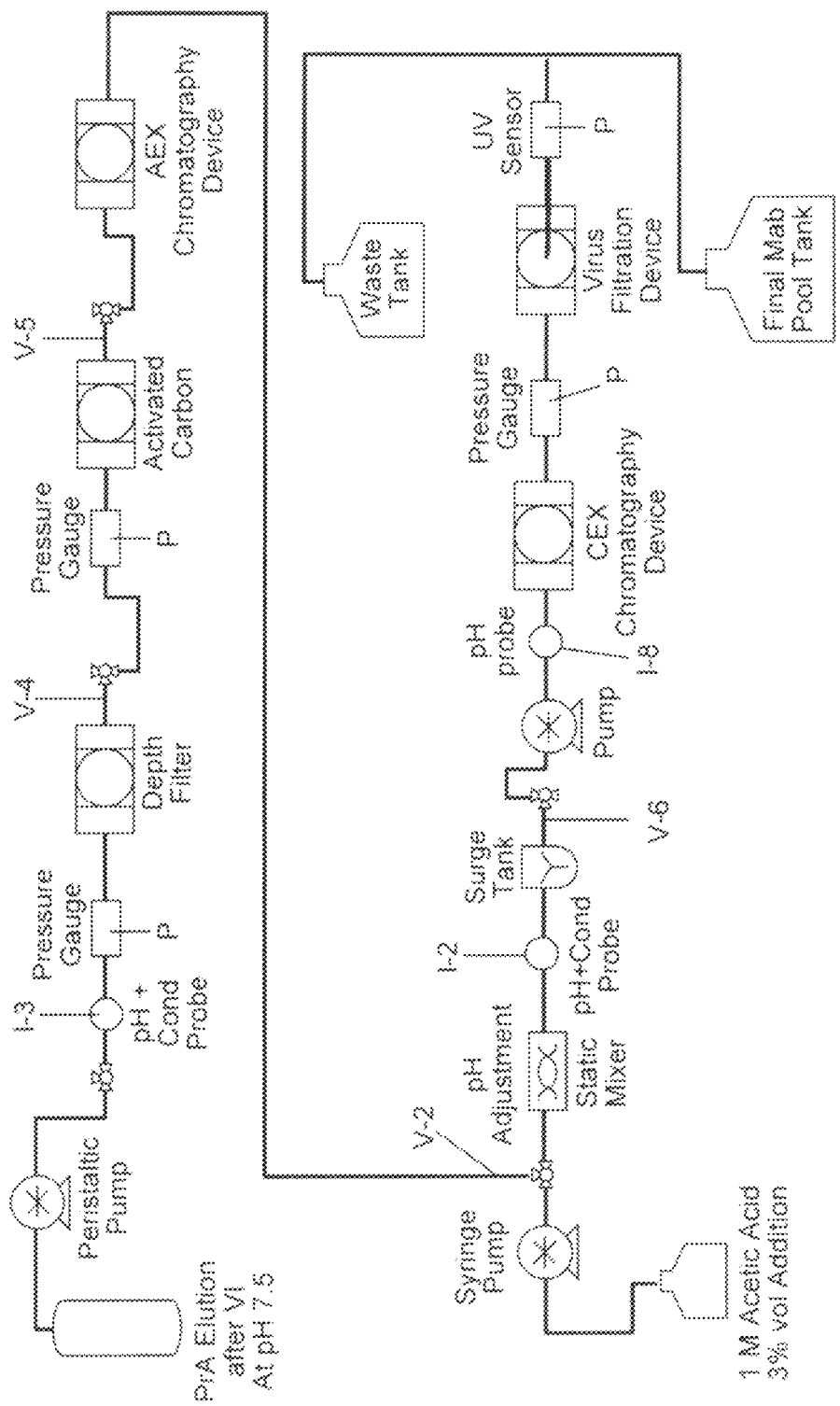
FIG. 5 is a schematic depiction of the flow-through purification process step, as further described in Example 3.

FIG. 5 illustrates the order in which these steps are connected. The necessary pumps and sensors, e.g., sensors for pressure, conductivity and UV are also shown in the schematic.

All devices are individually wetted at a different station, and then assembled as shown in FIG. 5. The devices are wetted and pre-treated according to the manufacturer's protocol or as described herein. Briefly, the depth filter (A1HC) is flushed with 100 $L/m^2$ of water followed by 5 volumes of equilibration buffer 1 (EB1: Protein A elution buffer adjusted to pH 7.5 with 1 M Tris-base, pH 11). 10 mL of activated carbon is packed into a 2.5 cm ID Omnifit column. The column is flushed with 10 CVs water, and then equilibrated with EB1 until the pH is stabilized to pH 7.5. 1.2 mL of anion exchange membrane (7 layers) is stacked into a 47 mm diameter Swinex device. The device is wetted with water at 12.5 CV/min for at least 10 min, followed by 5 device volumes (DVs) of EB1. A disposable helical static mixer (Koflo Corporation, Cary, Ill.) with 12 elements is used to perform in-line pH adjustments. A 3-layer cation-exchange chromatography device (0.12 mL membrane volume) is wetted with 10 DVs water, followed by 5 DVs of equilibration buffer 2 (EB2: EB1 adjusted to pH 5.0 using 1 M acetic acid). The device is further treated with 5 DVs of EB2+1 M NaCl, and then equilibrated with 5 DV EB2. A 3.1 cm² Viresolve® Pro virus filtration device is wetted with water pressurized at 30 psi for at least 10 minutes. The flow rate is then monitored every minute until the flow rate remains constant for 3 consecutive minutes. After all the devices are wetted and equilibrated, they are connected as shown in FIG. 5.

EB1 is run through the entire system until all pressure readings and pH readings are stabilized. Following equilibration, the feed (i.e., Protein A eluate adjusted to pH 7.5) is subjected to flow-through purification. During the run, samples are collected before the surge tank and after Viresolve® Pro to monitor MAb concentration and impurity levels (e.g., HCP, DNA, leached Protein A and aggregates). After the feed is processed, the system is flushed with 3 device volumes of EB1 to recover any MAb still remaining in the various devices as well as the connecting lines between devices.

Figure 6:
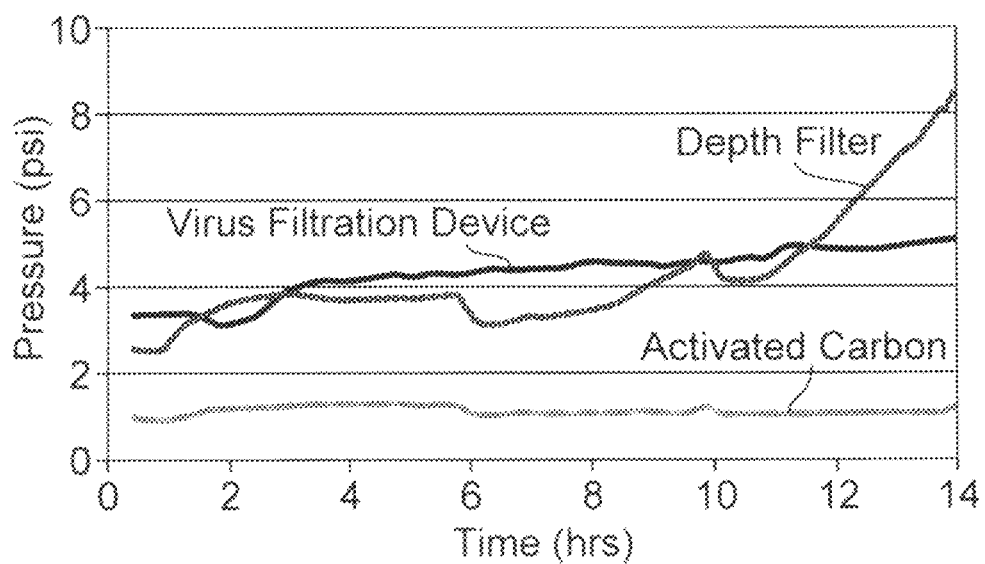
FIG. 6 is a graph depicting the results of an experiment to measure pressure profiles after depth filter, activated carbon and virus filtration. The Y-axis denotes pressure (psi) and the X-axis denotes time in hours.

FIG. 6 depicts the pressure readings after depth filter, activated carbon, and Viresolve® Pro in flow-through purification. Generally, an increase in pressure denotes fouling of filter columns. Notably, the activated carbon column remains fairly protected from any precipitate due the depth filter used before the activated carbon. The Viresolve® Pro pressure rises slowly with time, but is well below the operating maximum limit (50 psi).

The HCP breakthrough as a function of time, as measured after the anion exchange chromatography device is below the target of 10 ppm. The final HCP in the Viresolve® Pro pool is <1 ppm (Table 1). The average leached Protein A in the elution fractions is 32 ppm. The leached Protein A in the Viresolve® Pro pool is 4 ppm. The aggregates are reduced from 1% to 0.4%.

The results from the experiment are summarized in Table II below.

TABLE II

| Property measured | Results |
|---|---|
| MAb Yield (%) following flow-through purification, where the baseline of 100% is amount after Protein A CMC | 97.8% |
| Average HCP measured after Protein A CMC elution relative to that measured after virus filtration (ppm) | 172 → 1.75 |
| Average aggregates after Protein A CMC elution relative to aggregates after virus filtration (%) | 1 → 0.4% |
| Average leached Protein A after Protein A CMC elution relative to leached Protein A after virus filtration (ppm) | 32 → 4 |
| Virus Filtration throughput (kg/m²) | >6.1 |
| Dilution factor of MAb as measured by ratio of MAb concentration after Protein A CMC and after virus filtration | 1.15x |

Example 3: Flow-Through Purification Process Following Batch Protein A Chromatography In this representative experiment, a monoclonal antibody solution previously purified by batch protein A is further purified using flow-through purification to meet final purity and yield targets. This is done by performing the following steps in a flow-through manner: activated carbon; anion exchange chromatography; in-line pH change; cation exchange chromatography and virus filtration.

The set-up, equilibration and run is similar to Example 2 except for some minor modifications. The starting material is a protein A eluate from a batch protein A process. Specifically, the MAb feed processed for this run is 102 mL of 13.5 mg/mL MAb05 at a flow rate of 0.6 mL/min. A depth filter is not used in this study as the feed is filtered through a sterile 0.22 μm filter prior to performing the flow-through purification. A 2.5 mL activated carbon column is used which corresponds to a loading of 0.55 kg/L. Two anion exchange chromatography devices (0.2 and 0.12 mL) are connected in series to get a loading of 4.3 kg/L. Two 1.2 mL cation exchange chromatography devices (7 layers of the membrane on each device) are connected in parallel to handle aggregates. The MAb loading on the cation exchange chromatography devices is about 570 mg/mL. A 3.1 cm² Viresolve® Pro device is used for virus filtration.

Figure 7:
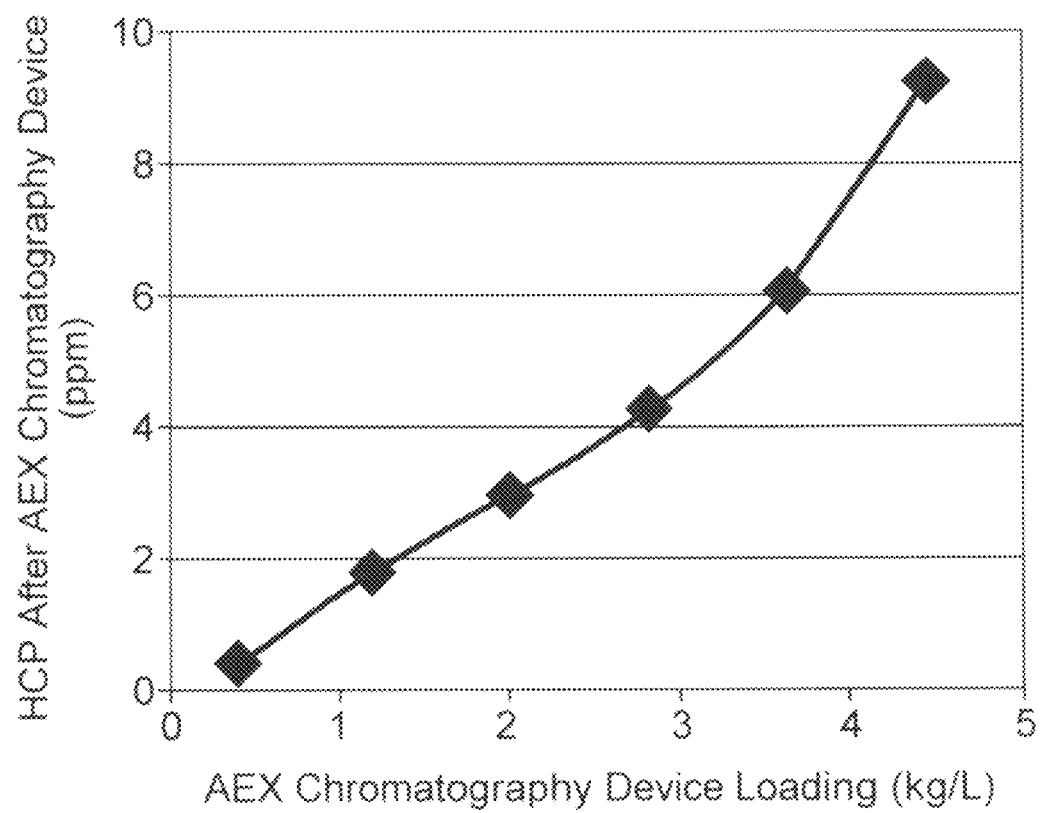
FIG. 7 is a graph depicting the results of an experiment to measure HCP breakthrough after AEX loading. The Y-axis denotes HCP concentration (ppm) and the X-axis denotes the AEX loading (kg/L).
Figure 8:
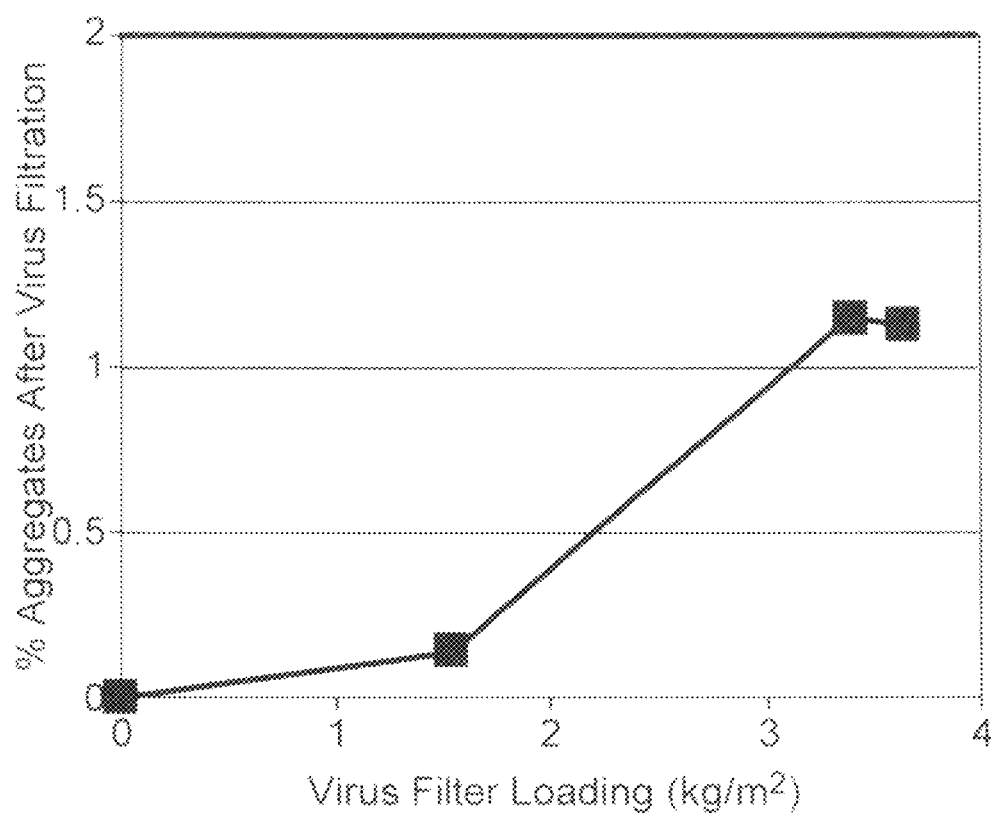
FIG. 8 is a graph depicting the results of an experiment to measure removal of MAb aggregates as a function of loading of the virus filtration device during the flow-through purification operation. The X-axis denotes the virus filtration loading ($kg/m^2$) and the Y-axis denotes percentage of MAb aggregates in the sample after virus filtration.

The HCP breakthrough as a function of loading after anion exchange chromatography device is below the target of 10 ppm (FIG. 7). The final HCP in the Viresolve® Pro pool is <1 ppm (Table 2). The aggregates are reduced from 5% to 1.1% by the cation exchange chromatography device (FIG. 8).

The results from the experiment are summarized in Table III below.

TABLE III

| Property measured | Results |
|---|---|
| MAb Yield (%) following flow-through purification, where the baseline of 100% is amount after Protein A batch chromatography | 92% |
| Average HCP measured after Protein A batch chromatography elution relative to that measured after virus filtration (ppm) | 591 → 0.61 |
| Average aggregates after Protein A batch chromatography elution relative to aggregates vafter irus filtration (%) | ~5 → 1.1% |
| Virus Filtration throughput (kg/m²) | >3.7 |
| Dilution factor of MAb as measured by ratio of MAb concentration after Protein A batch chromatography and after virus filtration | 1.25x |

Figure 9:
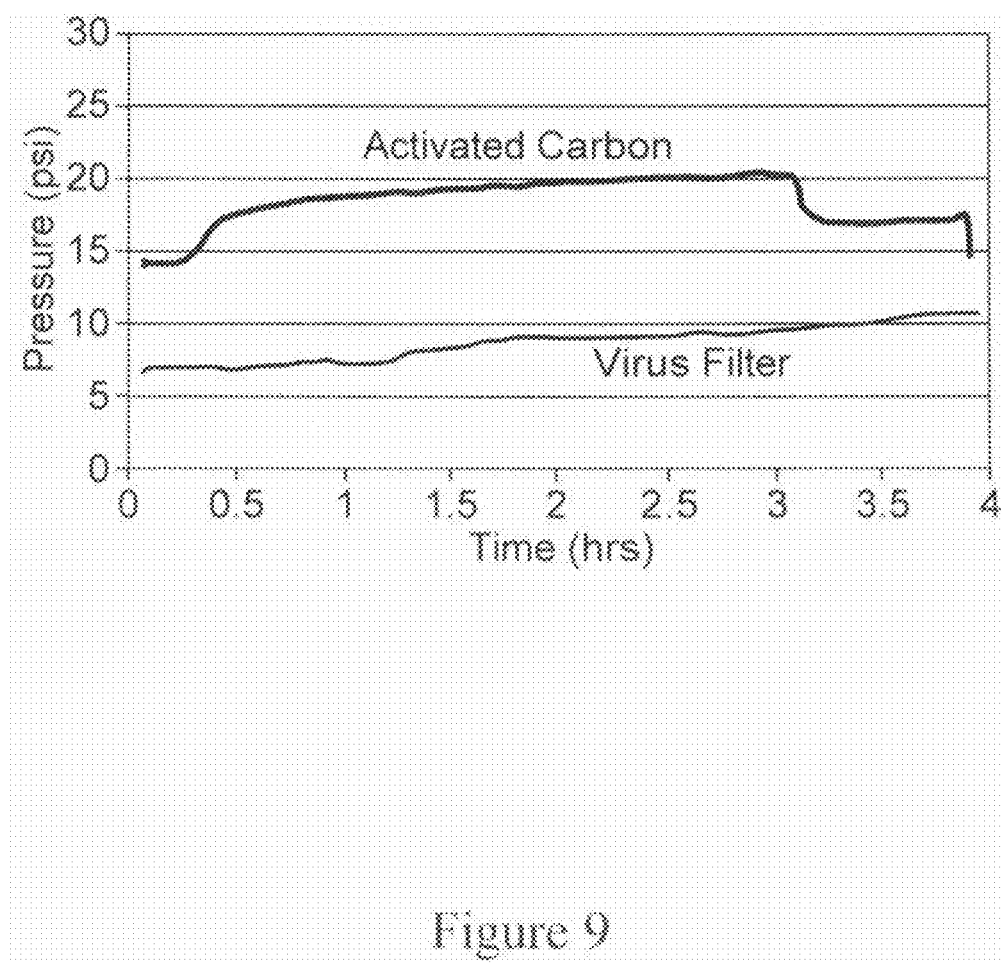
FIG. 9 is a graph depicting the results of an experiment to measure pressure profiles after activated carbon and before virus filtration during the flow-through purification operation. The X-axis denotes time in hours and the Y-axis denotes pressure in psi.

FIG. 9 shows the pressure readings before activated carbon and Viresolve® Pro. Generally, increased pressure implies the filters are getting fouled. In this case, there is a modest (about 5 psi) increase in pressure in case of activated carbon. The Viresolve® Pro pressure rises slowly with time, but is well below the operating maximum limit (50 psi).

Figure 10:
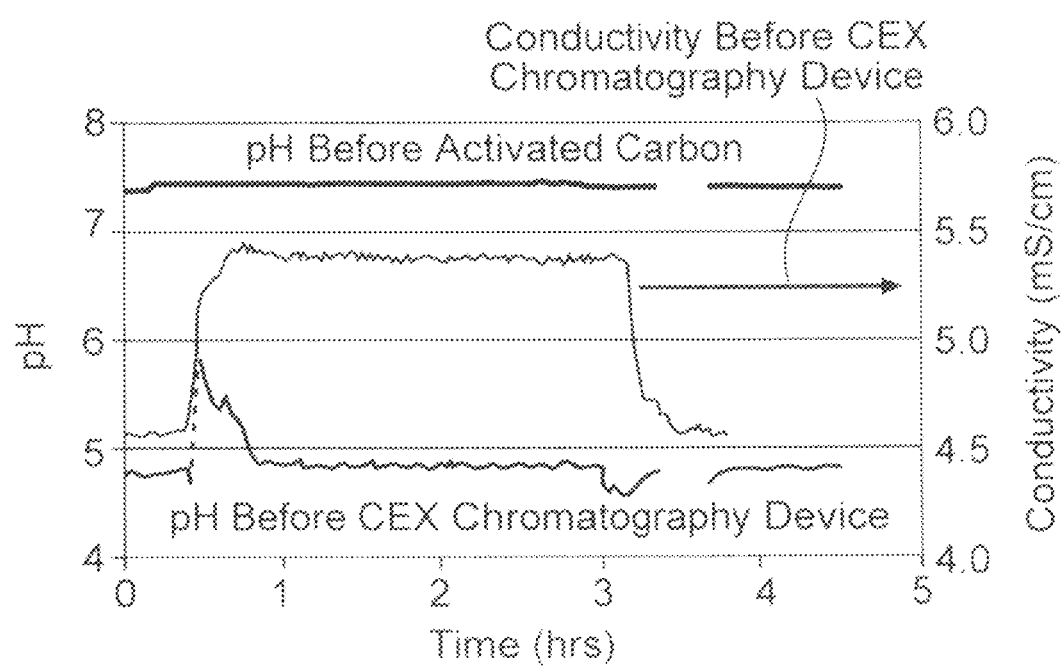
FIG. 10 is a graph depicting the results of an experiment to measure pH and conductivity profiles, where pH is measured before activated carbon and before CEX flow-through device and the conductivity is measured before CEX flow-through device. The left Y-axis denotes pH, the right Y-axis denotes conductivity (mS/cm) and the X-axis denotes time in hours.

As shown in FIG. 10, the pH after adjustment remains at the target set-point of pH 4.9 except during start-up. The pH spikes can be dampened by using a surge tank after the in-line pH adjustment and before pumping to the cation exchange chromatography device.

Example 4: Clarification Connected to Protein A Chromatography

In this representative example, clarification is connected to Protein A chromatography in a continuous manner.

In this experiment, the flow-rate that is used for depth filtration is determined by the residence time used for Protein A chromatography, which follows depth filtration. The flow-rate used in this representative example is slower than that used in conventional depth filtration, resulting in a higher HCP removal in the output recovered after Protein A chromatography.

A monoclonal antibody (MAb04) cell culture feed is obtained and split into three equal portions. The first portion (sample #1 in Table IV) is clarified using D0HC and X0HC Millistak+® primary and secondary depth filters (EMD Millipore) at a filter area ratio of 1:1 and a flow rate of 100 Liters/m²/hour (LMH), which is a typical flux used in standard clarification processes. The effluent is tested for MAb concentration and HCP amount. The second portion of the cell culture feed (sample #2) is also clarified with the same type and ratio of filters but at a flow rate of 10 LMH. This flow rate is based on a six minute residence time of the Protein A chromatography column, which follows clarification. In both cases, the same amount of material is processed, corresponding to a throughput of about 100 L/m², and the two samples are treated in the same manner.

Both clarified cell culture fluids are subjected to Protein A bind and elute chromatography, resulting in samples #3 and #4 in Table IV, where the clarification and Protein A chromatography are performed separately (i.e., are not connected). Sample #4, relating to slower flow-rate, is lost and therefore, not able to be analyzed.

The third portion of cell culture feed (sample #5) is processed through an assembly that has the effluent of the two depth filters continuously loaded onto a Protein A chromatography column (i.e., where clarification and Protein A chromatography are connected). Same chromatographic conditions as above are used. All protein A eluates are tested for MAb concentration and HCP amount. In case of sample #5, the six minute residence time of the Protein A chromatography determines the flow-rate for clarification of about 10LMH.

All results are shown in Table IV. The results indicate that the HCP levels are 2× lower after slow clarification (i.e., sample #2 relative to sample #1). A direct comparison of the corresponding samples following Protein A chromatography is not reported due to the sample loss (i.e., sample #4). A comparison of results relating to sample #5 relative to sample #3 suggests that performing clarification and Protein A chromatography in a continuous and connected manner provides a 8× improvement in MAb purity compared to the purity when clarification and Protein A chromatography are run separately. Comparing the estimated LRV values documents the difference.

TABLE IV

| # | Sample | MAb (g/L) | HCP (ng/mL) | HCP (ppm) | LRV |
|---|---|---|---|---|---|
| 1 | 100 LMH clarified | 1.19 (80%) | 256,894 | 221,426 | |
| 2 | 10 LMH clarified | 1.01 (69%) | 118,114 | 117,421 | |
| 3 | 100 LMH clarified and Protein A purified | 9.03 | 7,553 | 837 | 2.4 |
| 4 | 10 LMH clarified and Protein A purified | | not tested | | |
| 5 | 10 LMH clarified and Protein A purified in a connected manner | 7.94 | 808 | 102 | (3.1) |

Example 5: Clarification Using Stimulus Responsive Polymer

In this representative experiment, clarification is performed using a stimulus responsive polymer using two different processes.

In one process, a stimulus responsive polymer is added directly to a bioreactor (which may be a single use or disposable bioreactor) containing a cell culture expressing a target molecule. In a second process, a cell culture is pumped out of a bioreactor and contacted with a stimulus responsive polymer using one or more in-line static mixers.

In case of the process relating to performing clarification directly in a bioreactor, 60 mL of 10 wt % stimulus responsive polymer is added into a 3 L disposable bioreactor containing a cell culture and mixed for at least 5 minutes. 75 mL of 2 M $K_2HPO_4$ is added into the bioreactor and mixed for at least 5 minutes. 2 M Tris base is added into the bioreactor while mixing in order to increase pH to between 7-7.3 (approximately 50-100 mL). The solution is allowed to mix for at least 1 minute and then pumped out of the bioreactor and loaded directly onto a depth filter at a rate of 100 LMH to remove the precipitate.

In case of the process relating to the use of an in-line static mixer, cell culture is pumped out of bioreactor at a rate of 93.5 LMH to a valve or connector where it is contacted with a stimulus responsive polymer stream flowing at a rate of 1.9 LMH. The combined stream then flows into an inline static mixer sized appropriately to provide efficient mixing. The stream then flows into a second valve or connector where it is contacted with a stimulus for the polymer flowing at a rate of 2.3 LMH. The combined stream flows into a second static mixer sized appropriately to provide efficient mixing. The stream then flows into a third valve or connector where it is contacted with a 2 M Tris base stream flowing at an approximate rate of 2.3 LMH (flow of tris is adjusted to maintain a pH of 7-7.3 of the combined stream). The combined stream flows into a third static mixer that is sized appropriately to provide efficient mixing. This stream then is loaded directly on one or more depth filters in order to remove the precipitate.

It is noted that different feeds may be more sensitive to pH or may interact with a stimulus responsive polymer differently. Yields can be maximized by having the ability to treat feeds either in bioreactor, inline or a combination of the two may be used.

Use of a stimulus responsive polymer, as described herein, results in a better performance in the bind and elute chromatography process step (e.g., Protein A chromatography step), which follows the clarification step. Additionally, it is observed that the method described in this representative example results in an increase number of chromatographic cycles of the next bind and elute chromatography step, relative to clarification schemes that do not involve use of a stimulus responsive polymer. Lastly, the eulate obtained subsequent to the bind and elute chromatographic step appears to exhibit less turbidity generation upon pH change, when a stimulus responsive polymer is used upstream of the bind and elute chromatography step.

Example 6: Effect of Clarification Using Precipitation on Elution Performance of Protein A Chromatography In this representative experiment, the effect of the type of clarification performed on a CHO-based cell culture producing MAb04 on elution performance of Protein A chromatography is investigated.

A single batch of cell culture is split evenly into three aliquots. One aliquot is subjected to clarification using caprylic acid; another aliquot is subjected to clarification using a stimulus responsive polymer (i.e., modified polyallylamine); and the third aliquot is left untreated.

Following precipitation with the caprylic acid or stimulus responsive polymer, the solids are removed using centrifugation. The untreated cell culture is also centrifuged after mixing for the same amount of time as the two treated cultures. All are sterile filtered prior to use.

For each clarified solution, the conductivity of the solutions is measured and adjusted with 5 M NaCl until the conductivity reaches about 54 mS/cm. The average concentration of added NaCl is approximately 0.5 M for all solutions. The higher conductivity cell culture solutions are sterile filtered prior to loading on to separate Protein A chromatography columns.

In order to perform Protein A chromatography for each feed solution, three columns are packed with ProSep Ultra Plus media with one column having 4 mL of packed media and the other two both having 4.24 mL of packed media in 10 mm inner diameter OmniFit columns. The column bed heights are 5.1 and 5.4 cm for the 4 mL and 4.24 mL columns, respectively.

All chromatography experiments are performed on an Äkta Explorer 100 (caprylic and stimulus responsive polymer treated) or an Äkta Avant 25 (untreated). Prior to the first loading, each column is washed with at least five column volumes (CVs) of 0.15 M phosphoric acid. All chromatography runs are performed using the same basic procedure. The columns are equilibrated with 5 CVs of 1×TBS+0.5 M NaCl, followed by loading to ~30 g of MAb04 per liter of packed media. The loading zone is flushed out with 2 CVs of equilibration buffer followed by a 4 CV wash with 25 mM Tris pH 7.0. Following washing of the column, the product (MAb04) is eluted from the column with 5 CVs of 25 mM glycine HCl, 25 mM acetic acid pH 2.5. The elution is collected using the system's fraction collector with collection starting using a UV trigger and collected for a constant volume of 4 CVs. The column is cleaned with 4 CVs of 0.15 M phosphoric acid followed by a reequilibration step of 10 CVs with equilibration buffer.

The Protein A purification of the different clarified samples is performed for twelve (untreated) and nine (caprylic acid and stimulus responsive polymer treated) successive cycles.

Figure 11:
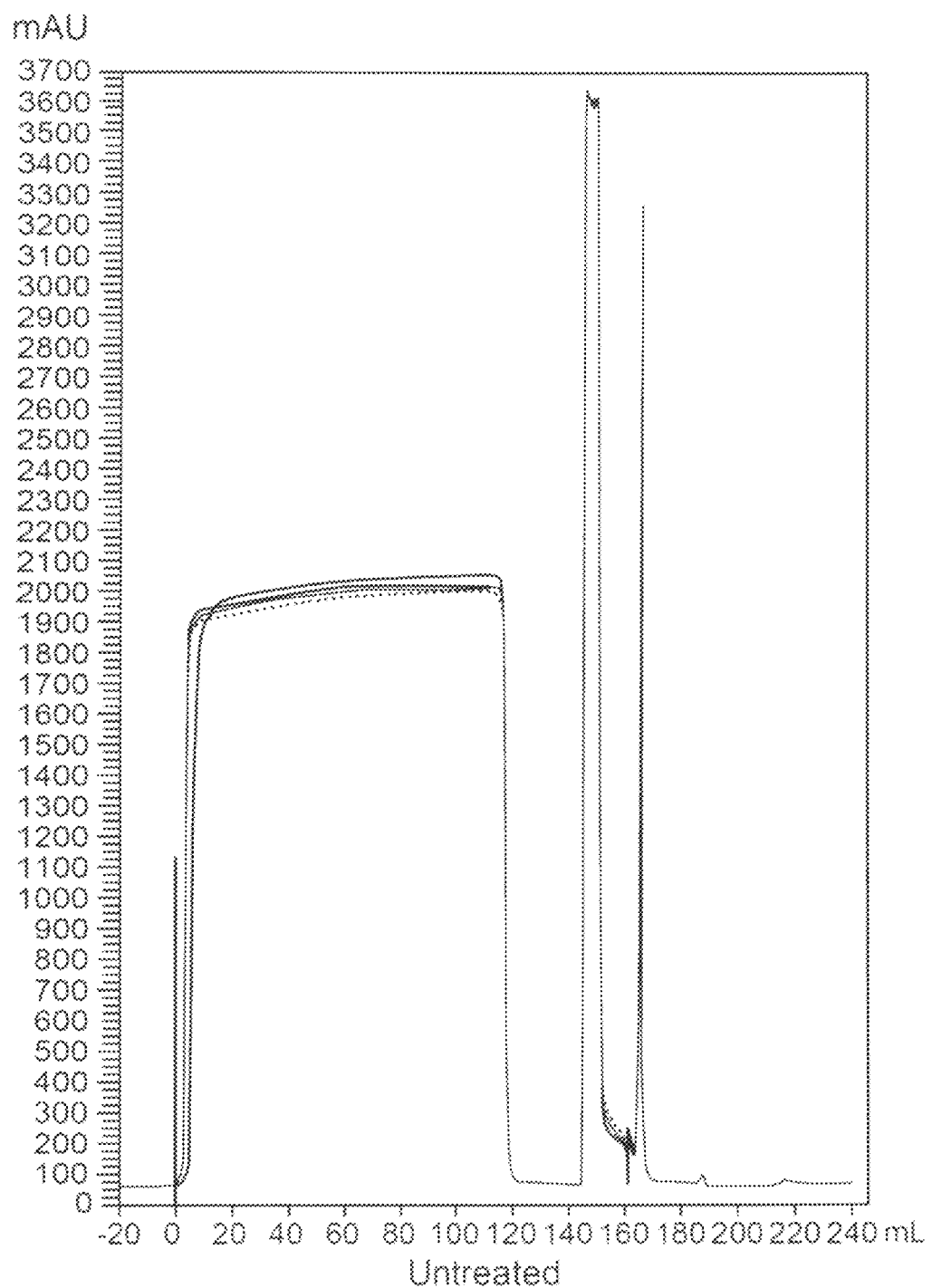
FIG. 11 is a chromatogram for Protein A capture of untreated clarified MAb04 using CMC which employs two separation units.
Figure 12:
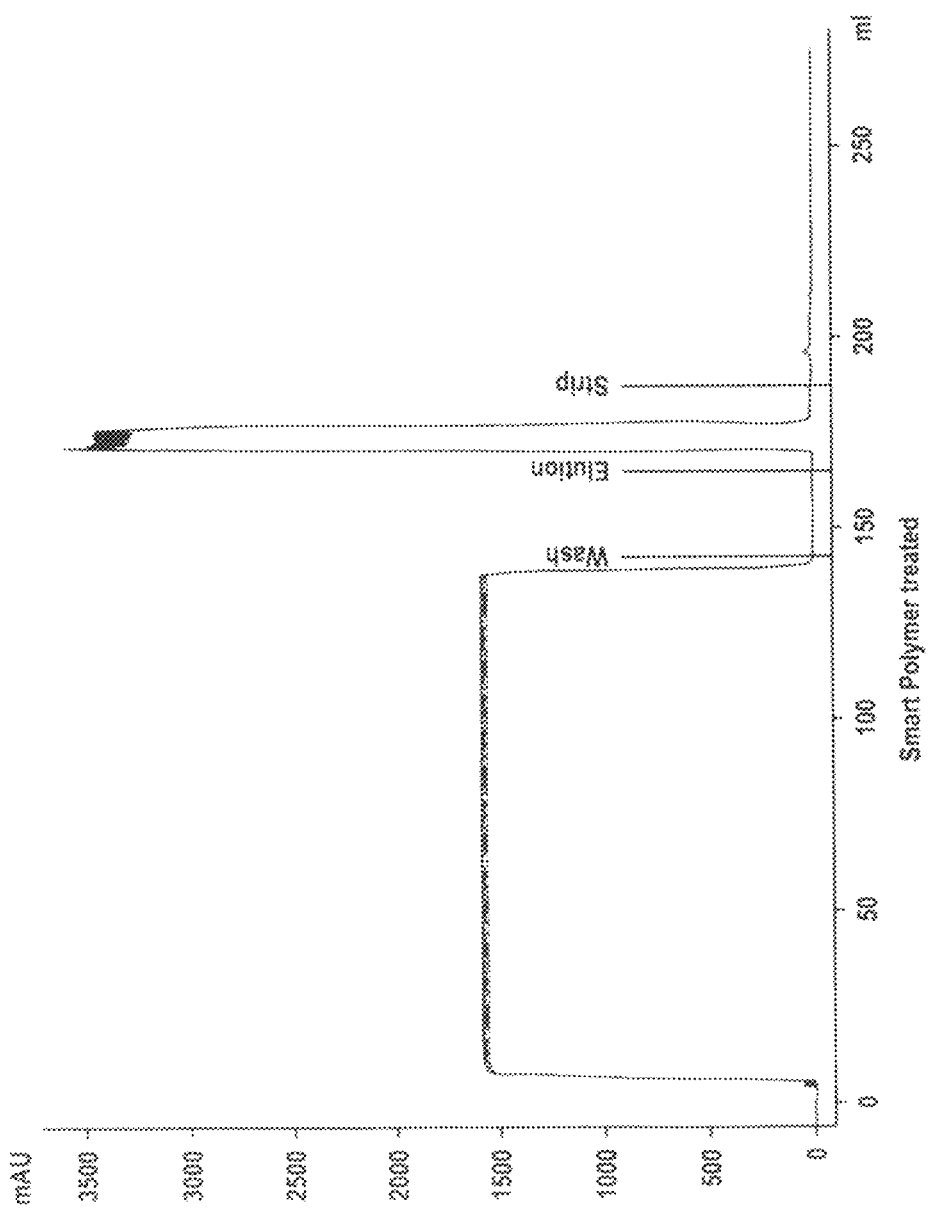
FIG. 12 is a chromatogram for Protein A capture of smart-polymer clarified MAb04 using CMC which employs two separation units.
Figure 13:
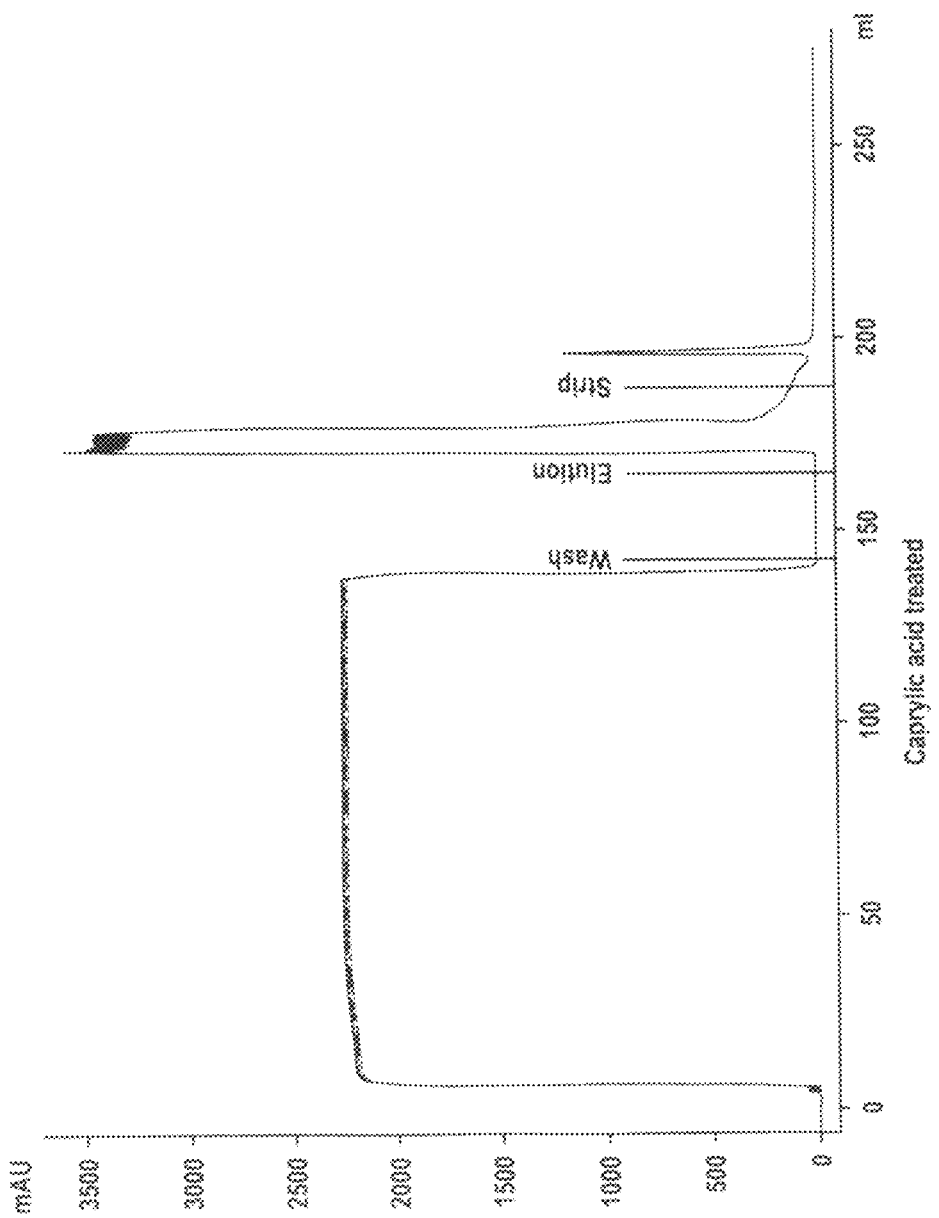
FIG. 13 is a chromatogram for Protein A capture of caprylic acid clarified MAb04 using CMC which employs two separation units.

FIGS. 11, 12 and 13 depict the overlaid chromatograms for all experiments, in each case displaying the load, elution and cleaning peaks in sequence. It is evident that the elution peak without stimulus responsive polymer treatment has visible and significant trailing as compared to the elution peaks from the stimulus responsive polymer treated cell culture, suggesting a less efficient elution when stimulus responsive polymer was not used.

Additionally, the absorbance of the loading solution is noticeably lower for the stimulus responsive polymer treated cell culture compared to the untreated cell culture, where the absorbance is reduced by 0.4-0.5 absorbance units (AU), suggesting a lower impurity challenge to the column.

After elution, the pH is raised to 5.0 for both sets of samples, then further raised to pH 7.5. At pH 5.0 there is no visible turbidity of the solutions. However, at pH 7.5 all elution samples exhibit increased levels of turbidity with significantly higher levels (99-644 NTU) for the untreated samples, while the stimulus responsive polymer treated elution pool turbidity ranges from 69.5 to 151 NTU, which is significantly lower relative to the untreated samples.

Example 7: Simultaneous Removal of Soluble and Insoluble Impurities from Affinity Capture Eluate Using Activated Carbon In this representative experiment, it was demonstrated that activated carbon, when packed with cellulose media, was capable of removing both insoluble (i.e., particulates) as well as soluble impurities from an eluate from the Protein A bind and elute chromatography step (i.e., capture step).

In many conventional processes used in the industry today, a depth filter is often used following the Protein A affinity capture step to remove insoluble impurities (i.e., particulates) before the next step, which typically is a cation exchange bind and elute chromatography step.

In the processes described herein, the use of a depth filter following the Protein A bind and elute chromatography is obviated. Notably, by using activated carbon following the Protein A bind and elute chromatography step, not only is the need for the cation exchange bind and elute chromatography step obviated, but also is the need to use a depth filter. This offers many advantages including, e.g., reducing the overall cost, process time as well as the overall physical footprint due to elimination of steps that are typically used.

As demonstrated herein, use of activated carbon leads to simultaneous removal of both soluble impurities (e.g., HCPs) as well as insoluble impurities (e.g., particulates).

A cell culture of monoclonal antibody MAb04 is subjected to Protein A affinity chromatography, and the pH of the elution pool is adjusted from pH 4.8 to pH 7.5, with dropwise addition of 1.0 M Tris base, in order to change solution conditions suitable for the next step in the process. However, raising the pH of the solution increases the turbidity, which in this case is measured to be 28.7 NTU. This solution is referred to below as the MAb04 Protein A eluate.

A circular section of a sheet of activated carbon-cellulose media ⅝ inch in diameter and 5 mm in thickness is cut and carefully loaded into 15 mm diameter Omnifit® Chromatography Columns (SKU: 006BCC-25-15-AF, Diba Industries, Inc, Danbury, Conn. 06810 USA) to result in a column volume of 0.89 mL. The column is flushed with 25 mM Tris pH 7. About 40 mL of the turbid MAb04 Protein A eluate is passed through the column at a flow rate of 0.20 mL/min, resulting in a residence time of 4.5 minutes. Four 10 mL fractions are collected. Each individual fraction as well as a combined pool composed of all four fractions is evaluated for turbidity and analyzed for the concentrations of HCP and MAb. HCP analysis is performed using a commercially available ELISA kit from Cygnus Technologies, Southport, N.C., USA, catalog number F550, following kit manufacturer's protocol. The MAb concentration is measured using an Agilent HPLC system equipped with a Poros® A Protein A analytical column. The results are summarized in Table V.

The results show that activated carbon is unexpectedly effective for the simultaneous removal of both the insoluble impurities (i.e., particulate matter) as well as the soluble impurities (i.e., HCPs) from the Protein A eluate. The turbidity of the Protein A eluate is reduced from 28.7 NTU to 9.9 NTU, while the concentration of HCP is reduced from 758 ppm to 104 ppm.

This result demonstrates that activated carbon, when packed with cellulose media, can be used for removing both soluble as well as insoluble impurities.

TABLE V

| volume loaded (mL) | activated carbon loading (kg/L) | Turbidity (NTU) | MAb (mg/mL) | HCP (ng/mL) | HCP (ppm) | HCP LRV |
|---|---|---|---|---|---|---|
| control | — | 28.7 | 10.38 | 7,872 | 758 | — |
| 10 | 0.13 | 8.8 | 9.76 | 130 | 13 | 1.77 |
| 20 | 0.25 | 10.3 | 10.53 | 850 | 81 | 0.97 |
| 30 | 0.38 | 10.3 | 10.55 | 1,660 | 157 | 0.68 |
| 40 | 0.50 | 10.6 | 10.38 | 2,333 | 225 | 0.53 |
| 40 (pool) | 0.50 | 9.9 | 10.59 | 1,098 | 104 | 0.86 |

Example 8: Effect of Residence Time on Impurity Removal by Activated Carbon

In this representative experiment, it was demonstrated that when activated carbon is used in a continuous process, as described herein, it results in a greater impurity removal relative to when it is not used in a continuous manner. Notably, when activated carbon is employed in a continuous process, as described herein, where it is usually in fluid communication with the Protein A bind and elute chromatography step upstream and with an anion exchange chromatography media downstream, the sample flows through the activated carbon at a flow-rate which is slower (i.e., having a longer residence time) relative to when activated carbon is used separately as a stand alone operation.

In this example, Protein A-purified MAb04 eluate is further subjected to a flow-through purification step which employs activated carbon (AC) and an anion exchange chromatography membrane device (e.g., a ChromaSorb™ device) configured in series, at four different flow rates. Antibody concentration in the feed is determined to be 7.5 g/L; HCP concentration is determined to be 296 ppm. The experiment is performed at pH 7.0. Activated Carbon, grade Nuchar HD, is obtained from MeadWestVaco. It is packed in a glass Omnifit column to bed volume of 0.8 mL. An anion exchange chromatography device with membrane volume 0.08 mL is connected in series to the AC column. The flow rates are chosen such that the residence time (RT) on AC is 1, 2, 4 or 10 mins. The MAb loading on AC and the anion exchange chromatography device is held constant at 0.5 kg/L and 5 kg/L, respectively, for the 4 different runs (i.e., having the four different residence times stated above).

Samples from the breakthrough of the anion exchange chromatography device are collected and analyzed for MAb and HCP concentrations. The breakthrough of HCP as a function of MAb loading on the anion exchange chromatography device at the 4 different residence times on AC mentioned above, is shown in FIG. 14.

Figure 14:
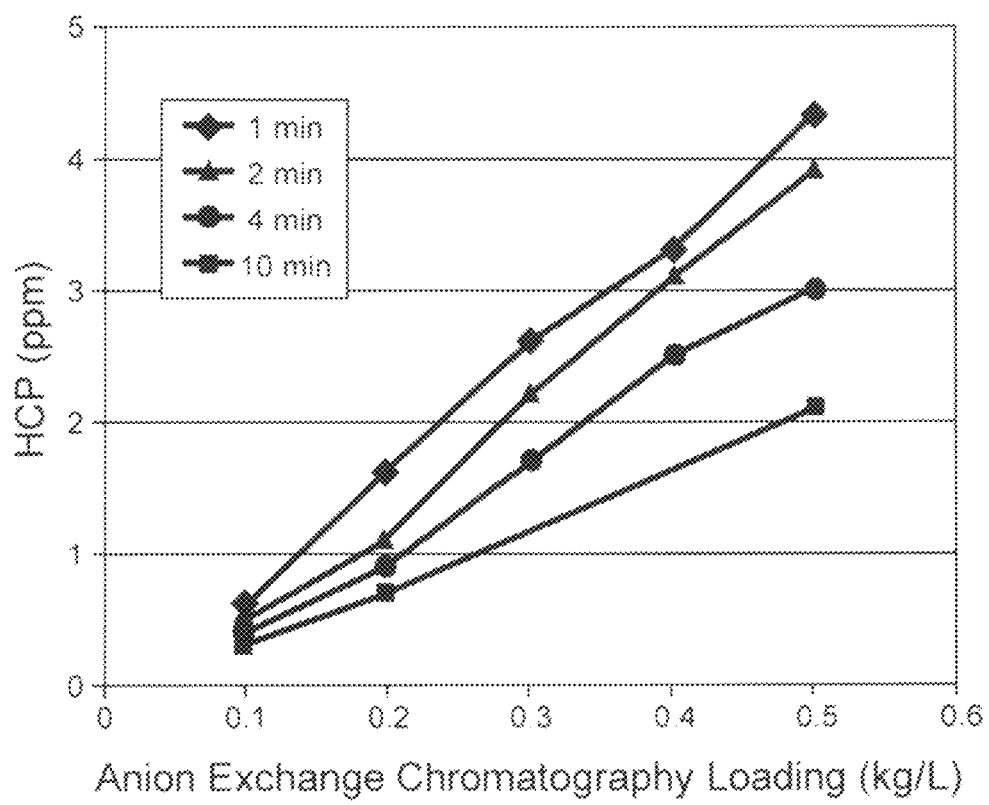
FIG. 14 is a graph depicting the results of an experiment to investigate the effect of residence time on HCP removal using activated carbon and an anion exchange chromatography (AEX) device, as part of the flow-through purification operation. The Y-axis denotes HCP concentration (ppm) and the X-axis denotes AEX load (kg/L).

As demonstrated in FIG. 14, lower flow rates on AC (i.e., longer residence times), provide better purity at same MAb loadings. Alternatively, the same purity can be achieved, with a smaller volume of AC and the anion exchange chromatography device at a slower flow rate. For example, the target purity of ~1 ppm HCP can be achieved using 2 kg/L loading on the anion exchange chromatography device (and 0.2 kg/L on AC), operating at 1 minute residence time. Notably, the same purity can be achieved while operating at a longer residence time of 10 mins (i.e., slower flow rate) with a significantly higher loading of 5 kg/L on the anion exchange chromatography device (and 0.5 kg/L on AC). This finding highlights a potential economic advantage in using less consumable purification material to achieve the same purity when the flow rate is reduced.

Example 9: Advantage of Using A Surge Tank in the Flow-Through Purification Process Step In this representative experiment, one or more advantages of using a surge tank in the flow-through purification process step, as described herein, are demonstrated.

Typically, cation exchange flow-through chromatography requires the sample to be at a pH of about 5. Accordingly, the pH of the sample has to be changed from about neutral pH to about pH 5.0, as it flows from the anion exchange chromatography step to the cation exchange chromatography step, when performing flow-through purification.

While the change in pH can be achieved by using an in-line static mixer, this example demonstrates that it is advantageous to additionally use a surge tank. Accordingly, the flow of the sample is as follows: anion exchange chromatography step to an in-line static mixer to a surge tank to the cation exchange chromatography step.

It is observed that if only an in-line static mixer is used for changing pH conditions between the anion exchange and the cation exchange flow-through chromatography steps, a sudden increase (i.e., a spike) is seen, as measured using a pH probe. It is understood that the pH spike is observed due to chemical differences in the composition of the sample and that of the buffer being added to change the pH. This pH spike is undesirable as it results in the sample being processed for a duration of time at a higher than is required for optimal results. This example demonstrates that this pH spike can be reduced or eliminated by the use of a surge tank after the in-line static mixer and before the sample contacts the cation exchange chromatography step, as shown in FIG. 15.

Figure 15:
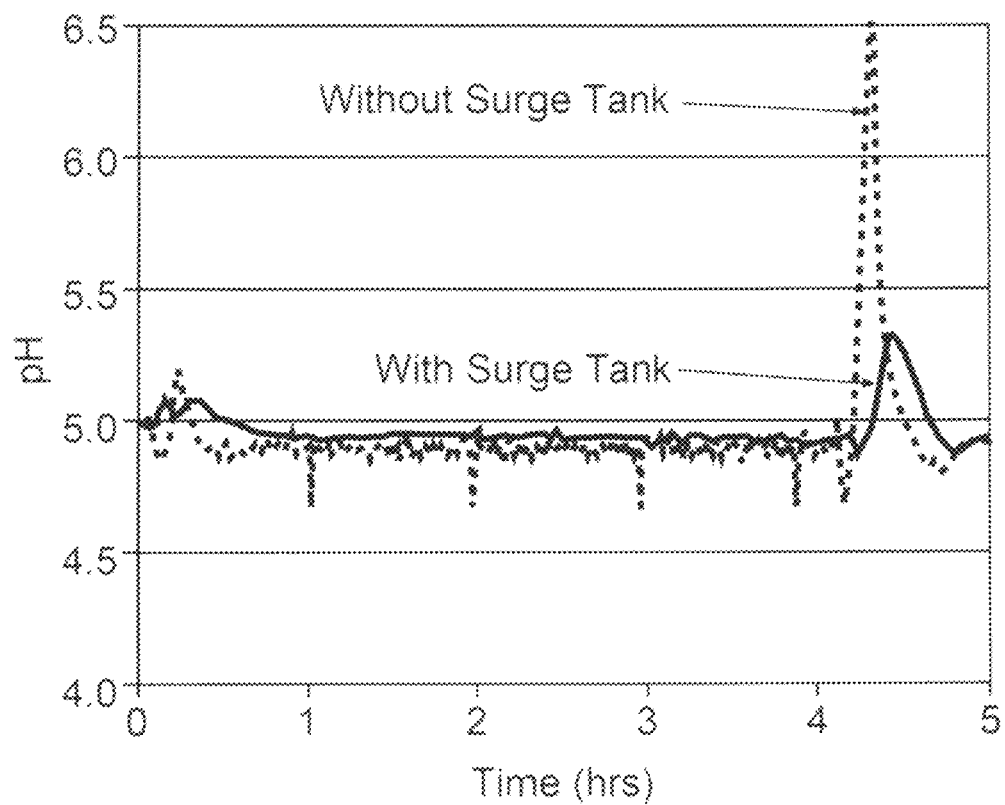
FIG. 15 is a graph depicting the results of an experiment to measure the effect on pH spike after using a surge tank between the flow-through anion exchange chromatography and cation exchange chromatography step in a flow-through purification operation. The X-axis denotes pH and the Y-axis denotes time in hours.

As shown in FIG. 15, a pH spike of about pH 6.5 is observed without the use of a surge tank. However, when a surge tank is used, as described herein, the pH falls to below pH 5.3, which is closer to the desirable pH for the subsequent cation exchange chromatography step.

Example 10: Running the Flow-Through Purification Process Step in a Continuous Manner is not Detrimental to Product Purity In this representative experiment, it is demonstrated that running a flow-through purification process in a continuous manner is not detrimental to product purity. In other words, by comparing the product purity from a flow-through purification process step run in a continuous manner to one where the individual steps are performed separately, it is shown that there is no detrimental effect on the product purity.

This example demonstrates that by connecting activated carbon and an anion exchange chromatography device (e.g., ChromaSorb™) in series to a cation exchange chromatography device, which acts as a virus prefilter, and a virus filtration device, and operating the entire flow-through purification process step continuously results in similar capacity of the virus filter, compared to when the activated carbon and the anion exchange chromatography device are decoupled from the cation exchange chromatography device and the virus filtration device.

Figure 16:
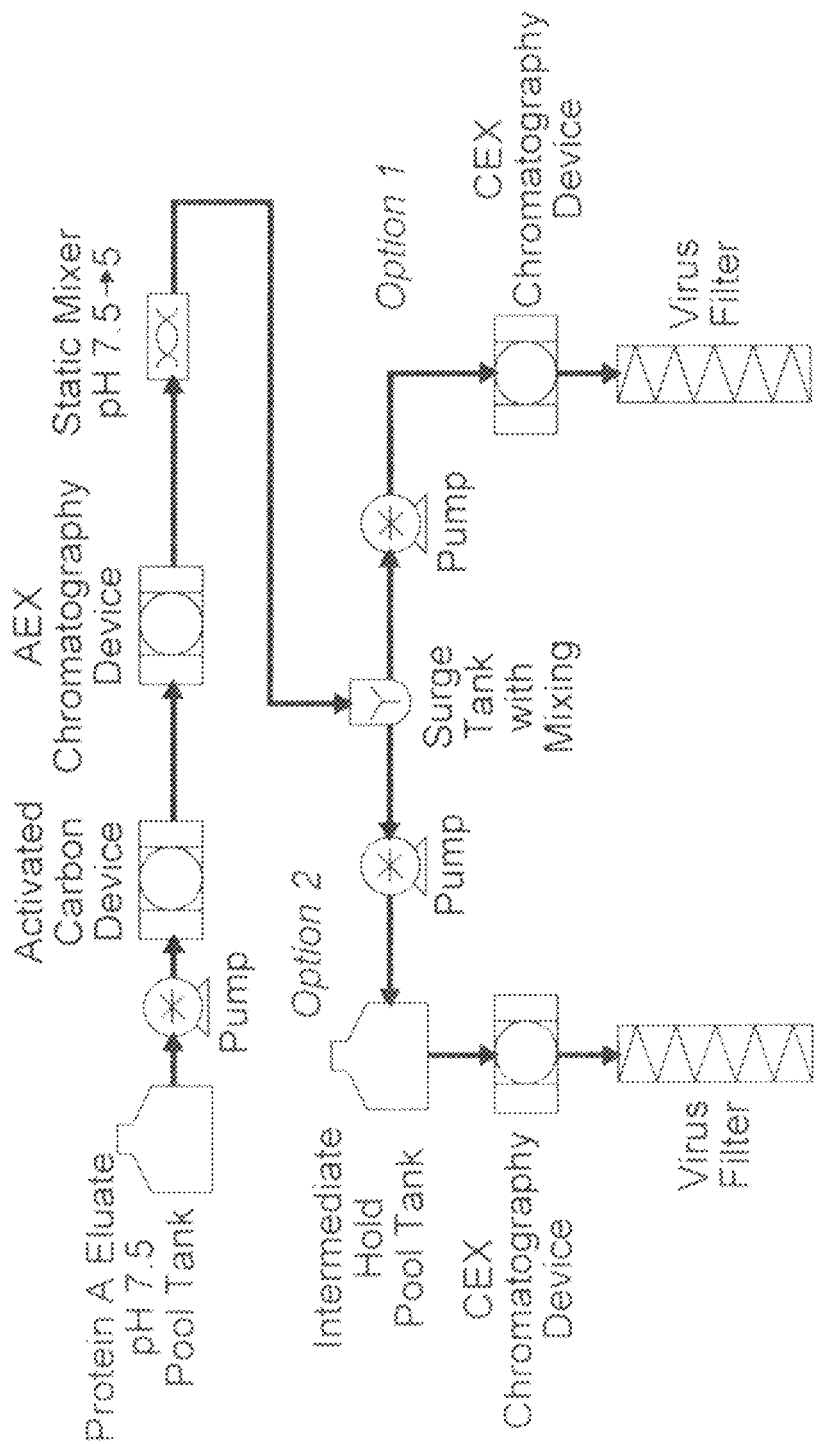
FIG. 16 is a schematic depiction of the experimental set up used for demonstrating that running the flow-through purification operation in a continuous manner does not have a detrimental effect on product purity.

The experimental set-up for this experiment is shown in FIG. 16. Option 1 in FIG. 16 refers to the continuous process, where the sample from the surge tank (present after anion exchange chromatography device) is fed directly into a cation-exchange chromatography device followed by a virus filtration device. Option 2 in FIG. 16 refers to a batch process where sample is pooled after activated carbon and the anion exchange chromatography device, and after a duration of time, it is processed through through a cation exchange chromatography device and the virus filtration device.

In this experiment, the starting sample is the Protein A bind and elute chromatography eluate, which has an HCP concentration of 250 ppm. It is observed that after activated carbon and anion exchange chromatography device, the HCP levels is reduced to about 4 ppm.

In case of the batch process (Option 2), the final HCP concentration following virus filtration is observed to be around 1 ppm; whereas in case of the continuous process (Option 1), the HCP concentration following virus filtration was about 2 ppm, both of which are towards the lower end of what can be quantified using methods known in the art and those described herein, e.g., assays described in Example 7.

This result implies that performing all the steps in the flow-through purification process step in a continuous manner results in a product purity, which is comparable to when one or more steps are performed as a stand alone operation.

Figure 17:
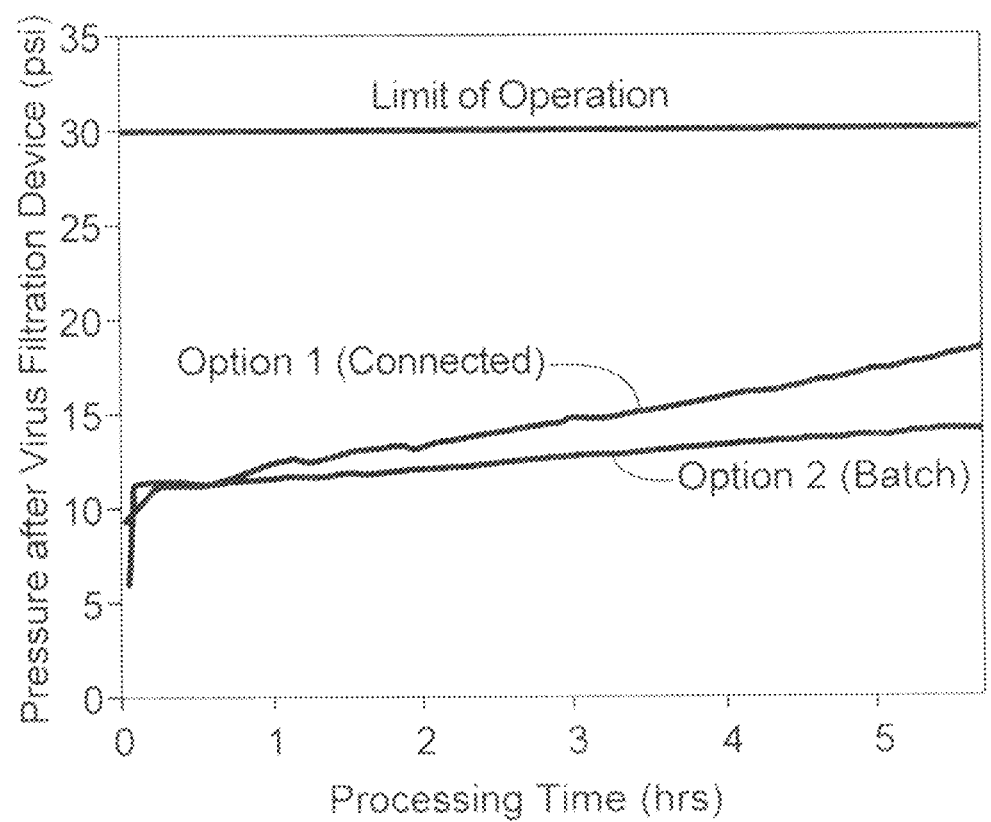
FIG. 17 is a graph depicting the results of an experiment to investigate pressure profiles after virus filtration, following use of a virus filtration device in a continuous format and in a batch mode. The Y-axis denotes pressure in psi and the X-axis denotes processing time in hours.

Additionally, it is noted that the the pressure profiles for the two processes are also very similar, as shown in FIG. 17.

Example 11: Effect of Residence Time on Performance of Virus Filtration Membrane In this representative experiment, the effect of residence time on performance of the virus filtration is investigated. It is observed that a lower flow rate through the cation exchange chromatography step and the virus filtration step during the flow through purification process step, results in a higher throughput of the virus filter.

A three-layer cation exchange chromatography device, as described in U.S. patent application Ser. No. 13/783,941 (internal ref no. MCA-1423), having membrane area 3.1 $cm^2$ and membrane volume 0.12 mL, is connected in a series to a virus filtration device, having a membrane area of 3.1 $cm^2$. About 3 mg/mL of a polyclonal human IgG (Seracare) in 20 mM sodium acetate, pH 5.0 buffer, is processed through the two connected devices. The experiment is performed at two separate flow-rates, 100 and 200 LMH. A 0.22 μm sterile filter is placed between cation exchange chromatography device and the virus filtration device.

Figure 18:
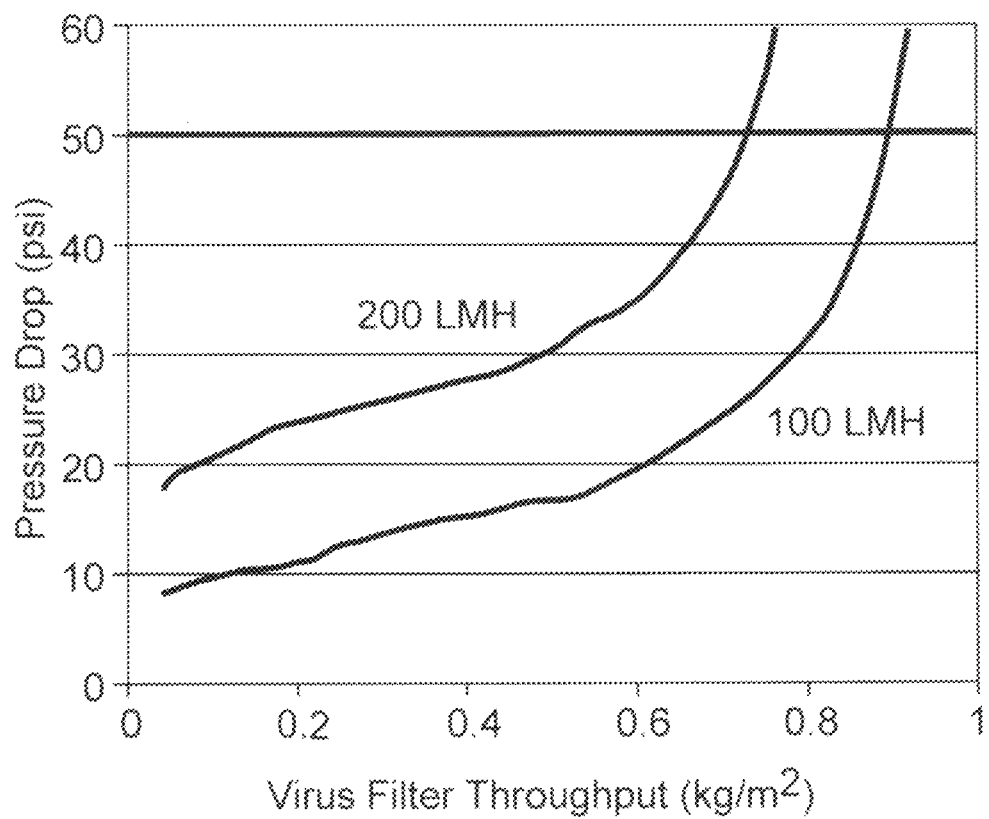
FIG. 18 is a graph depicting the results of an experiment to investigate the effect of flow-rate on throughput of the virus filtration device. The Y-axis denotes pressure drop (psi) and the X-axis denotes throughput of the virus filtration device (kg/m$^2$).

A pressure sensor is used for measuring the pressure across the assembly at the different flow rates. Normally, a pressure of about 50 psi is an indication of fouling or plugging of the virus filtration membrane. As shown in FIG. 18, when the experiment is performed at a lower flow-rate (i.e., 100 LMH), more sample volume can be processed through the virus filtration membrane (i.e., higher throughput) relative to when the sample is processed at a higher flow-rate (i.e., 200 LMH). This could be attributed to longer residence time of the sample in the cation exchange chromatography device, which may result in an improvement in binding of high molecular weight IgG aggregates, thereby preventing early plugging of the virus filter.

Example 12. Removal of Aggregates at Various Residence Times from a MAb Feed Using a Strong Cation-Exchange (CEX) Resin Modified with an AMPS/DMAM Grafted Copolymer In a 250 mL glass jar, 64 ml wet cake of Toyopearl HW75-F chromatography resin was added. Next, 115 g of 5M sodium hydroxide, 18.75 g of sodium sulfate, and 4 mL of allyl glycidyl ether (AGE) were added to the jar containing the resin. The jar was then placed in a hybridizer at 50° C. overnight, with rotation at medium speed. The next day, the resin was filter drained in a sintered glass filter assembly (EMD Millipore Corporation, Billerica, Mass.) and the wet cake was washed with methanol and then rinsed with deionized water. In a glass vial, 10 mL wet cake of the AGE activated resin was added. To the glass vial, 0.2 g of Ammonium persulfate, 0.3 g AMPS, 1.2 g DMAM, and 48 g of deionized water were added and the vial was heated to 60° C. for 16 hours. The next day, the resin was filter drained in a sintered glass filter assembly (EMD Millipore Corporation, Billerica, Mass.) and the wet cake was washed with a solution of methanol and deionized water and the resin was labeled as Lot #1712.

The resin, labeled as Lot #1712, was packed in an Omnifit® Chromatography Column with an internal diameter of 6.6 mm to a bed height of 3 cm resulting in about 1 mL packed resin bed. An AKTA Explorer 100 (chromatography system) was equipped and equilibrated with buffers appropriate to screen these columns for flow-through chromatography. The chromatography columns containing the resin sample were loaded onto the chromatography system with equilibration buffer. The feedstock was an IgG1 (MAb5) feedstock that was purified using ProSep® Ultra Plus Affinity Chromatography Media, and was adjusted to pH 5.0 with 2 M Tris Base. The final concentration of the Protein A pool was diluted to 4 mg/mL, contained 5.5% aggregated product, and a conductivity of about 3.2 mS/cm. The resin was loaded at a residence time of 1, 3, or 6 minutes and to a load density of 144 mg/mL. The strip peak fraction for the 3 minute residence time contained 95.6% aggregates indicating a high level of selectivity for aggregated species. The results are depicted in Table VI below.

Table VI depicts retention of monomer and aggregates for Lot #1712 with MAb5 at pH 5.0 at 6, 3, or 1 minute residence time. As shown in Table VI, on average, the monomeric species can be collected at concentrations close to the feed concentration relatively early compared to the aggregated species for all residence times tested, which suggests that selectivity is relatively insensitive to flow rates.

TABLE VI

| Flow-through Collection Fraction # | Cumulative Protein Load Density (mg/mL) | Average of 6, 3, or 1 Minute Residence Time % Protein in Flow-through | 6 Minutes Residence Time % Aggregates | 3 Minutes Residence Time % Aggregates | 1 Minute Residence Time % Aggregates |
|---|---|---|---|---|---|
| 1 | 16 | 13.5 | 0.0% | 0.0% | 0.0% |
| 2 | 32 | 94.3 | 0.0% | 0.0% | 0.0% |
| 3 | 48 | 94.4 | 0.0% | 0.0% | 0.0% |
| 4 | 64 | 95.2 | 0.0% | 0.0% | 0.0% |
| 5 | 80 | 98.3 | 0.5% | 0.0% | 0.0% |
| 6 | 96 | 100.0 | 0.7% | 0.3% | 0.0% |
| 7 | 112 | 99.3 | 1.1% | 0.9% | 2.1% |
| 8 | 128 | 100.0 | 2.3% | 1.6% | 2.8% |
| 9 | 144 | 100.0 | 3.1% | 3.6% | 4.8% |

Figure 19:
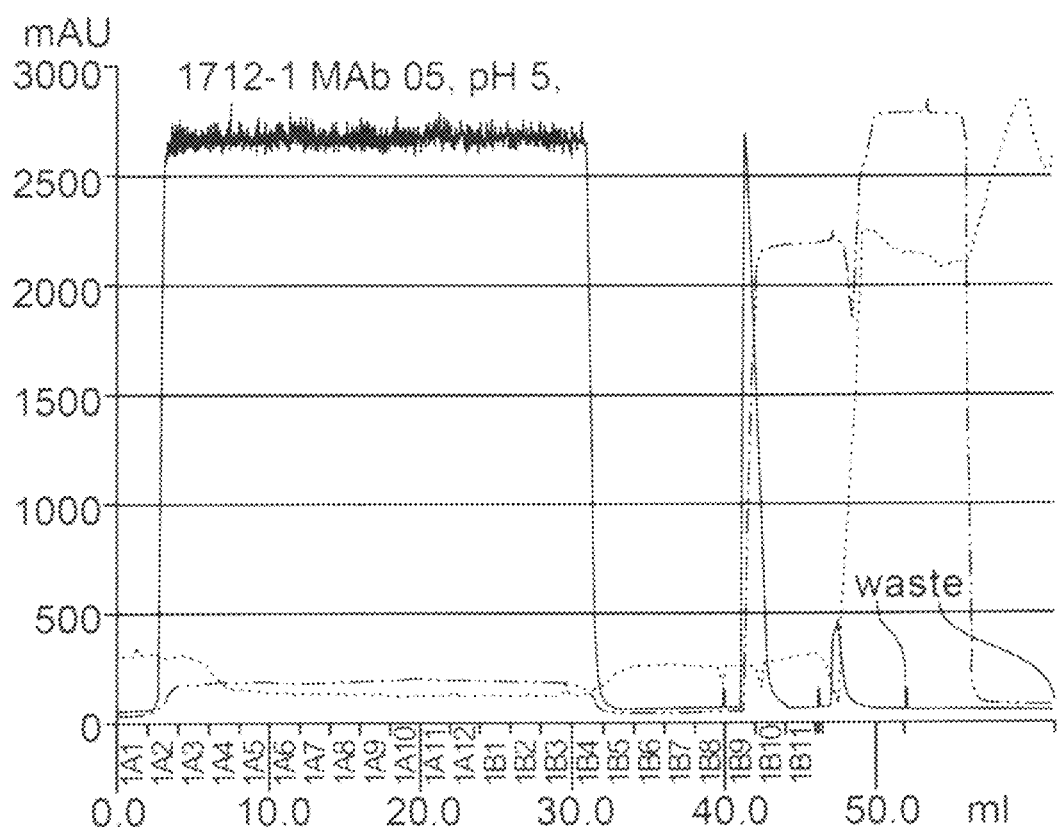
FIG. 19 depicts a chromatogram of Lot #1712 with MAb5 at pH 5.0 and 3 minutes residence time. As depicted in FIG. 19, the majority of the product is collected in the flow-through and this is indicated by the relatively quick breakthrough of protein UV trace. The strip peak size generally varies based on the conditions and total mass loaded but it is relatively enriched with aggregate species at 95.6%, compared to the load material which had only 5.5% aggregates.

As depicted in FIG. 19, the majority of the product is collected in the flow-through and this is indicated by the relatively quick breakthrough of protein UV trace. The strip peak size generally varies based on the conditions and total mass loaded but it is relatively enriched with aggregate species at 95.6%, compared to the load material which had only 5.5% aggregates.

Example 13: Removal of Aggregates from a MAb Feed Using Cation-Exchange (CEX) Winged Fibers Modified with an AMPS/DMAM Grafted Copolymer In this representative experiment, cation-exchange winged fibers were used as the solid support.

In a 1 L glass jar, 20 g of dry Nylon multi-lobed, or winged, fibers were combined with 400 g of 4M sodium hydroxide, 24 g of sodium sulfate, and 160 mL of allyl glycidyl ether (AGE). The jar was then placed in a hybridizer at 50° C. overnight rotating at medium speed. The following day, the fibers were filtered in a sintered glass filter assembly and the fibers were then washed with methanol and rinsed with Milli-Q water. A day later, the fibers were washed with water, followed by methanol, and then water again, suctioned to a thy cake and dried in vacuum oven at 50° C. for 1 day. The resulting sample was labeled Sample #1635. In three separate glass vials, 2 grams dry cake of Sample #1635, AGE activated fibers, were weighed out and added to a glass vial for additional modification by grafting. To the glass vial, ammonium persulfate, AMPS, DMAM, and deionized water were added in amounts specified in Table VII and the vial was heated to 60° C. for 16 hours with continuous rotation. The following day, the fiber samples were filtered in a sintered glass filter assembly and the wet cake was washed with a solution of deionized water. The vials containing the fibers were labeled as Lot #1635-1, 1635-2, and 1635-5. Next, Lot #1635-5 was titrated for small ion capacity, which was found to be about 28 µmol/mL. It was then assumed that samples #1635-1 and #1635-2 also had small ion capacity less than 28 µmol/mL.

TABLE VII

| Ingredients | #1635-1 | #1635-2 | #1635-5 |
|---|---|---|---|
| Fibers (g) | 2.0 | 2.0 | 2.0 |
| Ammonium persulfate (g) | 0.18 | 0.18 | 0.18 |
| AMPS (g) | 0.48 | 0.60 | 0.72 |
| DMAM (g) | 0.48 | 0.60 | 0.72 |
| Water (g) | 28.86 | 28.62 | 28.38 |

The resulting modified winged fibers, Lot #1635-1, #1635-2, #1635-5 were packed in an Omnifit® Chromatography Column with an internal diameter of 6.6 mm to a bed height of 3 cm resulting in about 1 mL packed fiber bed. An AKTA Explorer 100 (chromatography system) was equipped and equilibrated with buffers appropriate to screen these columns for flow-through chromatography. The chromatography columns containing the winged fiber samples were loaded onto the chromatography system with equilibration buffer. The feedstock was an IgG1 (MAb5) feedstock that was purified using protein A affinity chromatography, and was adjusted to pH 5.0 with 2 M Tris Base. The final concentration of the protein A pool was 4 mg/mL and contained 5.5% aggregated or HMW product. This is the same feedstock as used in Example 12. The columns packed with fiber Lot #1635-1 and Lot #1635-2 were loaded to a mass loading of 64 mg/mL and the column packed with fiber Lot 1635-5 was loaded to a mass loading of 80 mg/mL. The results are depicted in Table VIII below.

Example 14: The Combined Effect of Stimulus Responsive Polymer Clarification and Addition of NaCl to the Clarified Cell Culture on the Protein a Elution Pool Purity In this representative experiment, a MAb04 cell culture fluid is clarified using either depth filtration or a precipitation step, specifically using a stimulus responsive polymer (i.e., modified polyallylamine). The resulting clarified solutions are either loaded on to a column containing ProSep® Ultra Plus resin or have NaCl added to a final concentration of 0.5 M NaCl prior to loading onto the column. In the absence of the NaCl addition, the column is equilibrated with 1×TBS prior to loading, whereas with NaCl, the equilibration buffer is 1×TBS, 0.5 M NaCl. All columns are loaded to approximately 30 g of MAb04 per liter of resin and then washed with equilibration buffer for 2 CVs followed by a 3 CV wash with 25 mM Tris pH 7.0. The bound MAb04 is eluted with the 25 mM glycine HCl, 25 mM acetic acid pH 2.5 solution and then cleaned with 5 CVs of 0.15 M phosphoric acid pH 1.6 before being reequilibrated with the appropriate equilibration buffer.

Figure 20:
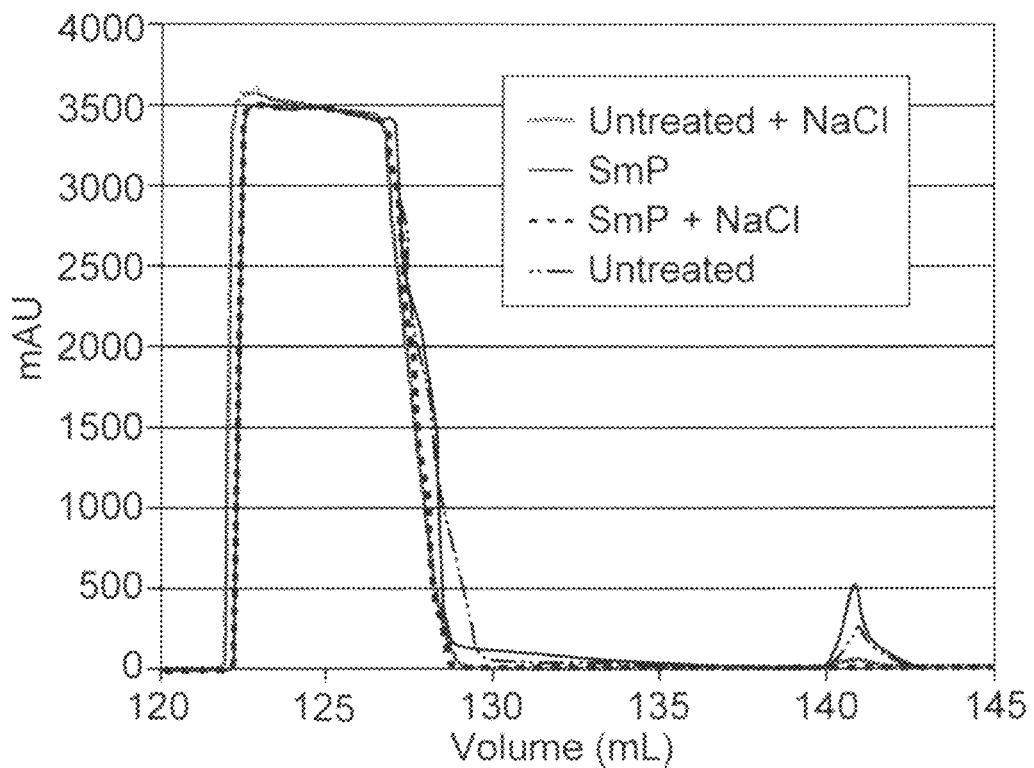
FIG. 20 is a graph depicting the elution (first peak between 120 to 130 ml) and regeneration (around 140 ml) peaks from the chromatogram of Protein A purification for cell culture treated with stimulus responsive polymer and/or NaCl. Also shown is the control without any treatment. The X-axis represents the volume passed through the Protein A column and the Y-axis represents the absorbance at 280 nm wavelength.

FIG. 20 displays an overlay of the elution and cleaning peaks, where the elution peak generated from the stimulus responsive polymer treated cell culture displays a sharper tail and a reduced cleaning peak. In the presence of NaCl, during the load with the stimulus responsive polymer treated cell culture, the cleaning peak is further reduced, thereby indicating a lower level of strongly bound impurities on the resin.

Example 15: Comparison of the Effect of Different NaCl Concentrations During Intermediate Washing Steps with the Effect of 0.5 M NaCl Present in the Loading Solution In this representative experiment, the impact of different NaCl concentrations during the intermediate washing steps on the monoclonal antibody (MAb) elution pool purity achieved by Protein A chromatography is directly compared to the impact of having 0.5 M NaCl in the sample being loaded onto a Protein A chromatography column.

A 5 mL column of ProSep® Ultra Plus Protein A media is acquired as a pre-packed column. All chromatography runs are performed using an Äkta Explorer chromatography system with a flow rate of 1.7 mL/min (~3 minute residence

TABLE VIII

| Cumulative protein load mg/mL | Fiber Lot #1635-1 | | | Fiber Lot #1635-2 | | | Fiber Lot #1635-5 | | |
|---|---|---|---|---|---|---|---|---|---|
| | Monomer (%) | Dimers (%) | LMW (%) | Monomer (%) | Dimers (%) | LMW (%) | Monomer (%) | Dimers (%) | LMS (%) |
| 8 | 0.0 | 0.0 | 0.0 | 0.0 | 0.0 | 0.0 | 0.0 | 0.0 | 0.0 |
| 16 | 85.8 | 0.0 | 14.0 | 86.0 | 0.0 | 15.6 | 1.7 | 0.0 | 10.2 |
| 24 | 84.3 | 0.0 | 15.6 | 85.6 | 0.0 | 14.8 | 51.8 | 0.0 | 13.4 |
| 32 | 83.2 | 0.6 | 16.0 | 83.0 | 0.0 | 17.1 | 85.6 | 0.0 | 15.1 |
| 40 | 79.4 | 2.4 | 17.7 | 81.1 | 0.0 | 14.9 | 86.5 | 0.0 | 13.9 |
| 48 | 79.6 | 4.4 | 15.8 | 82.5 | 1.5 | 15.9 | 83.3 | 0.0 | 15.8 |
| 56 | 82.4 | 4.4 | 12.8 | 79.4 | 2.1 | 18.3 | 87.1 | 0.0 | 13.1 |
| 64 | 81.1 | 4.5 | 14.2 | 83.1 | 3.1 | 14.7 | 85.4 | 2.3 | 13.6 |
| 72 | N/A* | N/A | N/A | N/A | N/A | N/A | 85.7 | 4.0 | 13.6 |
| 80 | N/A | N/A | N/A | N/A | N/A | N/A | 85.1 | 5.1 | 13.8 |
| Strip Peak | 38.0 | 63.5 | 0.0 | 54.4 | 35.0 | 11.0 | 51.3 | 43.0 | 5.6 |

*N/A = Not applicable time) for all steps. The same column is used for all experiments. For the first set of experiments, where NaCl is present in the intermediate wash, the chromatography step employed a 5 column volume equilibration with 1×TBS followed by loading of 300 mL of clarified cell culture containing a target protein (referred to as MAb05) at a concentration of approximately 0.57 g/L. Following the loading of cell culture, the column is flushed with 10 mL of equilibration buffer to remove any unbound product, impurities and other cell culture components. The column is then washed with 5 column volumes of 25 mM tris, pH 7.0 that also includes 0.5 M NaCl. The column is subsequently washed with 5 column volumes of 25 mM Tris, pH 7.0 without NaCl. The product protein (MAb05) is eluted from the column over 5 column volumes using a buffer containing 25 mM Acetic acid and 25 mM Glycine HCl at pH 2.5. The column is subsequently cleaned with 5 column volumes of 0.15 M Phosphoric acid followed by a 10 column volume regeneration step using the equilibration buffer. Equivalent runs are performed where the NaCl concentration during the first wash is varied between 0, 1.5 and 2 M.

The next experiment is performed using the same column with the following changes to the protocol. The cell culture sample being loaded is mixed with a volume of 5 M NaCl such that the final NaCl concentration in the clarified cell culture is 0.5 M NaCl. The equilibration buffer is modified to include 0.5 M NaCl in the 1×TBS solution. The column is loaded with 333 mL of clarified cell culture with 0.5 M NaCl present to maintain a constant mass loading of the target protein (MAb05). Intermediate washing is performed as previously described where a total of 10 column volumes of 25 mM Tris, pH 7.0 is used throughout. The elution and cleaning steps and buffers remain identical as described above. Table IX provides an abbreviated summary of the steps performed for each experiment, identifying the buffers and volumes used for each step where a potential change is made.

TABLE IX

| Sample number | Equilibration buffer (25 mL) | Loading volume | Intermediate wash buffer 1 (25 mL) | Intermediate wash buffer 2 (25 mL) |
|---|---|---|---|---|
| 1 | 1 X TBS | 300 mL | 25 mM Tris pH 7 | 25 mM Tris pH 7 |
| 2 | 1 X TBS | 300 mL | 25 mM Tris, 0.5M NaCl pH 7 | 25 mM Tris pH 7 |
| 3 | 1 X TBS | 300 mL | 25 mM Tris, 1.5M NaCl pH 7 | 25 mM Tris pH 7 |
| 4 | 1 X TBS | 300 mL | 25 mM Tris, 2M NaCl pH 7 | 25 mM Tris pH 7 |
| 5 | 1 X TBS, 0.5M NaCl | 333 mL | 25 mM Tris pH 7 | 25 mM Tris pH 7 |

Figure 21:
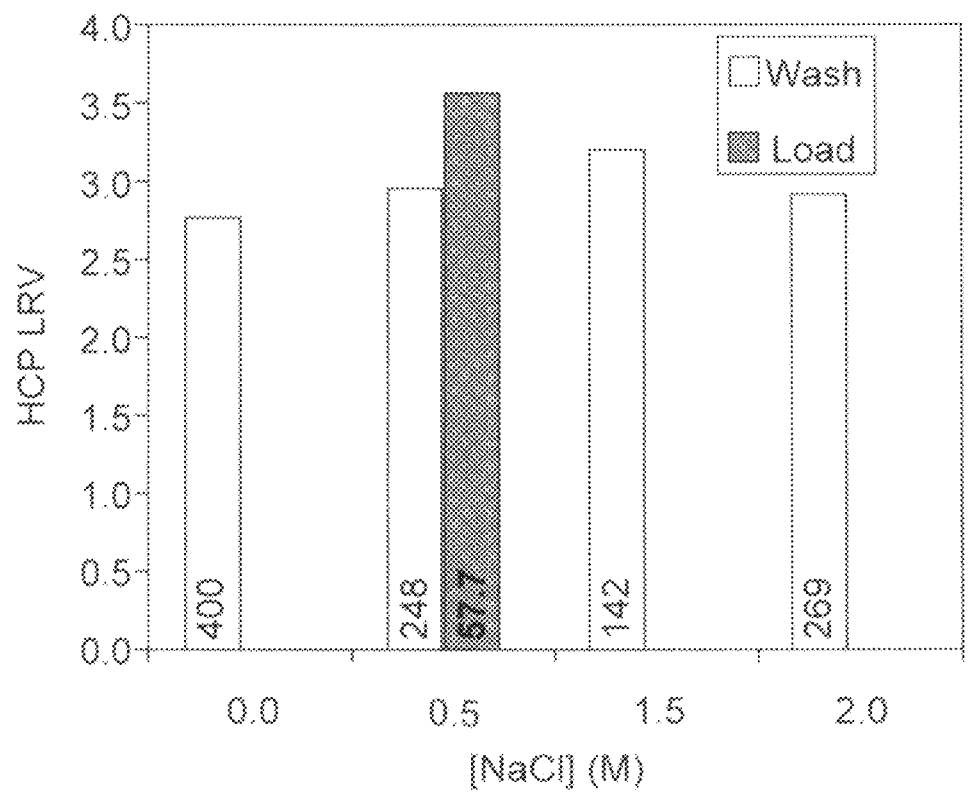
FIG. 21 is a bar graph depicting the HCP LRV as a function of NaCl concentration used in the intermediate wash or the loading step during Protein A chromatography. The X-axis represents the NaCl concentration in Molar (M) and the Y-axis represents the HCP LRV.
Figure 22:
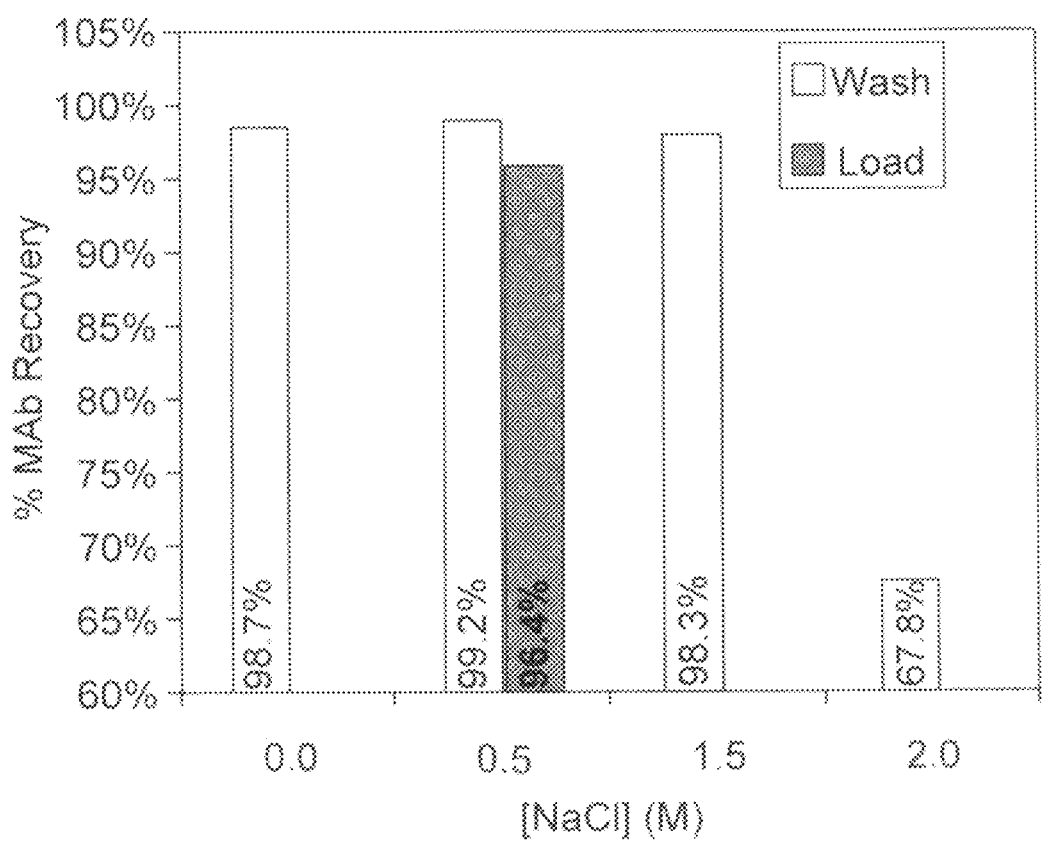
FIG. 22 is a bar graph depicting the product (MAb) percentage recovery as a function of the NaCl concentration in either the intermediate wash step or the loading step during Protein A chromatography. The X-axis represents the NaCl concentration in M and the Y-axis represents the percent MAb recovery.

Samples of the loading cultures and the elution pools are measured for MAb05 concentration and HCP concentration. FIG. 21 shows the HCP LRV as a function of the NaCl concentration used in the intermediate wash or used in the loading step. The Figure illustrates the improved level of HCP removal (purification) when 0.5 M NaCl is present in the equilibration buffer and clarified cell culture during the loading phase compared to the addition of NaCl to the intermediate washing steps, at varying concentrations. The results also provide the measured HCP concentrations in parts per million (ppm) based on the ng of HCP per mg of MAb05, shown as number within the corresponding bar. Further, FIG. 22 shows the % MAb05 recovered in the elution pool as compared to the mass loaded, where it is clearly observed that with 2 M NaCl present during the intermediate wash step, a significant loss of product is realized.

Example 16: Comparison of the Product Purification Achieved Based on the Protein A Purification Step During which an Additive is Included In this representative experiment, a direct comparison is made between the purification achieved by Protein A chromatography with an additive present in the intermediate wash only to the purification achieved with an additive in the equilibration buffer and cell culture samples that are loaded.

A 5 mL column of ProSep® Ultra Plus Protein A media is acquired as a pre-packed column. All chromatography runs are performed using an Äkta Avant chromatography system with a flow rate of 1.7 mL/min (~3 minute residence time) for all steps. The same column is used for all experiments. For all washing experiments, the method described in Example 15 above applies where NaCl is replaced with a specific additive at a defined concentration. The additives and concentrations used are provided in Table X.

TABLE X

| | | | Measured conductivity of solutions (mS/cm) | | |
|---|---|---|---|---|---|
| Additive identity | Stock Concentration | Final working concentration | TBS + additive (16.07-TBS alone) | Wash buffer (25 mM Tris + additive-1.2-Tris buffer alone) | MAb05 cell culture + additive (0.016-cell culture alone) |
| NaCl | 5M | 0.5M | 53.4 | 50.0 | 31.9 |
| Urea | 8M | 0.5M | 13.4 | 1.96 | 8.29 |
| Ammonium Sulfate | 3M | 0.5M | 78.0 | 69.2 | 47.6 |
| Tween-20 | 100% | 0.5% | 14.0 | 1.97 | 15.6 |
| Pluronic F-68 | 10% | 0.5% | 13.3 | 1.89 | 15.4 |
| PEG 400 | 100% | 10% | 9.89 | 1.44 | 4.66 |
| PEG 8000 | 30% | 5% | 10.9 | 1.53 | 10.9 |
| TMAC | 5M | 0.5M | 48.1 | 37.9 | 47.1 |
| Hexylene glycol | 100% | 5% | 12.0 | 1.69 | 5.84 |

Figure 23:
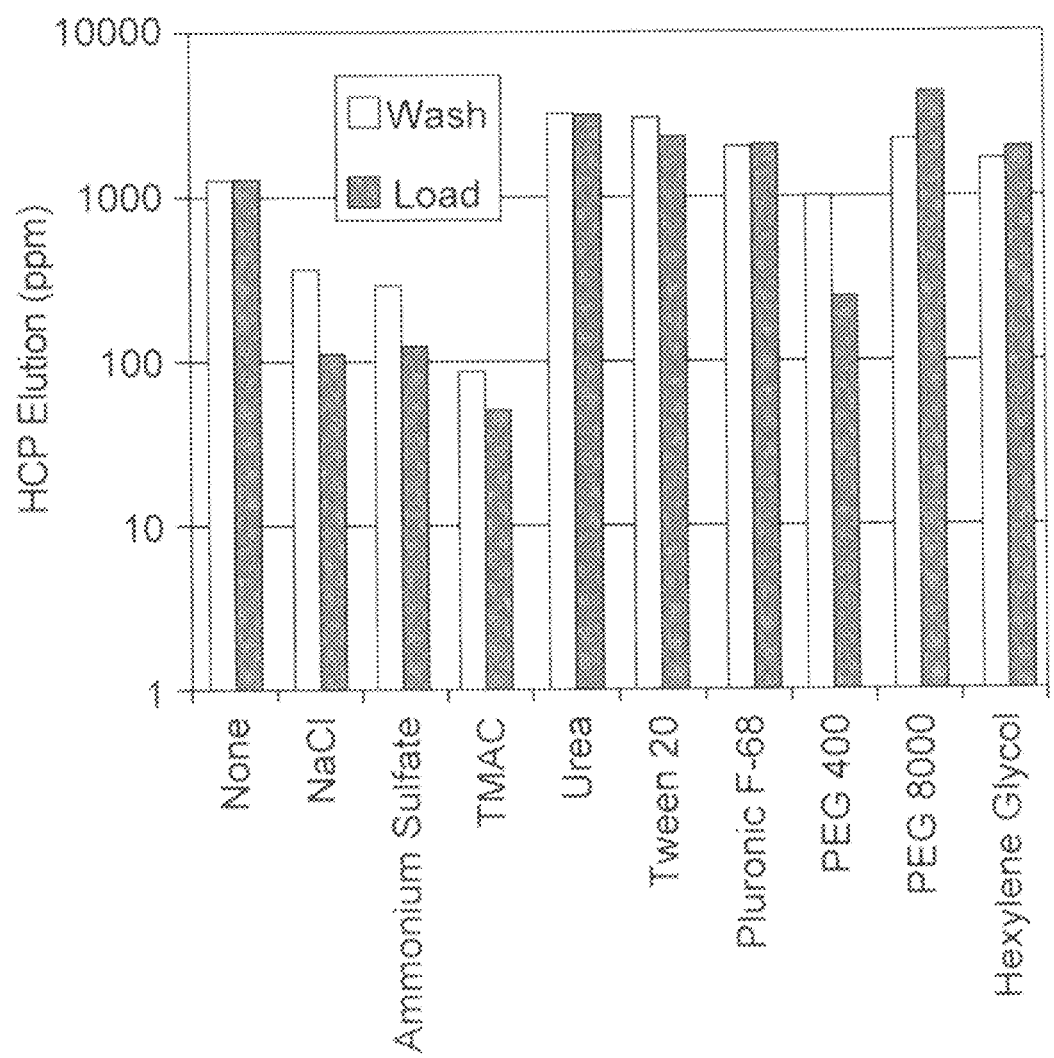
FIG. 23 is a bar graph depicting the HCP concentration in parts per million (ppm) as a function of the additive included in either the intermediate wash step or the loading step during Protein A chromatography. The X-axis represents the additive included and the Y-axis represents the HCP concentration in ppm.

FIG. 23 shows the concentration of HCP remaining in the product elution pool for each additive used whether it is present in the first intermediate wash step or in the equilibration buffer and cell culture sample. The addition of different salts (NaCl, Ammonium Sulfate or TMAC) shows the lowest HCP levels, when the salts are present in the loading phase.

Figure 24:
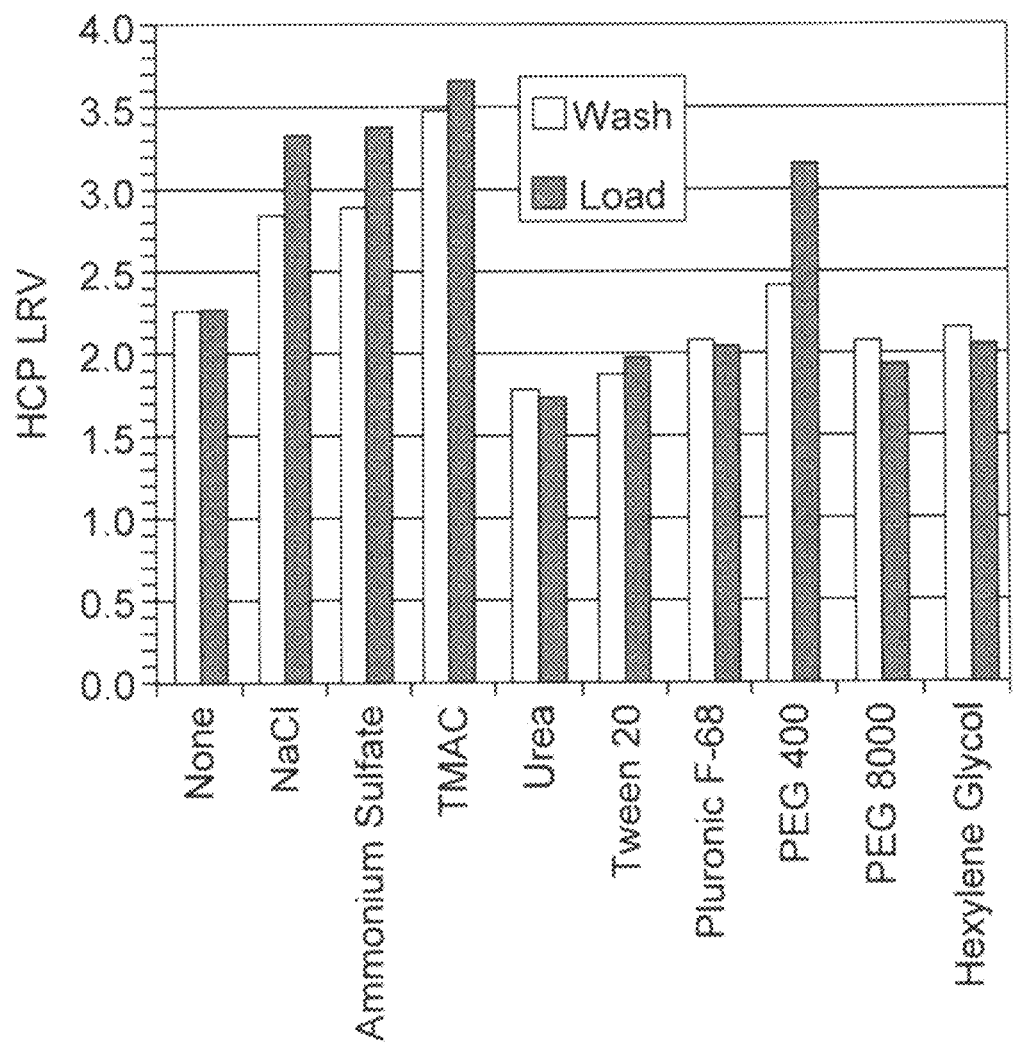
FIG. 24 is a bar graph depicting the HCP LRV as a function of the additive included in either the intermediate wash step or the loading step during Protein A chromatography. The X-axis represents the additive included and the Y-axis represents the HCP LRV.

FIG. 24 shows the LRV of HCP (relative to the loading HCP concentration) as a function of the additive used and the purification step during which the additive is used. This figure illustrates, again, that salts are most effective at reducing the HCP concentrations, i.e., increasing the HCP LRV. As demonstrated, the presence of the additive in the loading solutions shows improved impurity clearance when compared to the same additive present only in the intermediate wash. Tables XI and XII summarize the numerical results illustrated in FIGS. 23 and 24 with Table XI showing data when the additive is present in the loading step and Table XII showing data when the additive is present only during the intermediate wash.

TABLE XI

| Additive | [MAb05] in elution pool (g/L) | MAb05% Recovery | [HPC] in cell culture load (ppm) | [HPC] in elution pool (ppm) | HCP LRV |
|---|---|---|---|---|---|
| None | 13.26 | 93.1 | 220350 | 1226 | 2.25 |
| NaCl | 13.49 | 92.0 | 217850 | 106.8 | 3.31 |
| Ammonium Sulfate | 13.64 | 94.9 | 279871 | 124.6 | 3.35 |
| TMAC | 15.44 | 99.9 | 218200 | 49.5 | 3.64 |
| Urea | 12.83 | 95.6 | 166382 | 3133 | 1.73 |
| Tween-20 | 13.01 | 94.2 | 222464 | 2371 | 1.97 |
| Pluronic F-68 | 13.28 | 87.5 | 232195 | 2140 | 2.04 |
| PEG 400 | 14.15 | 76.2 | 341212 | 252.0 | 3.13 |
| PEG 8000 | 14.18 | 173.8 | 374388 | 4475 | 1.92 |
| Hexylene Glycol | 13.73 | 99.9 | 230147 | 2053 | 2.05 |

TABLE XII

| Additive | [MAb05] in elution pool (g/L) | MAb05% Recovery | [HPC] in cell culture load (ppm) | [HPC] in elution pool (ppm) | HCP LRV |
|---|---|---|---|---|---|
| None | 13.26 | 93.1 | 220350 | 1226 | 2.25 |
| NaCl | 13.04 | 103.9 | 232274 | 350.0 | 2.82 |
| Ammonium Sulfate | 13.11 | 98.5 | 208246 | 279.8 | 2.87 |
| TMAC | 15.20 | 83.9 | 241755 | 85.28 | 3.45 |
| Urea | 12.93 | 90.1 | 189352 | 3211 | 1.77 |
| Tween-20 | 12.79 | 91.7 | 227974 | 3032 | 1.88 |
| Pluronic F-68 | 13.76 | 103.5 | 243325 | 2034 | 2.08 |
| PEG 400 | 14.47 | 112.4 | 236376 | 915.0 | 2.41 |
| PEG 8000 | 14.40 | 101.9 | 251847 | 2204 | 2.06 |
| Hexylene Glycol | 14.00 | 75.3 | 244069 | 1738 | 2.15 |

Figure 25:
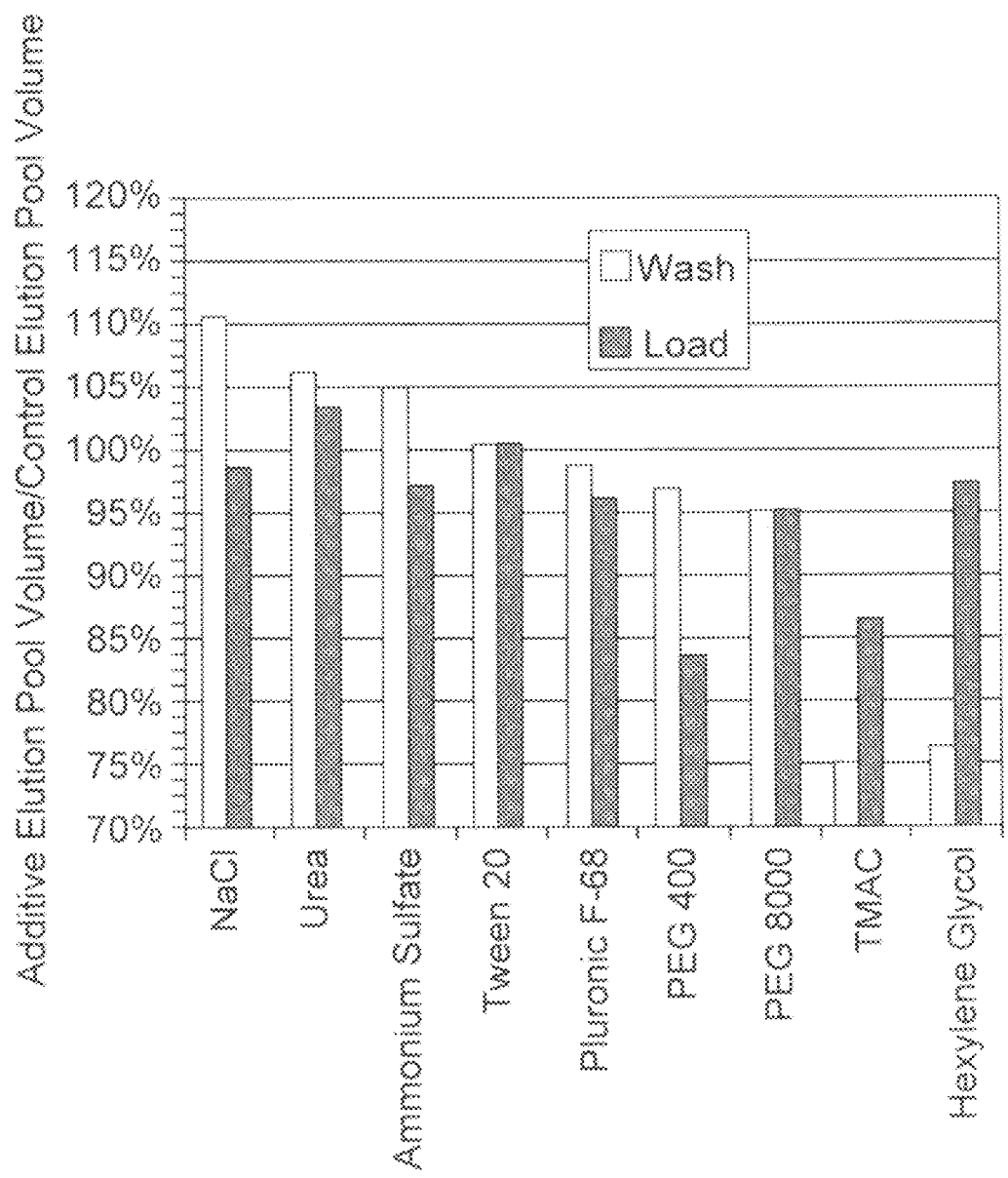
FIG. 25 is a bar graph depicting the ratio of the additive elution pool volume to the control elution pool volume as a function of the additive included in either the intermediate wash step or the loading step during Protein A chromatography. The X-axis represents the additive included and the Y-axis represents the ratio of the additive elution pool volume to the control elution pool volume.

FIG. 25 illustrates an example of the relative elution pool volume depending on the additive identity and the chromatography step during which the additive is included. The Figure shows that when the ratio of the additive elution pool volume to the control elution pool volume (i.e., where no additives are present) is greater than 100%, the additive elution pool volume exceeds the control elution volume. Conversely, the values less than 100% indicate a decrease in the additive elution pool volume relative to the control elution pool volume. This Figure further demonstrates the impact of the additives on the elution pool volume. A value less than 100% is preferred. Combining the information provided in FIGS. 23, 24 and 25 with the numerical data in Tables XI and XII, the order of the best performing conditions are TMAC in load>TMAC in wash>Ammonium Sulfate in load>NaCl in load>Ammonium sulfate in wash. The order provided here is based on the HCP LRV as of primary importance followed by product recovery. If HCP concentration in ppm is of primary importance, the order changes slightly to TMAC in load>TMAC in wash>NaCl in load>Ammonium Sulfate in load>Ammonium sulfate in wash.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A continuous process for the purification of a target molecule comprising the steps of:
    a) providing a sample comprising the target molecule and one or more impurities;
    b) adding at least one precipitant to the sample and removing one or more impurities, thereby to recover a clarified sample;
    c) subjecting the clarified sample from step (b) to a bind and elute chromatography step comprising at least two separation units, thereby to obtain an eluate comprising the target molecule; and
    d) subjecting the eluate to flow-through purification comprising use of two or more media, one of which is activated carbon and the other(s) are selected from anion-exchange chromatography media and cation-exchange chromatography media;
        wherein at least two steps are performed concurrently for at least a portion of their duration, wherein the process comprises only one bind and elute chromatography step, and wherein the process is a continuous process,
        wherein the process comprises use of one or more surge tanks and/or one or more static mixers, wherein the flow-through purification is carried out as: activated carbon followed by anion-exchange chromatography media followed by cation-exchange chromatography media, and
        wherein the in-line static mixer and/or surge tank is used between anion-exchange chromatography media and cation-exchange chromatography media to change pH.

2. The process of claim 1, comprising a virus inactivation step between steps (c) and (d).

3. The process of claim 2, wherein the virus inactivation step comprises use of a virus inactivating agent selected from acid, detergent, solvent and temperature change.

4. The process of claim 2, wherein virus inactivation step comprises use of one or more in-line static mixers.

5. The process of claim 2, wherein virus inactivation comprises use of one or more surge tanks.

6. The process of claim 1, wherein the target molecule is an antibody.

7. The process of claim 6, wherein the antibody is selected from a monoclonal antibody or a polyclonal antibody.

8. The process of claim 1, wherein the precipitant in step (b) is a stimulus responsive polymer.

9. The process of claim 8, wherein the stimulus responsive polymer is a modified polyallylamine polymer.

10. The process of claim 1, wherein the precipitant in step (b) is selected from the group consisting of an acid, caprylic acid, a flocculant and a salt.

11. The process of claim 1, wherein removing impurities in step (b) comprises use of one or more depth filters.

12. The process of claim 1, wherein removing impurities in step (b) comprises use of centrifugation.

13. The process of claim 1, wherein the bind and elute chromatography step in (c) employs continuous multi-column chromatography.

14. The process of claim 1, wherein the bind and elute chromatography step in (c) is selected from the group consisting of affinity chromatography, cation exchange chromatography and mixed-mode chromatography.

15. The process of claim 1, wherein the bind and elute chromatography step in (c) employs Protein A affinity chromatography.

16. The process of claim 15, wherein Protein A affinity chromatography employs a Protein A ligand coupled to a matrix selected from the group consisting of rigid hydrophilic polyvinylether polymer, controlled pore glass and agarose.

17. The process of claim 1, wherein the sample in step (a) is a cell culture.

18. The process of claim 17, wherein the cell culture is provided in a bioreactor.

19. The process of claim 18, wherein the bioreactor is a single use bioreactor.

20. The process of claim 17, wherein the cell culture is provided in a vessel other than a bioreactor.

21. The process of claim 1, wherein the precipitant in step (b) is added to a bioreactor comprising a cell culture.

22. The process of claim 21, wherein the precipitant is added using a static mixer.

23. The process of claim 1, wherein the precipitant in step (b) is added to a vessel other than a bioreactor which comprises the sample comprising the target molecule.

24. The process of claim 1, wherein the flow-through purification in step (d) further comprises use of a virus filtration membrane.

25. The process of claim 1, wherein the cation exchange chromatography media is in the form of a membrane, a bead or a fiber.

26. The process of claim 1, wherein the process comprises use of one or more surge tanks and does not employ any pool tanks between process steps.

27. The process of claim 1, further comprising a formulation step.

28. The process of claim 27, wherein formulation comprises diafiltration, concentration and sterile filtration.

29. The process of claim 28, further concentration comprises tangential flow filtration.

* * * * *